US010226452B2

(12) United States Patent
Piomelli et al.

(10) Patent No.: US 10,226,452 B2
(45) Date of Patent: *Mar. 12, 2019

(54) BENZOXAZOLONE DERIVATIVES AS ACID CERAMIDASE INHIBITORS, AND THEIR USE AS MEDICAMENTS

(71) Applicants: FONDAZIONE ISTITUTO ITALIANO DI TECNOLOGIA, Genoa (IT); THE REGENTS OF THE UNIVERSITY OF CALIFORNIA, Oakland, CA (US)

(72) Inventors: Daniele Piomelli, Irvine, CA (US); Chiara Pagliuca, Arezzo (IT); Daniela Pizzirani, Genoa (IT); Anders Bach, Valby (DK); Natalia Realini, Valmorea (IT); Marco De Vivo, Genoa (IT)

(73) Assignees: The Regents of the University of California, Oakland, CA (US); Fondazione Istituto Italiano di Tecnologia, Genoa (IT)

(*) Notice: Subject to any disclaimer, the term of this patent is extended or adjusted under 35 U.S.C. 154(b) by 0 days.

This patent is subject to a terminal disclaimer.

(21) Appl. No.: 15/346,443

(22) Filed: Nov. 8, 2016

(65) Prior Publication Data
US 2017/0182010 A1 Jun. 29, 2017

Related U.S. Application Data
(63) Continuation of application No. PCT/EP2015/060291, filed on May 11, 2015.

(30) Foreign Application Priority Data
May 12, 2014 (IT) .............................. MI2014A0863

(51) Int. Cl.
| A61K 31/423 | (2006.01) |
| A61K 31/4439 | (2006.01) |
| A61K 45/06 | (2006.01) |
| C07D 263/58 | (2006.01) |
| C07D 413/12 | (2006.01) |

(52) U.S. Cl.
CPC ........ *A61K 31/423* (2013.01); *A61K 31/4439* (2013.01); *A61K 45/06* (2013.01); *C07D 263/58* (2013.01); *C07D 413/12* (2013.01)

(58) Field of Classification Search
None
See application file for complete search history.

(56) References Cited

U.S. PATENT DOCUMENTS
7,709,513 B2   5/2010  Zoller et al.
2017/0182009 A1   6/2017  Piomelli et al.

FOREIGN PATENT DOCUMENTS

| EP | 1287815 A1 | 3/2003 |
| GB | 2 074 561 A | 11/1981 |
| WO | WO-2005/051891 A1 | 6/2005 |
| WO | WO-2006/050264 A1 | 5/2006 |
| WO | WO-2006/131233 A1 | 12/2006 |
| WO | WO-2007/136635 A1 | 11/2007 |
| WO | WO-2007/136635 A8 | 11/2007 |
| WO | WO-2010/054223 A1 | 5/2010 |
| WO | WO-2013/178545 A1 | 12/2013 |
| WO | WO-2013/178576 A1 | 12/2013 |
| WO | WO-2015/173168 A1 | 11/2015 |
| WO | WO-2015/173169 A1 | 11/2015 |

OTHER PUBLICATIONS

Bai, A. et al. (Mar. 1, 2009, e-published Jan. 31, 2009). "Synthesis and bioevaluation of omega-N-amino analogs of B13," *Bioorg Med Chem* 17(5):1840-1848.
Bedia, C. et al. (Nov. 2008, e-published Aug. 8, 2008). "Cytotoxicity and acid ceramidase inhibitory activity of 2-substituted aminoethanol amides," *Chem Phys Lipids* 156(1-2):33-40.
Bedia, C. et al. (Dec. 2010, e-published Sep. 24, 2010). "A simple fluorogenic method for determination of acid ceramidase activity and diagnosis of Farber disease," *J Lipid Res* 51(12):3542-3547.
Bhabak, K.P. et al. (Oct. 15, 2012, e-published Aug. 31, 2012). "Novel amide- and sulfonamide-based aromatic ethanolamines: effects of various substituents on the inhibition of acid and neutral ceramidases," *Bioorg Med Chem* 20(20):6162-6170.
Bhabak, K.P. et al. (Feb. 15, 2013, e-published Dec. 21, 2012). Effective inhibition of acid and neutral ceramidases by novel B-13 and LCL-464 analogues.
Bielawska, A. et al. (May 24, 1996). "(1S,2R)-D-erythro-2-(N-myristoylamino)-1-phenyl-1-propanol as an inhibitor of ceramidase," *J Biol Chem* 271(21):12646-12654.
Bielawska, A. et al. (Jan. 15, 2008, e-published Aug. 24, 2007). "Novel analogs of D-e-MAPP and B13. Part 2: signature effects on bioactive sphingolipids," *Bioorg Med Chem* 16(2):1032-1045.
Draper, J.M. et al. (Nov. 2011, e-published Sep. 1, 2011). "Discovery and evaluation of inhibitors of human ceramidase," *Mol Cancer Ther* 10(11):2052-2061.
International Search Report dated Jul. 20, 2015, for PCT Application No. PCT/EP2015/060291, filed on May 11, 2015, 4 pages.
International Search Report dated Jul. 20, 2015, for PCT Application No. PCT/EP2015/060292, filed on May 11, 2015, 4 pages.
Gangoiti, P. et al. (Oct. 2010, e-published Mar. 1, 2010). "Control of metabolism and signaling of simple bioactive sphingolipids: Implications in disease," *Prog Lipid Res* 49(4):316-334.
Grijalvo, S. et al. (Oct. 2006, e-published Aug. 7, 2006). "Design, synthesis and activity as acid ceramidase inhibitors of 2-oxooctanoyl and N-oleoylethanolamine analogues," *Chem Phys Lipids* 144(1):69-84.

(Continued)

Primary Examiner — Samantha L Shterengarts
(74) Attorney, Agent, or Firm — Anson M. Nomura; Mintz, Levin, Cohn, Ferris, Glovsky and Popeo, P.C.

(57) ABSTRACT

The present invention relates to benzoxazolone derivatives as acid ceramidase inhibitors, pharmaceutical compositions containing these inhibitors and methods of inhibiting acid ceramidase for the treatment of disorders in which modulation of the levels of ceramide is clinically relevant. The invention also provides benzoxazolone derivatives for use as a medicament in the treatment of cancer, inflammation, pain, inflammatory pain or pulmonary diseases.

21 Claims, 9 Drawing Sheets

(56) References Cited

OTHER PUBLICATIONS

Guenadil, F. et al. (2011). "Design and synthesis of 3-acyl-2(3H)-benzoxazolone and 3-acyl-2(3H)-benzothiazolone derivatives," *Monatsh Chem* 142:67-80.

Hannun, Y.A. et al. (Feb. 2008). "Principles of bioactive lipid signalling: lessons from sphingolipids," *Nat Rev Mol Cell Biol* 9(2):139-150.

Holman, D.H. et al. (Feb. 2008, e-published Apr. 12, 2007). "Lysosomotropic acid ceramidase inhibitor induces apoptosis in prostate cancer cells," *Cancer Chemother Pharmacol* 61(2):231-242.

Mahdy, A.E. et al. (Mar. 2009, e-published Dec. 23, 2008). "Acid ceramidase upregulation in prostate cancer cells confers resistance to radiation: AC inhibition, a potential radiosensitizer," *Mol Ther* 17(3):430-438.

Mao, C. et al. (Sep. 2008, e-published Jun. 13, 2008). "Ceramidases: regulators of cellular responses mediated by ceramide, sphingosine, and sphingosine-1-phosphate," *Biochim Biophys Acta* 1781(9):424-434.

Martin, R.E. et al. (Mar. 2007). "Remote modulation of amine basicity by a phenylsulfone and a phenylthio group," *ChemMedChem* 2(3):285-287.

Morad, S.A. et al. (Jan. 2013, e-published Dec. 13, 2012). "Ceramide-orchestrated signalling in cancer cells," *Nat Rev Cancer* 13(1):51-65.

Ogretmen, B. et al. (Aug. 2004). "Biologically active sphingolipids in cancer pathogenesis and treatment," *Nat Rev Cancer* 4(8):604-616.

Patti, G.J. (Jan. 22, 2012). "Metabolomics implicates altered sphingolipids in chronic pain of neuropathic origin," *Nat Chem Biol* 8(3):232-234.

Pizzirani, D. et al. (May 2013, e-published Apr. 24, 2013). "Discovery of a new class of highly potent inhibitors of acid ceramidase: synthesis and structure-activity relationship (SAR)," *J Med Chem* 56(9):3518-3530.

Proksch, D. et al. (2011, e-published Dec. 9, 2010). "Potent inhibition of Acid ceramidase by novel B-13 analogues," *J Lipids* 2011:971618, 8 pages.

Realini, N. et al. (2013, e-published Jan. 8, 2013). "Discovery of highly potent acid ceramidase inhibitors with in vitro tumor chemosensitizing activity," *Sci Rep* 3:1035.

Saied, E.M. et al. (2014, e-published Jun. 16, 2014). "Small molecule inhibitors of ceramidases," *Cell Physiol Biochem* 34(1):197-212.

Salvemini, D. et al. (Feb. 2013, e-published Jan. 12, 2013). "Therapeutic targeting of the ceramide-to-sphingosine 1-phosphate pathway in pain," *Trends Pharmacol Sci* 34(2):11-118.

Stohandl, J. et al. (Jan. 1, 1979). "Study of Solvolysis Mechansim of Some Ureas Derived from 2-Benzoxazolone," Collection of Czechoslovak Chemical Communications, *Institute of Organic Chemistry Biochemistry* 44(6):1790-1798.

Szulc, Z.M .et al. (Jan. 15, 2008, e-published Aug. 24, 2007). "Novel analogs of D-e-MAPP and B13. Part 1: synthesis and evaluation as potential anticancer agents," *Bioorg Med Chem* 16(2):1015-1031.

Timberlake, J.W. et al. (1981). "Thiadiaziridine 1,1-Dioxides: Synthesis and Chemistry," *J Org Chem* 46(10):2082-2089.

Written Opinion dated Jul. 20, 2015, for PCT Application No. PCT/EP2015/060291, filed on May 11, 2015, 6 pages.

Written Opinion dated Jul. 20, 2015, for PCT Application No. PCT/EP2015/060292, filed on May 11, 2015, 6 pages.

Wymann, M.P. et al. (Feb. 2008). "Lipid signalling in disease," *Nat Rev Mol Cell Biol* 9(2):162-176.

Xia, Z. et al. (Feb. 2010, e-published Jan. 6, 2010). "Improved synthesis of a fluorogenic ceramidase substrate," *Bioorg Med Chem* 18(3):1003-1009.

BENZOXAZOLONE DERIVATIVES AS ACID CERAMIDASE INHIBITORS, AND THEIR USE AS MEDICAMENTS

CROSS-REFERENCES TO RELATED APPLICATIONS

This application is a continuation of International Patent Application No. PCT/EP2015/060291, filed May 11, 2015, which claims the benefit of IT Patent Application No. MI2014A000863 filed on May 12, 2014, all of which are incorporated herein by reference in their entirety and for all purposes.

STATEMENT AS TO RIGHTS TO INVENTIONS MADE UNDER FEDERALLY SPONSORED RESEARCH OR DEVELOPMENT

This research was made, in part, with government support under NIH Grant R01 DA12413 awarded by the National Institutes of Health; the United States Government has certain rights in the invention.

FIELD OF THE INVENTION

The present invention relates to acid ceramidase inhibitors and their use as medicaments.

In particular, the present invention concerns acid ceramidase inhibitors, pharmaceutical compositions containing them and methods for preparing these inhibitors.

The present invention also provides methods of inhibiting acid ceramidase for the treatment of cancer, inflammation, pain and inflammatory pain, pulmonary diseases and other disorders in which modulation of the levels of ceramide is clinically relevant.

BACKGROUND OF THE INVENTION

The sphingolipids are a family of membrane lipids derived from the aliphatic amino alcohol sphingosine and its related sphingoid bases. They are present in eukaryote membranes, where they exert important structural roles in the regulation of fluidity and subdomain structure of the lipid bilayer. In addition, they have emerged as key effectors in many aspects of cell biology including inflammation, cell proliferation and migration, senescence and apoptosis [Hannun Y A, Obeid L M. *Principles of bioactive lipid signalling: lessons from sphingolipids. Nat. Rev. Mol. Cell Biol.* 2008, 9, 139-150]. Ceramide is considered a central molecule in sphingolipid catabolism. The generic term "ceramide" comprises a family of several distinct molecular species deriving from the N-acylation of sphingosine with fatty acids of different chain length, typically from 14 to 26 carbon atoms. Ceramide can be synthesized de novo from condensation of serine with palmitate, catalyzed by serine palmitoyltransferase, to form 3-keto-dihydrosphingosine. In turn, 3-keto-dihydrosphingosine is reduced to dihydrosphingosine, followed by acylation by a (dihydro)-ceramide synthase. Ceramide is formed by the desaturation of dihydroceramide. Alternatively, ceramide can be obtained by hydrolysis of sphingomyelin by sphingomyelinases. Ceramide is metabolized by ceramidases to yield sphingosine and fatty acid [Hannun Y A, Obeid L M, *Nat. Rev. Mol. Cell Biol.* 2008, 9, 139-150]. Ceramide plays an important role in a variety of cellular processes. Ceramide concentrations increase in response to cellular stress, such as DNA damage, exposure to cancer chemotherapeutic agents and ionizing radiation, and increased ceramide levels can trigger senescence and apoptosis in normal cells [Wymann M P, Schneiter R. *Lipid signalling in disease. Nat. Rev. Mol. Cell. Biol.* 2008, 9, 162-176]. Moreover, ceramide is also involved in the regulation of cancer cell growth, differentiation, senescence and apoptosis [Morad S and Cabot M. *Ceramide-orchestrated signaling in cancer cells. Nat. Rev. Cancer* 2013, 13, 51-65; Ogretmen B and Hannun Y A. *Biologically active sphingolipids in cancer pathogenesis and treatment. Nat. Rev. Cancer* 2004, 4, 604-616]. Many anticancer drugs increase ceramide levels in cells by stimulating its de novo synthesis and/or hydrolysis of sphingomyelin. For example, daunorubicin elicits ceramide production through the de novo pathway [Bose R et al., *Ceramide synthase mediates daunorubicin-induced apoptosis: an alternative mechanism for generating death signals. Cell* 1995, 82, 405-414]. De novo ceramide induction was observed in various human cancer cells after treatment with camptothecin and fludarabine [Chauvier D et al. *Ceramide involvement in homocamptothecin—and camptothecin induced cytotoxicity and apoptosis in colon HT29 cells. Int. J. Oncol.* 2002, 20, 855-863; Biswal S S et al., *Changes in ceramide and sphingomyelin following fludarabine treatment of human chronic B-cell leukemia cells. Toxicology* 2000, 154, 45-53], and with gemcitabine [Chalfant C E et al., *De novo ceramide regulates the alternative splicing of caspase 9 and Bcl-x in A549 lung adenocarcinoma cells. Dependence on protein phosphatase-1. J. Biol. Chem.* 2002, 277, 12587-12595]. In many of these studies, inhibition of de novo ceramide synthesis was found to prevent, at least in part, the cytotoxic responses to these agents, thus indicating that the de novo pathway might function as a common mediator of cell death. Therefore, increasing or sustaining the levels of ceramide in cancer cells could be envisaged as a novel therapeutic strategy to induce cancer cell death.

One approach to increase or sustain the levels of ceramide in cells is to inhibit the enzymes responsible for ceramide clearance. Enzymes that contribute to decreasing the intracellular levels of ceramide are glucosylceramide synthase, which incorporates ceramide into glucosylceramide, sphingomyelin synthase, which synthesizes sphingomyelin, and ceramidases, which hydrolyze ceramide to sphingosine and fatty acid. Currently, there are five known human ceramidases: acid ceramidase (AC), neutral ceramidase, alkaline ceramidase 1, alkaline ceramidase 2, and alkaline ceramidase 3 [Mao C, Obeid L M. *Ceramidases: regulators of cellular responses mediated by ceramide, sphingosine, and sphingosine-1-phosphate. Biochim. Biophys. Acta* 2008, 1781, 424-434]. Among them, acid ceramidase is emerging as an important enzyme in the progression of cancer and in the response to tumor therapy [Gangoiti P et al., *Control of metabolism and signaling of simple bioactive sphingolipids: Implications in disease. Prog. Lipid Res.* 2010, 49, 316-334]. Messenger RNA and protein levels of acid ceramidase are heightened in a wide variety of cancers including prostate cancer [Seelan R S et al., *Human acid ceramidase is overexpressed but not mutated in prostate cancer. Genes Chromosomes Cancer* 2000, 29, 137-146], head and neck cancer [Norris J S et al., *Combined therapeutic use of AdGFPFasL and small molecule inhibitors of ceramide metabolism in prostate and head and neck cancers: a status report. Cancer Gene Ther.* 2006, 13, 1045-1051; Elojeimy S et al., *Role of acid ceramidase in resistance to FasL: therapeutic approaches based on acid ceramidase inhibitors and FasL gene therapy. Mol. Ther.* 2007, 15, 1259-1263], and melanoma [Musumarra G et al., *A bioinformatic approach to the identification of candidate genes for the* development of new cancer diagnostics. Biol. Chem. 2003, 384, 321-327]. In prostate cancer, acid ceramidase expression correlates with the malignant stage of the disease [Seelan R S et al., *Human acid ceramidase is overexpressed but not mutated in prostate cancer. Genes Chromosomes Cancer* 2000, 29, 137-146]. Up-regulation of acid ceramidase has also been observed in prostate cancer cells in response to radiotherapy, and this mechanism desensitizes cells to both chemotherapy and radiotherapy. Restoration of acid ceramidase levels in radio-resistant cells by either gene silencing or inhibition of acid ceramidase activity confers radiation sensitivity to prostate cancer cells. Improvement of tumor sensitivity to ionizing radiation by inhibition of acid ceramidase has been shown in vivo in a PPC-1 xenograft model [Mahdy A E et al., *Acid ceramidase upregulation in prostate cancer cells confers resistance to radiation: AC inhibition, a potential radiosensitizer. Mol. Ther.* 2009, 5 17, 430-438]. Together, these data suggest that acid ceramidase provides a growth advantage to cancer cells and contributes to the altered balance between proliferation and death eventually leading to tumor progression. Therefore, inhibition of acid ceramidase appears to be a promising strategy for cancer treatment.

The aforementioned balance between cellular proliferation and death is mainly regulated by the ceramide/sphingosine 1-phosphate SIP rheostat [Mao C, Obeid L M. *Ceramidases: regulators of cellular responses mediated by ceramide, sphingosine, and sphingosine-1-phosphate. Biochim. Biophys. Acta* 2008, 1781, 424-434]. Compelling evidences implicate this pathway as contributor to inflammatory conditions and pain of diverse etiologies [Salvemini D, Doyle T, Kress M, Nicol G. *Therapeutic targeting of the ceramide-to-sphingosine 1-phosphate pathway in pain. Trends in Pharmacological Sciences* 2013, 34(2)110-118. Patti G J, Yanes O, Shriver L, Courade J P, Tautenhahn R, Manchester M, Siuzdak G. *Metabolomics implicates altered sphingolipids in chronic pain of neuropathic pain. Nat Chem Biol* 2013, 8(3), 232-234]. Blocking acid ceramidase implies an upstream inhibition of ceramide to sphingosine 1-phosphate S1P pathway and, therefore, seems to be a promising approach to inflammatory and pain conditions treatment.

Certain methods for inhibiting ceramidase activity by compounds containing a sphingoid base, a derivative of a sphingoid base, or a salt of a sphingoid base are described in the EP1287815. Other methods for inhibiting ceramidase activity using cyclopropenyl-sphingosine derivatives are described in WO2005/051891. Still other methods for inhibiting ceramidase activity in cells using cationic ceramide derivatives are reported in WO2006/050264. Further methods for inhibiting or modulating acid ceramidase activity are disclosed in WO2007/136635 and WO2010/054223. Acid ceramidase inhibitors disclosed in the scientific and patent literature, such as B13 [Selzner M et al., *Induction of apoptotic cell death and prevention of tumor growth by ceramide analogues in metastatic human colon cancer. Cancer Res.* 2001, 61, 1233-1240], D-e-MAPP [Bielawska A et al., *(1S,2R)-D-Erythro-2-(N-myristolamino)-1-phenyl-1-propanol as an inhibitor of ceramidase. J. Biol. Chem.* 1996, 271, 12646-12654], B13 and D-MAPP analogues [Proksch et al., *Potent Inhibition of Acid Ceramidase by Novel B-13 Analogues, J. Lipids*, Article ID 971618, 8 pages; Bielawska A et al., *Novel analogs of D-e-MAPP and B13. Part 2: Signature effects on bioactive sphingolipids, Bioorg. Med. Chem.* 2008, 16, 1032-1045; Szulc Z et al., *Novel analogs of D-e-MAPP and B13. Part 1: Synthesis and evaluation as potential anticancer agents. Bioorg. Med. Chem.* 2008, 16, 1015-1031; Bhabak K P and Arenz C, *Novel amide- and sulfonamide-based aromatic ethanolamines: Effects of various substituents on the inhibition of acid and neutral ceramidases, Bioorg. Med. Chem.* 2012, 20, 6162-6170], oleoylethanolamides such as NOE and NOE analogues [Grijalvo S et al., *Design, synthesis and activity as acid ceramidase inhibitors of 2-oxooctanoyl and N-oleoylethanolamine analogues, Chem. Phys. Lipids* 2006, 144, 69-84], LCL-204 [Holman D H et al., *Lysosomotropic acid ceramidase inhibitor induces apoptosis in prostate cancer cells. Cancer Chemother. Pharmacol.* 2008, 61, 231-242], LCL-464 and analogues [Bai A et al., *Synthesis and bioevaluation of omega-N amino analogs of B13, Bioorg. Med. Chem.* 2009, 17, 1840-1848; Bhabak K P et al., *Effective inhibition of acid and neutral ceramidases by novel B-13 and LCL-464 analogues, Bioorg. Med. Chem.* 2013, 21, 874-882], or E-tb [Bedia C et al., *Cytotoxicity and acid ceramidase inhibitory activity of 2-substituted aminoethanol amides. Chem. Phys. Lipids* 2008, 156, 33-40] are ceramide analogs that inhibit acid ceramidase activity in cell-free assays and proliferation of cancer cell lines only at high micromolar concentrations.

However, recently, two different small-molecule chemotypes were reported to be acid ceramidase inhibitors—quinolinones [Draper J M et al., *Discovery and Evaluation of Inhibitors of Human Ceramidase, Mol. Cancer Ther.* 2011, 10, 2052-2061] and 2,4-dioxopyrimidine-1-carboxamides [Realini N et al., *Discovery of highly potent acid ceramidase inhibitors with in vitro tumor chemosensitizing activity, Sci. Rep.* 2013, 3, 1035; Pizzirani D et al., *Discovery of a New Class of Highly Potent Inhibitors of Acid Ceramidase: Synthesis and Structure-Activity Relationship (SAR), J. Med. Chem.* 2013, 56, 3518-3530] that have been claimed in WO2013/178545 and WO2013/178576.

Although both series showed effects in vitro and in vivo, they may suffer from developability issues; therefore, there is a substantial need for novel acid ceramidase inhibitors with improved potency and drug-likeness, in particular selectivity over related proteins and intrinsic stability.

Certain benzoxazolonyl ureas are claimed in FR1469297 for their fungicide, herbicide and pesticide properties and, more in general, as disinfectants of general use. Other benzoxazolones containing the urea moiety and their compositions are claimed in FR2478635 as fungicides and bactericides for non medical use.

Finally, U.S. Pat. No. 7,709,513B2 discloses benzoxazol-2-one derivatives as lipase and phospholipase inhibitors. This reference only discloses that certain benzoxazol-2-one derivatives are active in metabolic diseases such as atherosclerosis and dyslipidemia and merely claims the treatment of insulin resistance and diabetes mellitus.

SUMMARY OF THE INVENTION

Accordingly, one of the aims of the present invention resides in the provision of acid ceramidase (AC) inhibitors featuring the benzoxazolone urea scaffold for use in the prevention or treatment of cancer, inflammation, pain and inflammatory pain, pulmonary diseases, specifically in the forms in which the modulation of ceramide levels is clinically relevant.

The inventors have found that specific benzoxazolone derivatives that selectively inhibit acid ceramidase display an antiproliferative profile that makes them uniquely suitable to treat diseases characterized by abnormal cell proliferation, including but not limited to cancer, psoriasis and rheumatoid arthritis.

In a first aspect, the present invention provides a compound of Formula (I) or a pharmaceutically acceptable salt thereof for use in the treatment of cancer, inflammation, pain and inflammatory pain, pulmonary diseases

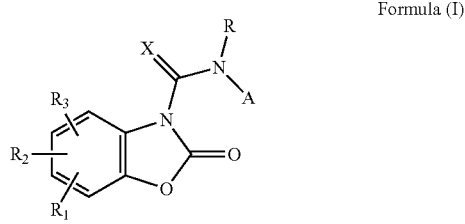

Formula (I)

wherein A, R, $R_1$, $R_2$, $R_3$, X are as defined below or in the appended claims.

In a second aspect the present invention provides a compound having Formula (Ia) or a pharmaceutically acceptable salt thereof

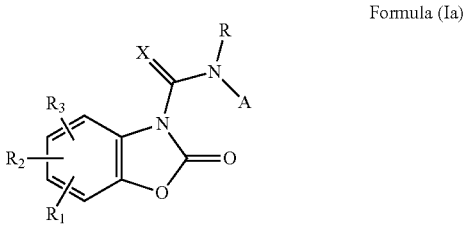

Formula (Ia)

wherein A, R, $R_1$, $R_2$, $R_3$, X are as defined below or in the appended claims.

In a third aspect, the present invention provides a pharmaceutical composition comprising one or more compounds of Formula (I) or (Ia) as defined above or a pharmaceutically acceptable salt thereof, and pharmaceutically acceptable excipients, carriers or diluents for use in the treatment of cancer, inflammation, pain and inflammatory pain, pulmonary diseases.

In a fourth aspect, the present invention provides a method of treatment of diseases or disorders associated with increased (relative to physiological or desired) levels of acid ceramidase protein or function, for example in subjects where acid ceramidase is overactive or over-expressed, by administering a therapeutically effective amount of a compound of Formula (I) or (Ia) as defined above or a pharmaceutically acceptable salt thereof, according to the invention.

In some embodiments, the compounds of Formula (I) or (Ia) and their pharmaceutical compositions and methods of administering them, are useful in treating diseases or disorders involving abnormal cell proliferation and/or dysfunctional sphingolipid signal transduction. These diseases and disorders include, but are not limited to, primary and metastatic neoplastic diseases.

In a fourth aspect, the present invention provides methods for preparing the compounds of Formula (I) or (Ia) as defined above, through a process consisting of suitable synthetic transformations.

In a fifth aspect, the present invention provides biological in vitro methods for testing the compounds of Formula (I) or (Ia) therefore assessing their therapeutic potential.

BRIEF DESCRIPTION OF THE DRAWINGS

FIG. 7 illustrates the effects of compound of Example 25 or vehicle (15% polyethylene glycol, 15% Tween80, 70% saline) on AC activity in mouse lungs (oral administration, A) or cerebral cortex (intraperitoneal administration, B) and on ceramide levels (C and D). Results are expressed as mean±s.e.m. (n=6). *p<0.05, p<0.01, *p<0.001 vs vehicle, one-way ANOVA followed by Dunnet.

DETAILED DESCRIPTION OF THE INVENTION

Figure 1:
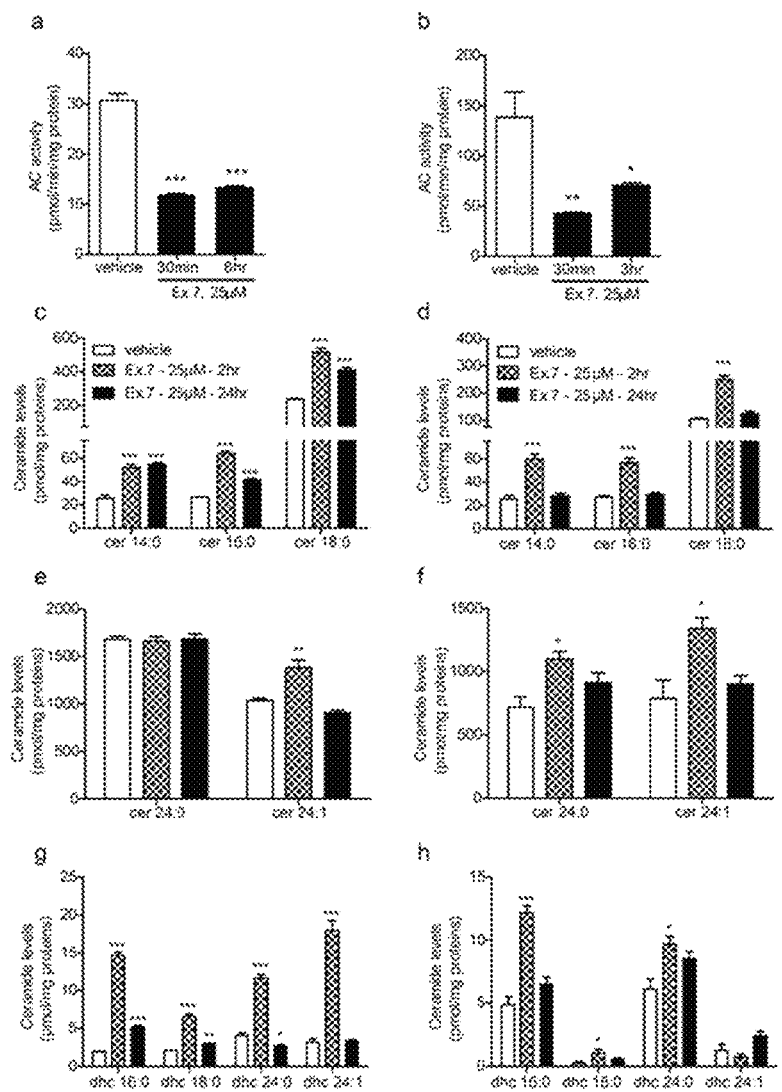
FIG. 1 shows six bar graphs illustrating the effects of compound of Example 7 on AC activity and ceramide levels in two different human melanoma cell lines. Specifically, FIG. 1 evidences the effects of compound of Example 7 or vehicle (0.1% DMSO in DMEM) on AC activity and ceramide levels in A375 (left panel) or MeWo (right panel) human melanoma cell lines. (A-B) Intact cells were treated with compound of Example 7 (25 μM) or vehicle and AC activity was measured 30 minutes or 3 hours later in cell lysates. (B) Intact cells were exposed to compound of Example 7 (25 μM) for 2 hours or 24 hours and medium chain ceramides (C-D), long chain ceramides (E-F) and dihydroceramides (G-H) were quantified. Results are expressed as mean±s.e.m. (n=3). *p<0.05, p<0.01, *p<0.001 vs vehicle, two-way ANOVA followed by Dunnet.

In a first aspect, the present invention provides a compound of Formula (I) or a pharmaceutically acceptable salt thereof for use in the treatment of cancer, inflammation, pain and inflammatory pain, pulmonary diseases

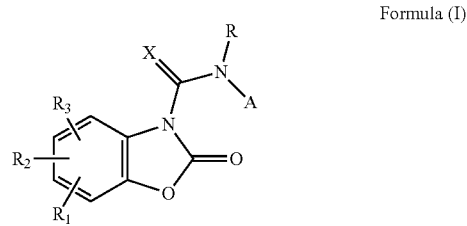

Formula (I)

wherein:
X is O or S;
R is hydrogen, linear or branched $C_{1-6}$ alkyl;
A is a linear or branched $C_{5-12}$ alkyl group or a group:

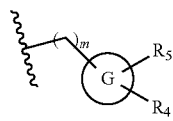

wherein:
m is an integer from 1 to 6;
G is a 3-10 membered saturated or unsaturated, aromatic or heteroaromatic, single or fused ring comprising up to three heteroatoms selected from N, O, S; and $R_4$ and $R_5$ are as defined below;
$R_1$, $R_2$, $R_3$, $R_4$ and $R_5$, are independently selected from the group consisting of hydrogen, halogen, linear or branched $C_{1-6}$ alkyl, optionally substituted cycloalkyl $C_{1-6}$ alkyl, optionally substituted cycloalkyl $C_{2-6}$ alkenyl, optionally substituted aryl $C_{1-6}$ alkyl, optionally substituted aryl $C_{1-6}$ alkyenyl, $C_{1-6}$ alkoxy, optionally substituted cycloalkyl $C_{1-6}$ alkoxy, optionally substituted aryl $C_{1-6}$ alkoxy, hydroxy $C_{1-6}$ alkyl, OH, CN, $NO_2$, fluoro $C_{1-6}$ alkyl, fluoro $C_{1-6}$ alkoxy, optionally substituted aryl, $C_{1-6}$ alkylCO, optionally substituted arylCO, optionally substituted aryl $C_{1-6}$ alkylCO, $COOR_7$, $CONR_8R_9$, $SO_2R_{10}$ where $R_7$, $R_8$, $R_9$ and $R_{10}$ are independently selected from the group consisting of hydrogen, linear or branched $C_{1-6}$ alkyl; $R_1$, $R_2$, $R_3$, $R_4$ and $R_5$ can be attached to any position of the ring to which they are connected.

In accordance with certain embodiments, a compound of Formula (I) or pharmaceutically acceptable salt thereof is provided for use in the treatment of cancer, inflammation, pain and inflammatory pain, pulmonary diseases wherein:
X is O or S;
R is hydrogen or a linear or branched $C_{1-6}$ alkyl,
A is a linear or branched $C_{5-12}$ alkyl group or a group

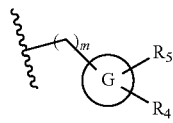

wherein:
m is an integer from 1 to 6;
G is an optionally substituted $C_3$-$C_{10}$ cycloalkyl which is cyclopropane, cyclobutane, cyclopentane, cyclopentene, cyclohexane, cyclohexene, cyclohexadiene, or cycloheptane;
an optionally substituted aryl which is phenyl, alpha- or beta-naphthyl, 9,10-dihydroanthracenyl, indanyl, fluorenyl or biphenyl;
an optionally substituted heteroaryl which is pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, thienyl, pyridyl, pyrazinyl, pyrimidinyl, pyridazinyl, quinolinyl, isoquinolinyl, quinazolinyl or quinoxalinyl;
an optionally substituted heterocyclic ring which is oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, thiazoline, isothiazoline, dioxane, piperazine, morpholine, thiomorpholine, hexamethyleneimine or homopiperazine;
$R_1$, $R_2$, $R_3$, $R_4$ and $R_5$, are independently selected from hydrogen, halogen, linear or branched $C_{1-6}$ alkyl, optionally substituted cycloalkyl $C_{1-6}$ alkyl, optionally substituted cycloalkyl $C_{2-6}$ alkenyl, optionally substituted aryl $C_{1-6}$ alkyl, optionally substituted aryl $C_{2-6}$ alkyenyl, $C_{1-6}$ alkoxy, optionally substituted cycloalkyl $C_{1-6}$ alkoxy, optionally substituted aryl $C_{1-6}$ alkoxy, hydroxy $C_{1-6}$ alkyl, OH, CN, $NO_2$, fluoro $C_{1-6}$ alkyl, fluoro $C_{1-6}$ alkoxy; optionally substituted aryl, $C_{1-6}$ alkylCO, optionally substituted arylCO, optionally substituted aryl $C_{1-6}$ alkylCO, $COOR_7$, $CONR_8R_9$, $SO_2R_{10}$ where $R_7$, $R_8$, $R_9$ and $R_{10}$ are independently selected from the group consisting of hydrogen, linear or branched $C_{1-6}$ alkyl; $R_1$, $R_2$, $R_3$, $R_4$ and $R_5$ can be attached to any position of the ring to which they are connected.

In certain embodiments a compound of the above Formula (I) or pharmaceutically acceptable salt thereof is provided for use in the treatment of cancer, inflammation, pain and inflammatory pain, pulmonary diseases wherein:
X is O or S;
R is hydrogen or a linear or branched $C_{1-6}$ alkyl,
A is a linear or branched $C_{5-9}$ alkyl group or a group

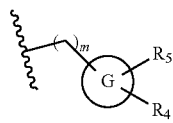

wherein:
m is an integer from 1 to 6;
G is
an aryl selected from naphthyl or phenyl
$(C_3-C_{10})$cycloalkyl,
a heteroaryl which is pyridyl, tiophenyl, pyrimidinyl, furyl, indolyl
wherein $R_4$ and $R_5$, if present, independently are halogen, $NO_2$, $(C_1-C_3)$alkoxy-,$(C_3-C_{10})$ cycloalkyl, linear or branched $C_1-C_6$ alkyl; $R_4$ and $R_5$ can be attached to any position of the ring to which they are connected,
$R_1$, $R_2$, $R_3$, are independently hydrogen, halogen, linear or branched $C_{1-6}$ alkyl, OH, CN, $NO_2$, fluoro $C_{1-6}$ alkyl, hydroxy $C_{1-6}$ alkyl,
phenyl optionally substituted with $C_1-C_6$ alkyl, $C_1-C_3$ alkoxy, $C_2-C_6$ alkenyl, halogen, $NO_2$, $CF_3$ phenyl $C_{1-6}$ alkyl optionally substituted with $C_1-C_6$ alkyl, $C_1-C_3$ alkoxy, $C_2-C_6$ alkenyl, halogen, $NO_2$, $CF_3$
phenyl $C_{2-6}$ alkenyl optionally substituted with $C_1-C_6$ alkyl, $C_1-C_3$ alkoxy, $C_2-C_6$ alkenyl, halogen, $NO_2$, $CF_3$;
phenyl CO optionally substituted with $C_1-C_6$ alkyl, $C_1-C_3$ alkoxy, $C_2-C_6$ alkenyl, halogen, $NO_2$, $CF_3$ $C_1-C_6$ alkyl CO optionally substituted with phenyl, optionally substituted with $C_1-C_6$ alkyl, $C_1-C_3$ a alkoxy, $C_2-C_6$ alkenyl, halogen, $NO_2$, $CF_3$;
$(C_3-C_{10})$cycloalkyl $C_{1-6}$ alkyl optionally substituted with $C_1-C_6$ alkyl, $C_2-C_6$ alkenyl, halogen,
$(C_3-C_{10})$cycloalkyl $C_{2-6}$ alkenyl optionally substituted with $C_1-C_6$ alkyl, $C_2-C_6$ alkenyl, halogen
$C_{1-6}$ alkoxy optionally substituted with halogen, $(C_3-C_{10})$ cycloalkyl, phenyl,
$R_1$, $R_2$, $R_3$, can be attached to any position of the ring to which they are connected.

In accordance with certain embodiments a compound of the above Formula (I) is provided for use in the treatment of cancer, inflammation, pain and inflammatory pain, pulmonary diseases wherein
X is O;
R is hydrogen;
A is a linear or branched $C_{5-9}$ alkyl group or preferably a group

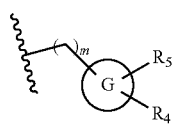

wherein:
m is an integer from 1 to 4;
G is phenyl, thiophenyl, pyridyl, naphthyl or $C_{3-7}$ cycloalkyl, preferably cyclohexyl;
$R_1$, $R_2$, $R_3$, $R_4$ and $R_5$, are, independently, H, F, Cl, Br, Me, Et, Pr, MeO, BuO, OH, CN, $NO_2$, $CF_3$. Ph, MeCO, EtCO;
wherein $R_1$, $R_2$, $R_3$, $R_4$ and $R_5$ can be attached to any position of the ring to which they are connected.

In accordance with a second aspect of the present invention compounds of Formula (Ia) or acceptable salts thereof are provided wherein

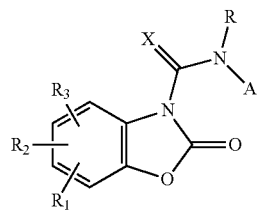

Formula (Ia)

Wherein:
X is O or S;
R is hydrogen, linear or branched $C_{1-6}$ alkyl;
A is a linear or branched $C_{5-12}$ alkyl group or a group:

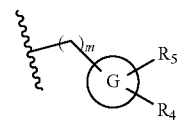

wherein:
m is an integer from 1 to 6;
G is a 3-10 membered saturated or unsaturated, aromatic or heteroaromatic, single or fused ring comprising up to three heteroatoms selected from N, O, S; and $R_4$ and $R_5$ are as defined below;
$R_1$, $R_2$, $R_3$, $R_4$ and $R_5$, are independently selected from the group consisting of hydrogen, halogen, linear or branched $C_{1-6}$ alkyl, optionally substituted cycloalkyl $C_{1-6}$ alkyl, optionally substituted cycloalkyl $C_{2-6}$ alkenyl, optionally substituted aryl $C_{1-6}$ alkyl, optionally substituted aryl $C_{2-6}$ alkyenyl, optionally substituted cycloalkyl $C_{1-6}$ alkoxy, optionally substituted aryl $C_{1-6}$ alkoxy, hydroxy $C_{1-6}$ alkyl, OH, fluoro $C_{1-6}$ alkyl, fluoro $C_{1-6}$ alkoxy, substituted aryl, optionally substituted arylCO, optionally substituted aryl $C_{1-6}$ alkylCO,
wherein $R_1$, $R_2$, $R_3$, $R_4$ and $R_5$ can be attached to any position of the ring to which they are connected,
with the proviso that
at least one amongst $R_1$, $R_2$ and $R_3$ is different from hydrogen, halogen and alkyl and
when m is 1 and $R_4$ and $R_5$ are both hydrogen, or one is hydrogen and the other is methyl, then G is not a benzene ring.

In accordance with certain embodiments, compounds of Formula (Ia) are provided wherein:
X is O or S;
R is hydrogen;
A is a linear or branched $C_{5-9}$ alkyl group or preferably a group:

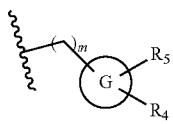

wherein:

m is an integer from 3 to 6, preferably 4 to 6

G is phenyl, thienyl, pyridyl, naphthyl or $C_{3-7}$ cycloalkyl, preferably cyclohexyl;

$R_1$, $R_2$, $R_3$, $R_4$ and $R_5$ are independently selected from the group consisting of hydrogen, optionally substituted cyclohexylethyl, optionally substituted cyclohexylethenyl, optionally substituted phenylethyl, optionally substituted phenylethenyl, optionally substituted cyclohexylethoxy, optionally substituted phenylethoxy, $HOCH_2$, $CF_2H$, $CFH_2$, $CF_3CF_2$, $CF_3O$, $CF_3CF_2O$, substituted phenyl, optionally substituted phenylCO, optionally substituted phenyl$C_{1-6}$alkylCO, $R_1$, $R_2$, $R_3$, $R_4$ and $R_5$ can be attached to any position of the ring to which they are connected, with the proviso that at least one amongst $R_1$, $R_2$ and $R_3$ is different from hydrogen.

Preferred compounds of Formula (Ia) are those in which A is a group:

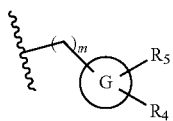

wherein G, $R_4$, $R_5$ and m are as defined above.

All technical and scientific terms used herein have the same meaning as commonly understood by a person of ordinary skill in the art, unless otherwise defined. The following terms, used in the specification and claims of this application, have the meaning specified hereunder, unless otherwise defined.

I. Definitions

The term "alkyl", as used herein, indicates a saturated aliphatic hydrocarbon radical, including straight chain and branched chain radicals of 1 to 6 carbon atoms. Non-limiting examples of alkyl are, for instance, methyl, ethyl, propyl, isopropyl, n-butyl, iso-butyl, tert-butyl, n-amyl, iso-amyl, n-hexyl, and the like. The term Me, as used herein, means a methyl group, similarly the term Et means the ethyl group.

The term "alkenyl", as used herein, indicates an alkyl group, as defined herein, consisting of at least two carbon atoms and containing at least one carbon-carbon double bond. Representative examples include, but are not limited to, ethenyl, 1-propenyl, 2-propenyl, 1- or 2-butenyl, and the like.

The term "alkynyl", as used herein, indicates an alkyl group, as defined herein, consisting of at least two carbon atoms and containing at least one carbon-carbon triple bond. Representative examples include, but are not limited to, ethynyl, 1-propynyl, 2-propynyl, 1- or 2-butynyl, and the like.

The term "cycloakyl", as used herein, indicates a 3- to 7-membered all-carbon monocyclic ring, which may contain one or more double bonds but does not have a completely conjugated pi-electron system. Examples of cycloalkyl groups include, without limitation, cyclopropane, cyclobutane, cyclopentane, cyclopentene, cyclohexane, cyclohexene, cyclohexadiene, and cycloheptane.

The term "aryl", as used herein, indicates a hydrocarbon consisting of a mono-, bi- or tricyclic ring system, wherein the rings are fused together or linked to each other covalently and at least one of the carbocyclic ring is aromatic. The term "aryl" means a cyclic aromatic such as a 6-membered hydrocarbon, a two six-membered fused hydrocarbon, and a two six-membered hydrocarbon covalently bonded. Examples of aryl groups include phenyl, alpha- or beta-naphthyl, 9,10-dihydroanthracenyl, indanyl, fluorenyl, biphenyl and the like.

The term "heteroaryl", as used herein, indicates a mono-, bi- or tricyclic ring system containing from one to four heteroatoms selected from nitrogen, oxygen and sulphur, wherein the rings are fused together or linked to each other covalently and at least one of the rings is aromatic. Examples of heteroaryl groups include pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl.

The terms "heterocyclyl" or "heterocyclic ring", as used herein mean a 3- to 7-membered, saturated or partially unsaturated carbocyclic ring wherein one or more carbon atoms are independently replaced by nitrogen, oxygen or sulfur. The heteroatom nitrogen and sulfur are optionally oxidized, and the nitrogen atom(s) are optionally quaternized. Examples of heterocyclyl groups include, for instance, radicals derived from oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, thiazoline, isothiazoline, dioxane, piperazine, morpholine, thiomorpholine, examethyleneimine, homopiperazine, and the like.

The term "aromatic" refers to a moiety wherein the constituent atoms make up an unsaturated ring system, all atoms in the ring system are $sp^2$ hybridized and the total number of pi electrons is equal to $4n+2$, wherein n is an integer.

Any of the above mentioned alkyl, alkenyl, alkynyl, cycloalkyl, aryl, heteroaryl, heterocyclyl or heterocyclic ring group may be unsubstituted or substituted by one or more substituents.

Unless otherwise indicated, the term "substituted" as used herein means that one or more hydrogen atoms of the above mentioned groups are replaced with another atom or functional group including, by way of example, alkyl, substituted alkyl, aryl, substituted aryl, arylalkyl, alkoxy, cycloalkyloxy, aryloxy, arylalkyloxy, hydroxy, heteroaryl, heteroaryloxy, heterocyclyloxy, trifluoromethyl, trifluoromethoxy, carboxy, acyl, aroyl, heteroaroyl, halogen, nitro, cyano, alkoxycarbonyl, aryloxycarbonyl, a ralkyloxycarbonyl, cycloalkyloxycarbonyl, heteroaryloxycarbonyl, acyloxy, alkylthio, arylthio, alkylsulfinyl, arylsulfinyl, alkylsulfonyl, arylsulfonyl, —O-aroyl, —O-heteroaroyl, oxo (=O), —C(=O)—$NR^hR^k$, and —$NR^pR^q$, wherein each of $R^h$, $R^k$, $R^p$, and $R^q$ independently represents hydrogen, unsubstituted or substituted alkyl, unsubstituted or substituted cycloalkyl, unsubstituted or substituted aryl, unsubstituted or substituted arylalkyl, unsubstituted or substituted heteroaryl, unsubstituted or substituted heterocyclyl, acyl, aroyl, heteroaroyl, and when $R^h$ and $R^k$, or $R^p$ and $R^q$ are taken together with the nitrogen atom to which they are bound, the group —$NR^hR^k$ or the group NR$^p$R$^q$ represent a heterocyclyl residue and wherein the terms alkyl, cycloalkyl, aryl, heteroaryl, heterocyclyl are as above defined.

The term "alkoxy", as used herein, means an unsubstituted or substituted alkyl chain linked to the remainder of the molecule through an oxygen atom. Examples of alkoxy include, but are not limited to, methoxy, ethoxy, propyloxy, isopropyloxy, benzyloxy and the like. The term MeO means methoxy, the term EtO means ethoxy.

The term "halogen", as used herein, indicates fluorine (F), chlorine (Cl), bromine (Br) or iodine (I).

The term "hydroxy" means a —OH radical.

The term "trifluoromethyl" means a —CF$_3$ radical.

The term "trifluoromethoxy" means a —OCF$_3$ radical.

Examples of compounds of the invention, as reported in the following Table 1, are:

2-oxo-N-(4-phenylbutyl)-1,3-benzoxazole-3-carboxamide
5-fluoro-2-oxo-N-(4-phenylbutyl)-1,3-benzoxazole-3-carboxamide
6-fluoro-2-oxo-N-(4-phenylbutyl)-1,3-benzoxazole-3-carboxamide
5-chloro-2-oxo-N-(4-phenylbutyl)-1,3-benzoxazole-3-carboxamide
6-chloro-2-oxo-N-(4-phenylbutyl)-1,3-benzoxazole-3-carboxamide
5-bromo-2-oxo-N-(4-phenylbutyl)-1,3-benzoxazole-3-carboxamide
6-bromo-2-oxo-N-(4-phenylbutyl)-1,3-benzoxazole-3-carboxamide
5-methyl-2-oxo-N-(4-phenylbutyl)-1,3-benzoxazole-3-carboxamide
6-methyl-2-oxo-N-(4-phenylbutyl)-1,3-benzoxazole-3-carboxamide
6-methoxy-2-oxo-N-(4-phenylbutyl)-1,3-benzoxazole-3-carboxamide
5-nitro-2-oxo-N-(4-phenylbutyl)-1,3-benzoxazole-3-carboxamide
6-nitro-2-oxo-N-(4-phenylbutyl)-1,3-benzoxazole-3-carboxamide
2-oxo-N-(4-phenylbutyl)-5-(trifluoromethyl)-1,3-benzoxazole-3-carboxamide
2-oxo-N-(4-phenylbutyl)-6-(trifluoromethyl)-1,3-benzoxazole-3-carboxamide
5-cyano-2-oxo-N-(4-phenylbutyl)-1,3-benzoxazole-3-carboxamide
5,6-dichloro-2-oxo-N-(4-phenylbutyl)-1,3-benzoxazole-3-carboxamide
4-methyl-2-oxo-N-(4-phenylbutyl)-1,3-benzoxazole-3-carboxamide
7-methyl-2-oxo-N-(4-phenylbutyl)-1,3-benzoxazole-3-carboxamide
7-bromo-2-oxo-N-(4-phenylbutyl)-1,3-benzoxazole-3-carboxamide
2-oxo-5-phenyl-N-(4-phenylbutyl)-1,3-benzoxazole-3-carboxamide
5-(4-methoxyphenyl)-2-oxo-N-(4-phenylbutyl)-1,3-benzoxazole-3-carboxamide (Formula Ia)
5-(4-fluorophenyl)-2-oxo-N-(4-phenylbutyl)-1,3-benzoxazole-3-carboxamide (Formula Ia)
2-oxo-6-phenyl-N-(4-phenylbutyl)-1,3-benzoxazole-3-carboxamide
6-(4-methoxyphenyl)-2-oxo-N-(4-phenylbutyl)-1,3-benzoxazole-3-carboxamide (Formula Ia)
6-(4-fluorophenyl)-2-oxo-N-(4-phenylbutyl)-1,3-benzoxazole-3-carboxamide (Formula Ia)
2-oxo-4-phenyl-N-(4-phenylbutyl)-1,3-benzoxazole-3-carboxamide
2-oxo-7-phenyl-N-(4-phenylbutyl)-1,3-benzoxazole-3-carboxamide
2-oxo-N-(4-phenylbutyl)-6-[(E)-styryl]-1,3-benzoxazole-3-carboxamide (Formula Ia)
6-[(E)-2-cyclohexylvinyl]-2-oxo-N-(4-phenylbutyl)-1,3-benzoxazole-3-carboxamide (Formula Ia)
2-oxo-6-phenethyl-N-(4-phenylbutyl)-1,3-benzoxazole-3-carboxamide (Formula Ia)
6-(2-cyclohexylethyl)-2-oxo-N-(4-phenylbutyl)-1,3-benzoxazole-3-carboxamide (Formula Ia)
6-butoxy-2-oxo-N-(4-phenylbutyl)-1,3-benzoxazole-3-carboxamide
6-(2-cyclohexylethoxy)-2-oxo-N-(4-phenylbutyl)-1,3-benzoxazole-3-carboxamide (Formula Ia)
2-oxo-6-phenethyloxy-N-(4-phenylbutyl)-1,3-benzoxazole-3-carboxamide (Formula Ia)
6-hydroxy-2-oxo-N-(4-phenylbutyl)-1,3-benzoxazole-3-carboxamide
2-oxo-N-(4-phenylbutyl)-6-propanoyl-1,3-benzoxazole-3-carboxamide
6-benzoyl-2-oxo-N-(4-phenylbutyl)-1,3-benzoxazole-3-carboxamide (Formula Ia)
6-(4-chlorobenzoyl)-2-oxo-N-(4-phenylbutyl)-1,3-benzoxazole-3-carboxamide (Formula Ia)
N-(4-cyclohexylbutyl)-2-oxo-1,3-benzoxazole-3-carboxamide
2-oxo-N-[(4-propylcyclohexyl)methyl]-1,3-benzoxazole-3-carboxamide
2-oxo-N-[(4-propylphenyl)methyl]-1,3-benzoxazole-3-carboxamide
N-octyl-2-oxo-1,3-benzoxazole-3-carboxamide
2-oxo-N-(3-phenylpropyl)-1,3-benzoxazole-3-carboxamide
2-oxo-N-[4-(2-thienyl)butyl]-1,3-benzoxazole-3-carboxamide
N-[4-(4-methoxyphenyl)butyl]-2-oxo-1,3-benzoxazole-3-carboxamide
N-[4-(4-fluorophenyl)butyl]-2-oxo-1,3-benzoxazole-3-carboxamide
2-oxo-N-[4-(p-tolyl)butyl]-1,3-benzoxazole-3-carboxamide
N-[4-(4-nitrophenyl)butyl]-2-oxo-1,3-benzoxazole-3-carboxamide (Formula Ia)
2-oxo-N-[3-(3-pyridyl)propyl]-1,3-benzoxazole-3-carboxamide
N-[3-(3-fluorophenyl)propyl]-2-oxo-1,3-benzoxazole-3-carboxamide
N-[3-(2-chlorophenyl)propyl]-2-oxo-1,3-benzoxazole-3-carboxamide
N-[4-(2-naphthyl)butyl]-2-oxo-1,3-benzoxazole-3-carboxamide
N-hexyl-2-oxo-1,3-benzoxazole-3-carbothioamide (Formula Ia)
2-oxo-N-(4-phenylbutyl)-1,3-benzoxazole-3-carbothioamide (Formula Ia)
N-methyl-2-oxo-N-(4-phenylbutyl)-1,3-benzoxazole-3-carboxamide
4-fluoro-2-oxo-N-(4-phenylbutyl)-1,3-benzoxazole-3-carboxamide
2-oxo-N-(5-phenylpentyl)-1,3-benzoxazole-3-carboxamide (Formula Ia)
2-oxo-N-(6-phenylhexyl)-1,3-benzoxazole-3-carboxamide (Formula Ia)
N-heptyl-2-oxo-1,3-benzoxazole-3-carboxamide.

II. Methods for Preparing Compounds of Formula (I), (Ia)

In another aspect, the present invention also provides methods for preparing the compounds of Formula (I), (Ia) as defined above, through a process consisting of suitable synthetic transformations reported, for instance, in Michael Smith, Jerry March—*March's Advanced Organic Chemistry: reactions mechanisms and structure*—*6th Edition*, John Wiley & Sons Inc., 2007, which is herein incorporated as reference. It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—*Protective Groups in Organic Synthesis, Fourth Edition*, John Wiley & Sons Inc., 2006, which is herein incorporated as reference.

In one embodiment, a compound of Formula (I), (Ia) can be obtained by application of the chemical transformations reported in Scheme 1 described below.

Synthesis of Compounds of Formula (I), (Ia):

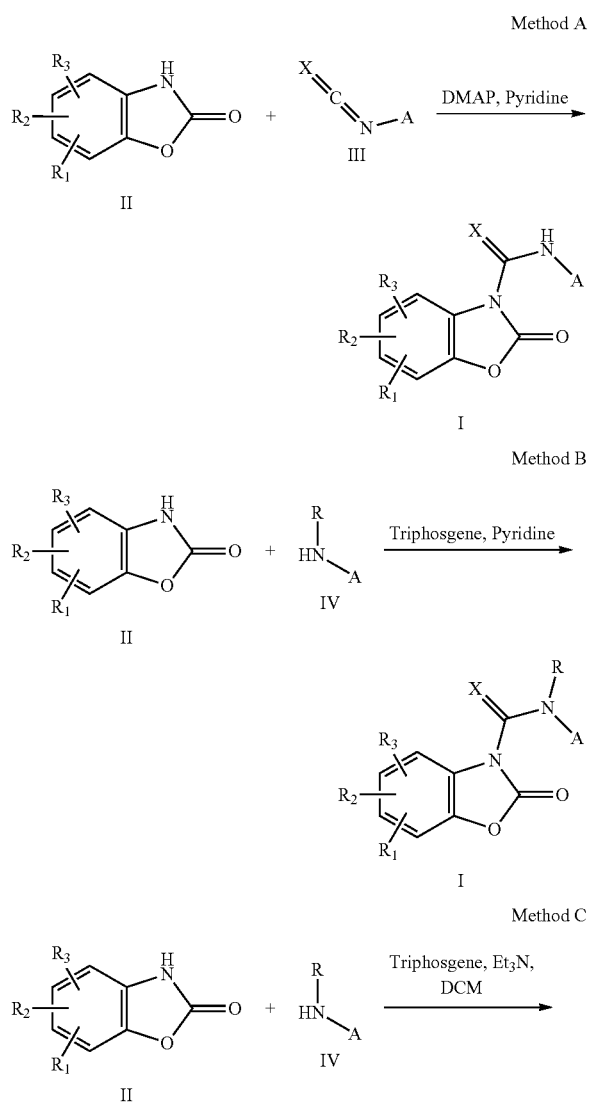

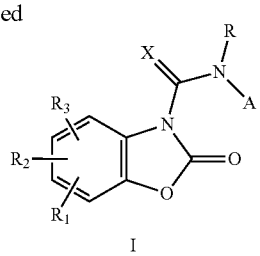

In certain embodiments, a compound of Formula (I), (Ia), where R is hydrogen, can be obtained by Method A (Scheme 1), where an optionally substituted benzoxazol-2-one of Formula II, or a salt thereof, is reacted with an isocyanate (X═O) or thioisocyanate (X═S) of Formula III, wherein A, $R_1$, $R_2$, $R_3$, are as defined above. Isocyanates or thioisocyanates of Formula III are either commercially available or can be prepared by synthetic methods as reported, for instance, in Molina P., Tarraga A., Arques A. in Katritzky A. R., Taylor R. J. k., *Comprehensive Organic Functional Group Trasformations II*, Elsevier, 2004, Vol. 5, Pag. 949-973; or in Michael Smith, Jerry March—*March's Advanced Organic Chemistry: reaction mechanisms and structure—6th Edition*, John Wiley & Sons Inc., 2007, and references cited therein, which are incorporated herein as reference.

In other embodiments, a compound of Formula (I), (Ia), where X is oxygen, can be obtained by Method B or Method C (Scheme 1), where an optionally substituted benzoxazol-2-one of Formula II, or a salt thereof, is reacted with an amine of Formula IV, or salt thereof, wherein A, R, $R_1$, $R_2$ and $R_3$ are as defined above. Triphosgene is here used to activate the nitrogen of benxoxazol-2-ones of Formula II, thereby making it amenable to react with amines of Formula IV to form the final compounds of Formula (I), (Ia).

Similar to Method B and C, a compound of Formula (I), (Ia), as defined above, can be prepared by treating compounds of Formula II (as defined in Scheme 1, Method B-C) with an activating agent such as phosgene, ethyl chloroformate, p-nitrophenylchloroformate, 1,1'-carbonyldiimidazole, and the like, and subsequent reaction with an amine of Formula IV, as defined above. Such reaction is carried out in a so-called "one-pot" procedure, in a suitable solvent such as dichloromethane, chloroform, acetonitrile, tetrahydrofuran, pyridine, or mixtures thereof, and in the presence of a suitable base such as triethylamine, diisopropylethylamine, or pyridine, at a temperature ranging from −10° C. to 40° C., and for a period of time from 15 minutes to 72 hours.

Synthesis of Compounds of Formula (II):

Compounds of Formula II are either commercially available or can be prepared according to standard synthetic methods as reported, for instance, in Michael Smith, Jerry March—*March's Advanced Organic Chemistry: reaction mechanisms and structure—6th Edition*, John Wiley & Sons Inc., 2007.

Scheme 2a

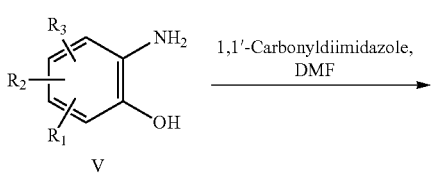

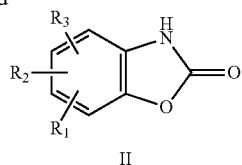

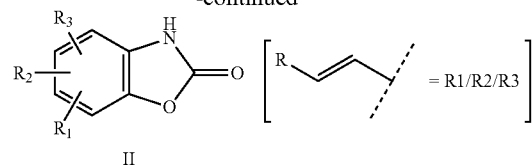

Benzoxazol-2-ones of Formula II can be obtained from the appropriate 2-aminophenol of Formula V (Scheme 2a) by an intramolecular cyclization reaction in the presence of 1,1'-carbonyldiimidazole (Scheme 2a), as described in literature (Nachman R J, *J. Heterocyclic Chem.*, 1982, 19, 1545-1547; Moon J-K et al., *J. Agric. Food Chem.* 2010, 58, 12357-12365), which is incorporated herein as reference. Also, other reagents can be used instead of 1,1'-carbonyldiimidazole, e.g. urea, di-2-pyridyl carbonate, phosgene, or triphosgene. $R_1$, $R_2$, $R_3$ are as defined above.

Scheme 2b

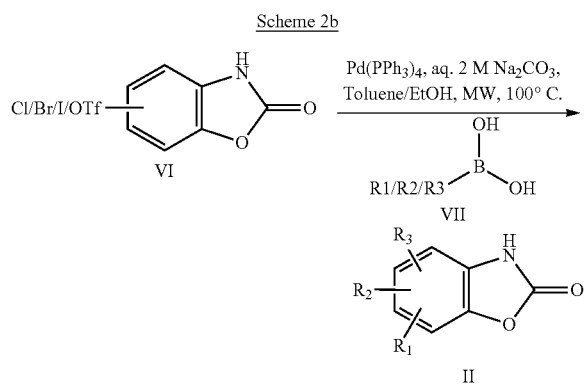

In cases where $R_1$, $R_2$, $R_3$ is an optionally substituted aromatic group, benzoxazol-2-ones of Formula II can be obtained by a metal-catalyzed cross coupling reaction between a compound of Formula VI (i.e. the benzoxazol-2-one building block substituted with a halogen such as chlorine, bromine, iodine or a triflate group), and a boronic acid of Formula VII, as exemplified using the Suzuki-Miyaura reaction (Scheme 2b). Boronic esters and organotrifluoroborate salts may be used instead of boronic acids. Properly substituted benzoxazol-2-ones of Formula VI are either commercial available or can be made according to Scheme 2a. Boronic acids of Formula VII, as defined above, are either commercially available or can be prepared from suitable precursors, as known to a person skilled in the art, according to standard synthetic methods as reported, for instance, in Norio Miyaura and Akira Suzuki, *Palladium-Catalyzed Cross-Coupling Reactions of Organoboron Compounds. Chemical Review* 1995, 95, 2457-2483, or in Michael Smith, Jerry March—*March's Advanced Organic Chemistry: reaction mechanisms and structure*—6th Edition, John Wiley & Sons Inc., 2007, and references cited therein, which are incorporated herein as references.

Scheme 2c

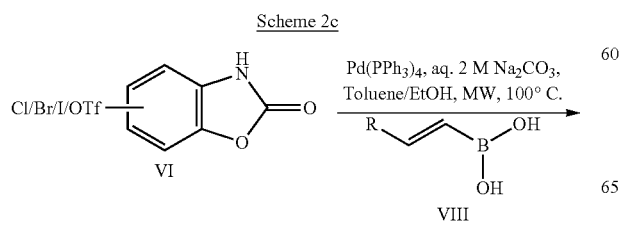

In cases where $R_1$, $R_2$, $R_3$ is an optionally substituted cycloalkyl $C_{1-6}$ alkylene, aryl $C_{1-6}$ alkylene, or a $C_{1-6}$ alkylene, benzoxazol-2-ones of Formula II can be obtained by coupling to the appropriate vinyl boronic acid of Formula VIII under Suzuki-Miyaura reaction conditions (Scheme 2c).

Scheme 2d

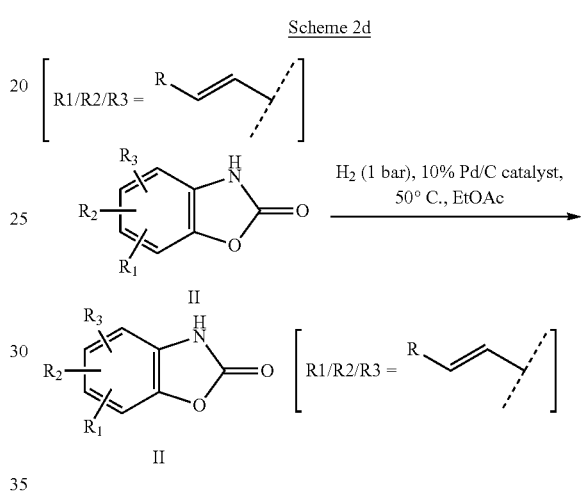

In cases where $R_1$, $R_2$, $R_3$ is an optionally substituted cycloalkyl $C_{1-6}$ alkyl, aryl $C_{1-6}$ alkyl, or a $C_{1-6}$ alkyl, benzoxazol-2-ones of Formula II can be prepared by hydrogenation of the alkenylic double bond in the product from Scheme 2c to give the corresponding alkylic bond as compounds of Formula II (Scheme 2d).

Scheme 2e

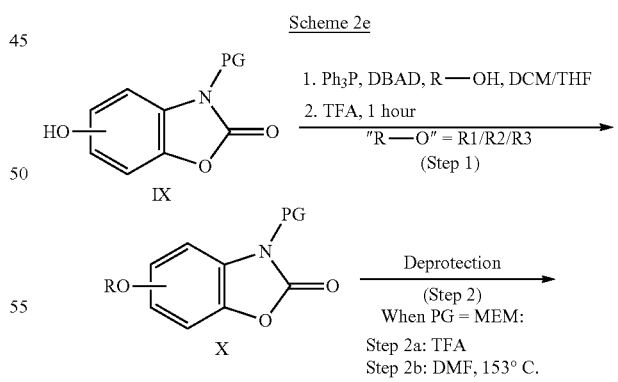

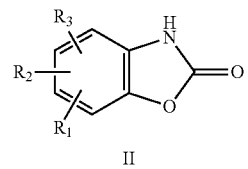

In cases where $R_1$, $R_2$, $R_3$ is a $C_{1-6}$ alkoxy, an optionally substituted cycloalkyl $C_{1-6}$ alkoxy, or an optionally substituted aryl $C_{1-6}$ alkoxy, benzoxazol-2-ones of Formula II can be provided by a Mitsunobu reaction of the N-protected and hydroxy-substituted benzoxazol-2-ones of Formula IX to get compound of Formula X (Scheme 2e, step 1), followed by de-protection (Scheme 2e, step 2). A suitable protecting group (PG) could be β-methoxyethoxymethyl ether (MEM) as described by Carato P et al., *Tetrahedron*, 2004, 60, 10321-10324; which can be removed with TFA (i.e. step 2a) followed by heating (153° C.) in DMF (i.e. step 2b). Other protecting groups can be used, as known to one of ordinary skill in the art of transformation of a chemical function into another, following standard procedures described, for instance, in Theodora W. Green and Peter G. M. Wuts—*Protective Groups in Organic Synthesis, Fourth Edition*, John Wiley & Sons Inc., 2006, which is herein incorporated as reference. Likewise, N-protected benzoxazol-2-ones of Formula IX can be made from commercially available 4-, 5-, 6-, or 7-hydroxy substituted 3H-1,3-benzoxazol-2-one using standard protecting group chemistry.

Scheme 2f

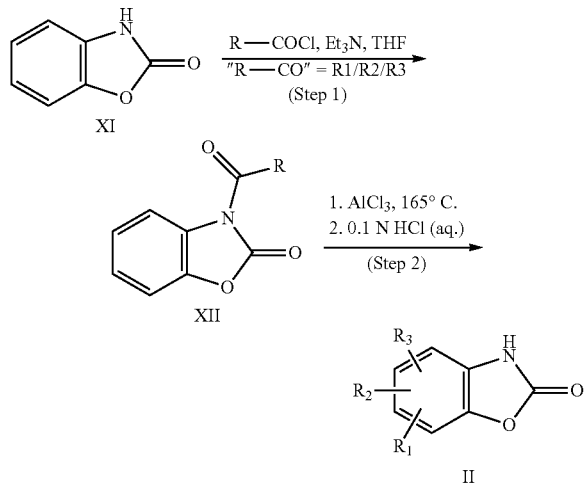

In cases where $R_1$, $R_2$, $R_3$ is $C_{1-6}$ alkylCO, optionally substituted arylCO, or optionally substituted aryl $C_{1-6}$ alkylCO, and where $R_1$, $R_2$, $R_3$ is in position 6 of the 3H-1,3-benzoxazol-2-one scaffold, compounds of Formula II can be provided by an N-acylation reaction of the commercial available un-substituted benzoxazol-2-ones of Formula XI (Scheme 2f, step 1), followed by a stereospecific "Fries-like" rearrangement (Scheme 2f, step 2), as described by Ucar H et al., *Tetrahedron*, 1998, 54, 1763-1772, and references herein. Likewise, a Friedel-Craft acylation procedure for providing compounds of Formula II, where $R_1$, $R_2$, $R_3$ is $C_{1-6}$ alkylCO, optionally substituted arylCO, or optionally substituted aryl $C_{1-6}$ alkylCO, and where $R_1$, $R_2$, $R_3$ is in position 5 of the benzoxazol-2-one scaffold, has been described in literature (Aichaoui H et al., *Tetrahedron*, 1991, 47, 6649-6654; Aichaoui H et al., *Synthesis*, 1990, 679-680, and references therein).

Synthesis of Compounds of Formula (IV):

Scheme 3

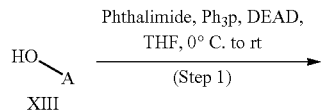

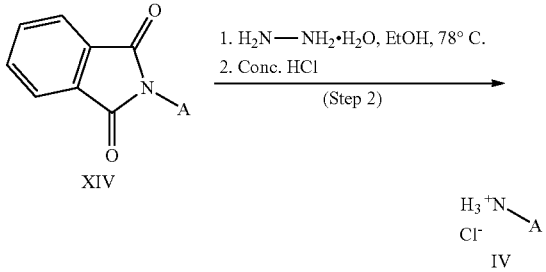

Amines of Formula IV are either commercially available or can be prepared according to standard synthetic methods as reported, for instance, in Michael Smith, Jerry March—*March's Advanced Organic Chemistry: reaction mechanisms and structure*—6th Edition, John Wiley & Sons Inc., 2007; Wiçek M et al., *Bioorg. Med. Chem.*, 2011, 19, 2850-2858; or Mitsunobu, O. *Synthesis*, 1981, 1; which are incorporated herein as reference. A is as defined above. For instance, as described in Scheme 3, alcohols of Formula XIII can be reacted with phthalimide under Mitsunobu reaction conditions to give the corresponding phthalimide of Formula XIV (Scheme 3, step 1). The corresponding amines of Formula IV can then be synthesized as hydrochloric salts upon hydrazine-mediated cleavage in refluxing ethanol followed by acidic work-up (Scheme 3, step 2). If desired, amines of Formula IV can also be prepared as their free base, by introducing a neutralization-step followed by extractions in organic solvents during the final work-up procedure. Alcohols of Formula XIII are either commercially available or can be made from the corresponding carboxylic acid or ester using common reducing agents, such as e.g. $LiAlH_4$.

Synthesis of Compounds of Formula (I), when $R_1$, $R_2$, $R_3$ is a Hydroxy Group (OH):

Scheme 4

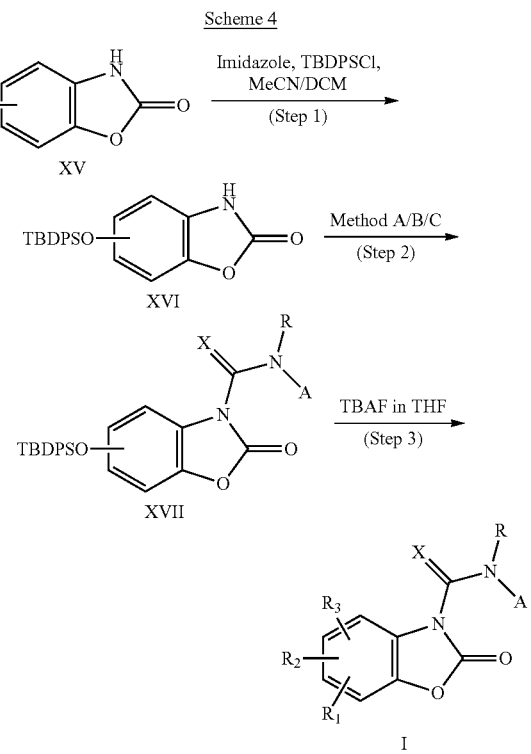

In certain embodiments, where $R_1$, $R_2$, $R_3$ is OH, a compound of Formula (I) can be obtained as described in Scheme 4, as certain protection/de-protection steps are needed. Other protection strategies can be applied, as known to one of ordinary skill in the art of transformation of a chemical function into another, following standard procedures described, for instance, in Theodora W. Green and Peter G. M. Wuts—*Protective Groups in Organic Synthesis, Fourth Edition*, John Wiley & Sons Inc., 2006, which is herein incorporated as reference.

III. Pharmaceutically Acceptable Salts

It will be understood that, as used herein, references to the compounds of Formula (I), (Ia) are meant to include also the pharmaceutically acceptable salts or derivatives thereof.

Furthermore, the compounds of Formula (I), (Ia) may form an acid addition salt or a salt with a base, depending on the kind of the substituents, and these salts are included in the present invention, as long as they are pharmaceutically acceptable salts.

The terms "the compound of the invention" and "the compounds of the present invention" and "the compounds of Formula (I), (Ia)" refer to each of the compounds of Formula (I), (Ia) and are meant to include their pharmaceutically acceptable salts, hydrates, solvates, and crystalline forms and also any suitable forms as illustrated hereinafter.

As used herein, the term "salt" refers to any salt of a compound according to the present invention prepared from an inorganic or organic acid or base and internally formed salts. Typically, such salts have a physiologically acceptable anion or cation.

Suitably physiologically or pharmaceutically acceptable salts of the compounds of the present invention include the hydrochloride, acetate, citrate, gluconate, lactate, tartrate, phosphate, borate, maleate, sulphate and nitrate, the hydrochloride being preferred.

The salts of compounds of Formula (I), (Ia) may be prepared by reacting a basic compound with the desired acid in solution.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (I), (Ia) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (I), (Ia) may readily be isolated in association with solvent molecules by crystallization or evaporation of an appropriate solvent to give the corresponding solvates.

The compounds of Formula (I), (Ia) may be in crystalline form. In certain embodiments, the crystalline forms of the compounds of Formula (I), (Ia) are polymorphs.

The subject invention also includes isotopically-labelled compounds, which are identical to those recited in Formula (I), (Ia) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, phosphorous, sulfur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e. $^3H$, and carbon-14, i.e. $^{14}C$, isotopes are particularly preferred for their ease of preparation and detectability. $^{11}C$ and $^{18}F$ isotopes are particularly useful in PET (Positron Emission Tomography), and $^{125}I$ isotopes are particularly useful in SPECT (Single Photon Emission Computerized Tomography), all useful in brain imaging. Further, substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. Isotopically-labelled compounds of Formula (I), (Ia) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (I), (Ia) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (I), (Ia) may have asymmetric carbon atoms or axial asymmetries in some cases and, correspondingly, it may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (I), (Ia) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist. Prodrugs or compounds which are stable ex vivo and which are convertible in the mammalian (e.g. human) body to the inventive compounds are, however, included.

The present invention also encompasses active metabolites of compounds of Formula (I), (Ia).

IV. Pharmaceutical Compositions

Another aspect of the present invention relates to pharmaceutical compositions containing a compound of Formula (I), (Ia).

The pharmaceutical compositions of the present invention encompass any compositions made by mixing a compound of the present invention and a pharmaceutically acceptable carrier. Such compositions are suitable for pharmaceutical use in an animal or human.

The pharmaceutical compositions of the present invention comprise a therapeutically effective amount of one or more compounds of Formula (I), (Ia) or a pharmaceutically acceptable salt thereof, and a pharmaceutically acceptable carrier.

A pharmaceutical composition may optionally contain other active ingredients. The term "carrier" refers to a vehicle, excipient, diluents, or adjuvant with which the therapeutic or active ingredient is administered. Any carrier and/or excipient suitable for the form of preparation desired for administration is contemplated for use with the compounds disclosed herein.

The carrier may take a wide variety of forms depending on the form of preparation desired for administration, e.g. oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents, and the like in the case of oral solid preparations such as, for example, powders, hard and soft capsules and tablets, with the solid oral preparations being preferred over the liquid preparations.

In certain embodiments, the compounds of the present invention can be combined as the active ingredient in intimate admixture with a suitable pharmaceutical carrier and/or excipient according to conventional pharmaceutical compounding techniques.

The compositions include compositions suitable for parenteral, including subcutaneous, intramuscular, and intravenous, pulmonary, nasal, rectal, topical or oral administration. Suitable route of administration in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy. The preferred compositions include compositions suitable for oral, parenteral, topical, subcutaneous, or pulmonary, in the form of nasal or buccal inhalation, administration. The compositions may be prepared by any of the methods well-known in the art of pharmacy.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula (I), (Ia) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I), (Ia) per dosage unit for daily administration.

In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

With respect to formulations with respect to any variety of routes of administration, methods and formulations for the administration of drugs are disclosed in *Remington's Pharmaceutical Sciences*, $17^{th}$ Edition, Gennaro et al. Eds., Mack Publishing Co., 1985, and *Remington's Pharmaceutical Sciences*, Gennaro A R ed. $20^{th}$ Edition, 2000, Williams & Wilkins PA, USA, and *Remington: The Science and Practice of Pharmacy*, $21^{st}$ Edition, Lippincott Williams & Wilkins Eds., 2005; and in *Ansel's Pharmaceutical Dosage Forms and Drug Delivery Systems*, $8^{th}$ Edition, Lippincott Williams & Wilkins Eds., 2005, which are herein incorporated as reference.

V. Medical Uses of Compounds of Formula (I) or (Ia) and Therapeutic Treatments

In accordance with some embodiments, the present invention provides the compounds of Formula (I), (Ia) for use in treating diseases or disorders associated with increased, relative to physiological or desired, levels of acid ceramidase protein or function, for example in subjects where acid ceramidase is overactive or over-expressed.

In accordance with other embodiments, a method of treatment of cancer, inflammation, pain and inflammatory pain, pulmonary diseases, in particular associated with increased relative to physiological or desired levels of acid ceramidase protein or function, for example in subjects where acid ceramidase is overactive or over-expressed, is also provided.

In some embodiments, the compounds of Formula (I), (Ia) and their pharmaceutical compositions and methods of administering them, are useful in treating cancer forms involving uncontrolled cell proliferation and/or dysfunctional sphingolipid signal transduction.

Cancer forms involving uncontrolled cell proliferation include, but are not limited to, pre-malignant conditions, for example hyperplasia, metaplasia or dysplasia, cancer metastasis, benign tumors, angiogenesis, hyperproliferative disorders and benign dysproliferative disorders. The treatment may be prophylactic or therapeutic. The subject to be treated may be an animal (e.g., mouse, rat, non-human primate and non-human mammal) or human.

In some embodiments, the compounds of Formula (I), (Ia) and their pharmaceutical compositions and methods of administering them, are useful in treating diseases or disorders involving primary and metastatic neoplastic diseases.

Primary and metastatic neoplastic diseases and related disorders that can be treated and/or prevented by the methods, compounds and compositions of the presently disclosed subject matter include, but are not limited to, prostate cancer, colorectal cancer, liver cancer, head and neck cancer, breast cancer, melanoma, metastatic melanoma, precancerous skin conditions such as actinic keratosis, skin cancers such as squamous cell carcinoma and basal cell carcinoma, and hematological malignancies such as chronic myelogeneous leukemia.

In accordance with certain embodiments the present invention provides a method for the treatment or prevention of cancer, cancer metastasis or psoriasis, comprising the administration of a therapeutically effective compound of Formula (I), (Ia) according to one or more of the embodiments described above, in a subject in need of treatment.

Cancers and related disorders that can be treated and/or prevented by the methods and compositions of the presently disclosed subject matter include, but are not limited to acute and chronic leukemia; polycythemia vera; lymphomas such as Hodgkin's disease, non-Hodgkin's disease; multiple myelomas, plasmacytoma; Waldenstrom's acroglobulinemia; gammopathy; heavy chain disease; bone and connective tissue sarcomas; brain tumors; breast cancer; adrenal cancer; thyroid cancer; pancreatic cancer; pituitary cancers; eye cancers; vaginal cancers; vulvar cancer; cervical cancers; uterine cancers; ovarian cancers; head and neck squamous cell cancers (HNSCCs), esophageal cancers; stomach cancers; colon cancers; rectal cancers; liver cancers; cholangiocarcinomas; testicular cancers, prostate cancers; penal cancers; oral cancers; basal cancers; salivary gland cancers; pharynx cancers; skin cancers; kidney cancers; Wilms' tumor; bladder cancers, myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. In certain embodiments, the present invention provides for compounds of Formula (I), (Ia) for the use in the treatment and/or prevention of breast cancer, prostate cancer, melanoma, alveolar cancer, or head and neck cancer.

The inventors found that the compounds of Formula (I), (Ia) play a role as regulator of cancer progression and are effective in the treatment of cancerous forms which are associated with an increased level of acid ceramidase protein or function, for example in subjects where acid ceramidase is overactive or over-expressed.

In accordance with certain embodiments the compounds of the invention are selective compounds for the treatment of prostate cancer, skin cancer especially melanoma, brain cancer, breast cancer, hepatocarcinoma, liver cancer, colon cancer or pancreatic cancer.

In certain embodiments, the present invention concerns compounds of Formula (I), (Ia) for use in the treatment of inflammatory diseases, such as rheumatoid arthritis and ulcerative cholites.

In certain embodiments, the compounds of Formula (I), (Ia) are useful in the treatment of different pain syndromes, disorders, diseases and conditions characterized by nociceptive pain, neuropathic pain, inflammatory pain, non-inflammatory pain, pain associated with acute conditions such as post-operative or post-traumatic stress disorders, pain associated with chronic conditions such as diabetes. Said method comprises administering a therapeutically effective amount of a compound of Formula (I), (Ia) or a pharmaceutically acceptable salt thereof, or a pharmaceutical composition thereof to the mammal.

In certain embodiments, the present invention provides the compounds of Formula (I), (Ia) for use in treating pulmonary diseases, such as asthma, chronic obstructive pulmonary disease (COPD), adult respiratory disease, acute respiratory distress syndrome, chronic bronchitis, emphysema and cough.

In certain embodiments, the present invention provides the compounds of Formula (I), (Ia) for use in treating diseases or disorders associated with neurodegeneration, such as Parkinson's disease, Alzheimer's disease, Huntington's diseases, multiple sclerosis and amyotrophic lateral sclerosis.

In some embodiments, the compounds of Formula (I), (Ia) and their pharmaceutical compositions and methods of administering them, are useful in treating or preventing a disease or disorder when administered in combination with other treatments.

In an additional aspect the present invention also concerns combination therapies or treatment with a compound of Formula (I), (Ia) or pharmaceutical composition containing them. In some embodiments, the compounds of Formula (I), (Ia) and their pharmaceutical compositions and methods of administering them, are useful in treating cancer when administered in combination with other pharmacological agents or active ingredients.

In certain embodiments these pharmacological agents are chemotherapeutic agents including, but not limited to, doxorubicin, daunorubicin, etoposide, cisplatin, oxaliplatin, carboplatin, gemcitabine, 5-fluorouracil, capecitabine, tegafur uracil (UFT), dacarbazine, fenretinide, camptothecin, irinotecan, fludarabine, vinblastine, taxol, mitomycin C.

In some embodiments, the compounds of Formula (I), (Ia) and their pharmaceutical compositions and methods of administering them, are useful in treating various cancers when administered before, during or after patient's treatment with radiation therapy.

In accordance with an additional aspect, the present invention provides a method of inhibiting ceramidase-related activity by contacting a biological sample with a compound of Formula (I), (Ia) as described above.

In certain embodiments the biological sample is an in vitro cell sample or an in vivo cell sample. The biological sample includes cells in culture media or lysed cells containing acid ceramidase. The biological sample includes cells present in plasma, urine, a tissue or organ sample or present in a subject. Accordingly in certain embodiments the methods of the invention can be used in medical or scientific research related to acid ceramidase and ceramidase-related activity.

VI. Biological Methods to Evaluate the Activity of the Compounds of the Invention Fluorescent-based In Vitro Assay General:

To evaluate the potency of the compounds towards acid ceramidase, a fluorescence-based in vitro assay previously described in literature (Bedia C et al., ChemBioChem, 2007, 8, 642-648) was implemented and optimized. This assay is based on a "fluorogenic probe" containing a coumarin group and a sphingoid base moiety (see figure below), which is not fluorescent in itself, but upon enzymatic cleavage by acid ceramidase followed by a chemical transformation liberates the fluorescent molecule umbelliferone (7-hydroxychromen-2-one). By quantifying the generation of umbelliferone using a fluorescence plate-reader, the level of enzymatic activity can be measured, whereby $IC_{50}$ values of compounds that inhibit this activity can be generated.

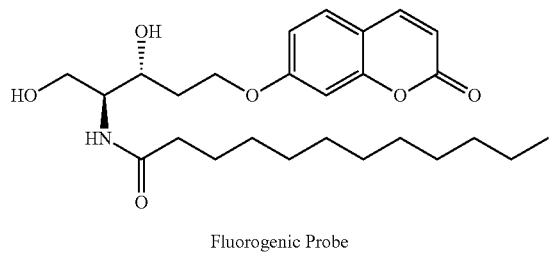 [SMILES: CCCCCCCCCCCC(=O)N[C@@H](CO)[C@H](O)CCOc1ccc2ccc(=O)oc2c1]

Fluorogenic Probe

Lysosomal lysate, enriched with acid ceramidase, was prepared from a cell line stably expressing human acid ceramidase. In the assay, the fluorogenic probe (or substrate) serves as a ceramide-analogue, which is recognized and hydrolyzed at the amide bond by acid ceramidase from the enriched lysate to yield the fatty acid and coumarinic aminodiol. By treating the solution with sodium periodate ($NaIO_4$), the coumarinic aminodiol is subsequently oxidized into an aldehyde intermediate, which undergoes a β-elimination reaction to release the strongly fluorescent umbelliferone.

Synthesis of the Fluorogenic Probe:

The fluorogenic probe was synthesized by the improved method described by Xia Z et al (Bioorg. Med. Chem., 2010, 18, 1003-1009), except for the last step (i.e. the acylation of the coumarinic aminodiol with dodecanoic acid), which was carried out as described by Bedia C et al (J. Lipid Res., 2010, 3542-3547), using 1-ethyl-3-(3-dimethylaminopropyl)carbodiimide hydrochloride (EDC.HCl), 1-hydroxybenzotriazole, and N,N-diisopropylethylamine in DMF. Analytical data of the fluorogenic probe:

N-[(1S,2R)-2-hydroxy-1-(hydroxymethyl)-4-(2-oxochromen-7-yl)oxy-butyl]dodecanamide White solid. Purity >95%; $^1$H NMR (400 MHz, DMSO-$d_6$): δ 0.85 (t, J=7.1 Hz, 3H), 1.19-1.26 (m, 16H), 1.41-1.54 (m, 2H), 1.66-1.76 (m, 1H), 1.92-2.02 (m, 1H), 2.04-2.17 (m, 2H), 3.51-3.57 (m, 2H), 3.64-3.76 (m, 2H), 4.19 (t, J=6.6 Hz, 2H), 4.54 (t, J=5.5 Hz, 1H), 4.84 (d, J=6.2 Hz, 1H), 6.30 (d, J=9.5 Hz, 1H), 6.93 (d, J=2.4 Hz, 1H), 6.96 (m, 1H), 7.54 (d, J=8.4 Hz, 1H), 7.64 (d, J=8.4 Hz, 1H), 8.01 (d, J=9.5 Hz, 1H). $^{13}$C NMR (101 MHz, CDCl$_3$): δ 13.90, 22.04, 25.33, 28.60, 28.67, 28.78, 28.95, 28.99 (2C), 31.26, 32.85, 35.47, 55.16, 60.58, 65.60, 66.72, 101.09, 112.18, 112.31, 112.61, 129.42, 144.29, 155.38, 160.24, 161.87, 172.17. $[\alpha]^{20}_D$=−10.13±0.6 (c=0.43, CHCl$_3$). MS (ESI) m/z: 462.2 [M−H]$^+$.

Preparation of Enzyme-enriched Lysate:

A lysosomal human acid ceramidase protein preparation was obtained from HEK293 cells stably expressing acid ceramidase suspended in 20 mM Tris HCl (pH 7.5) with 0.32 M sucrose. The cell solution was sonicated and centrifuged at 800×g for 15 min at 4° C. Supernatants were then centrifuged at 12,000×g for 30 min at 4° C. Pellets were re-suspended in PBS pH 7.4 and subjected to two freeze-thaw cycles at −80° C. The suspension was finally centrifuged at 105,000×g for 1 hour at 4° C. and protein concentration was measured in the supernatant with bicinchinonic-acid based protein assay. This human acid ceramidase-enriched preparation allowed us to further optimize the enzymatic assay and to use smaller amounts of lysate (2 μg/well) and substrate (5 μM).

Procedure for Fluorescent-based In Vitro Assay:

The assay was performed in Optiplate 96-wells black plates, with each reaction well containing a mixture of 25 mM sodium acetate buffer pH 4.5 and a fixed amount of protein (2 μg) in a volume of 85 μL. After 30 mins of pre-incubation with test compounds (diluted 20× from DMSO stock solutions at different concentrations), the fluorogenic probe was added (diluted 20× from EtOH stock solution, final concentration 5 μM). After incubation for 3 hours at 37° C., the reactions were stopped with 50 μL of methanol and 100 μL of a 2.5 mg/mL NaIO$_4$ fresh solution in 100 mM Glycine/NaOH pH 10.6. The plate was incubated at 37° C. for 2 hours in the dark and fluorescence intensities were measured at excitation/emission wavelengths of 360/446 nm. Negative control samples consisted of the same incubation mixture in the absence of protein extracts. The $IC_{50}$ values or percent of inhibition, at the indicated concentration, of selected compounds described in the invention are reported in Table 2.

Procedure for LC-MS Based In Vitro Assay:

hAC protein preparation (10 μg) was preincubated with inhibitors (final DMSO concentration 1%) in assay buffer (100 mM sodium phosphate, 0.1% Nonidet P-40, 150 mM NaCl, 3 mM DTT, 100 mM sodium citrate, pH 4.5) for 30 min at 37° C. Reactions were started by the addition of 50 μM N-lauroyl ceramide (Nu-Chek Prep, Elysian, Minn.) and carried on for 30 min at 37° C. Reactions were stopped by addition of a mixture of chloroform/methanol (2:1, vol/vol) containing 1 nmol 11-lauroleic acid (NuChek Prep). The organic phases were collected, dried under nitrogen and analyzed by UPLC/MS (Acquity, Waters). In the negative-ion mode monitoring the reaction product (lauric acid, m/z=199) using 11-lauroleic acid as internal standard.

Lipids were eluted on an Acquity UPLC BEH C18 column (50 mm length, 2.1 mm i.d., 1.7 μm pore size, Waters) column at 0.5 mL·min-1 for 1.5 min with a gradient of acetonitrile (MeCN) and water, both containing 0.25% acetic acid and 5 mM ammonium acetate (70% to 100% MeCN in 0.5 min, 100% MeCN for 0.5 min, 70% CH$_3$CN for 0.4 min). The column temperature was 40° C. Electrospray ionization (ESI) was in the negative mode, capillary voltage was 1 kV and cone voltage was 50 V. N$_2$ was used as drying gas at a flow rate of 500 L/h and at a temperature of 400° C.

The [M−H]$^−$ ion was monitored in the selected-ion monitoring mode (m/z values: lauric acid 199, 11-lauroleic acid 197.35). Calibration curves were generated with authentic lauric acid (Nu Check Prep). Inhibition of AC activity was calculated as reduction of lauric acid in the samples compared to vehicle controls. $IC_{50}$ values were calculated by non-linear regression analysis of log [concentration]/inhibition curves using GraphPad Prism 5 (GraphPad Software Inc., CA—USA) applying a standard slope curve fitting.

Lipid Extraction and Ceramide, Sphingosine and Sphinganine Analysis

Lipids were extracted from mouse tissue lysate with a chloroform/MeOH mixture (2:1 v/v, 3 mL) containing internal standards. The organic phase was collected, dried under nitrogen, and dissolved in chloroform/MeOH (1:3 v/v) for LC-MS analyses. Ceramides, sphingosine and sphinganine were analyzed by LC-MS/MS, using a Waters Acquity UPLC coupled with a Waters Xevo TQMS and interfaced with ESI. Separation was done on a Waters Acquity BEH C18 1.7 µm column (2.1×50 mm) at 60° C. A step gradient of 0.1% formic acid in acetonitrile/water (20:80 v/v) as solvent A and 0.1 formic acid in acetonitrile/isopropyl alcohol (20:80 v/v) as solvent B was applied at a flow rate of 0.4 mL/min. Detection was in the positive ionization mode. Capillary voltage was 3.5 kV and cone voltage was 25 V. The source temperature and desolvation temperatures were set at 120° C. and 600° C. respectively. Desolvation gas and cone gas (N2) flow were 800 and 20 l/h, respectively.

Tissue-derived ceramides were identified by comparison of their LC retention times and $MS^2$ fragmentation patterns with those of authentic standards (Avanti Polar Lipids). Extracted ion chromatograms were used to quantify myristoyl ceramide (C14:0, m/z 510.5>492.5>264.3), palmitoyl ceramide (C16:0, m/z 538.5>520.3>264.3), stearoyl ceramide (C18:0 m/z 566.5>548.3>264.3), lignoceroyl ceramide (C24:0 m/z 650.5>632.3>264.3), nervonoyl ceramide (C24:1 m/z 648.5>630.3>264.3) and using lauroyl ceramide standard (m/z 482.5>464.5>264.3). Detection and analysis were controlled by Waters MassLynx software version 4.1.

Tissue-derived sphingosine and sphinganine were identified by comparison of their LC retention times and $MS^2$ fragmentation patterns with those of authentic standards (Avanti Polar Lipids). Extracted ion chromatograms were used to quantify sphingosine (C18:0, m/z 300.5>282.5) and sphinganine standard (C18:0, m/z 303>285). Detection and analysis were controlled by Waters MassLynx software version 4.1.

Cell Viability and Proliferation Assays

Cell viability can be defined as the number of living cells in a sample. There are many well-described and widely used methods to evaluate cell viability such as trypan blue dye exclusion, MTT reduction or ATP measurement [for a review, see Stoddart M J, *Cell viability assays: introduction, Methods in Molecular Biology*, 2011, Vol. 740].

Cells are seeded in 12- or 96-well plates in complete medium 24 hours before treatment and then incubated for 24 hours (single treatment) or 72 hours (multiple treatments) with different compounds-concentrations.

Cell viability can be evaluated using the trypan blue exclusion assay, which is based on the principle that viable cells have intact cell membrane and can therefore exclude the trypan blue dye, while damaged/dead cells cannot. Cells are harvested, centrifuged at 800×g for 10 min and pellets re-suspended in PBS. Cells are diluted 1:1 with 0.4% trypan blue dye (Sigma), incubated for 1 min and white (viable) cells are counted with a hemacytometer.

Alternatively, cell viability can be assessed measuring mitochondrial functionality by the MTT assay, which is based on the reduction of the soluble tetrazolium salt MTT [(3-(4,5-dimethylthiazol-2-yl)-2,5-diphenyltetrazolium bromide] into insoluble formazan by mitochondria. Briefly, cells are treated with selected compounds for 24 or 72 hr, washed with PBS and incubated with 0.5 mg/mL MTT for 2 hours at room temperature. MTT reduction is quantified by absorbance at 570 nm using a UV-visible plate reader.

In some experiments, crystal violet assay can be used to evaluate cells morphology and proliferation: at different time points after treatment cells are washed with PBS and fixed with 4% formaldehyde for 10 min. Cells are stained with 0.4% crystal violet in 50% MeOH for 20 min and extensively washed with water to remove excess dye. Crystal violet is dissolved in DMSO. The absorbance of the dissolved dye, corresponding to the number of viable cells, is measured in a UV-visible plate reader at 570 nm.

Finally, the CellTiter-Glo® Luminescent Cell Viability Assay can be used to determine the number of viable cells in culture based on quantitation of the ATP present, which signals the presence of metabolically active cells. Briefly, a volume of CellTiter-Glo® Reagent equal to the volume of cell culture medium present in each well is added to 96-well plates after drug treatment. Contents are mixed for 2 minutes on an orbital shaker to induce cell lysis and plate was incubated at room temperature for 10 minutes to stabilize signal before reading luminescence.

Isobolographic Analysis

Interaction between drugs can be assessed by isobolographic analysis, based on the concept of dose-equivalence which follows from the dose effect curves of the individual drugs (Tallarida R J, *Interactions between drugs and occupied receptors. Pharmacol. Ther.* 2007, 113, 197-209; Tallarida R J, Raffa R B, *The application of drug dose equivalence in the quantitative analysis of receptor occupation and drug combinations. Pharmacol. Ther.* 2010, 127, 165-174). Specifically, the individual drugs' potency and efficacy allow calculating the expected effect of a combination of the two drugs.

In the experiment of combined treatment, isobolograms are constructed by plotting on vertical and horizontal axes the $ED_{50}$ data of the single drugs measured by trypan blue assay after subcronic treatment for 72 hrs. The straight line with axial intercepts represents the isobole of additivity and allows calculating the theoretical additive dose. Synergism is indicated by an observed pair (x, y) that plots below the isobole for the specified effect, whereas sub-additivity is indicated when an observed pair (x, y) plots above the isobole.

Alternatively, drug synergism was evaluated using CompuSyn software, which was set up by Dr. Dorothy Chou in 2005 (The ComboSyn, Inc.) [Chou T C and Martin N. *CompuSyn for Drug Combinations: PC Software and User's Guide: A Computer Program for Quantitation of Synergism and Antagonism in Drug Combinations, and the Determination of IC50 and ED50 and LD50 Values*, ComboSyn Inc, Paramus, (N.J.), 2005.]

Statistics

GraphPad Prism software (GraphPad Software, Inc., USA) was used for statistical analysis.

Data were analyzed using the Student t-test or 1-way ANOVA followed by Bonferroni post hoc test for multiple comparisons. Two-way ANOVA was used to compare the means of data with two independent variables. Differences between groups were considered statistically significant at values of $p<0.05$. Results are expressed as mean±SEM.

PREPARATIVE EXAMPLES

Abbreviations used for solvents and reagents are: acetonitrile (MeCN), ammonium chloride ($NH_4Cl$), dichloromethane (DCM), 4-(dimethylamino)-pyridine (DMAP), N,N-diisopropylethylamine (DIPEA), diisopropyl azodicarboxylate (DIAD), N,N-dimethylacetamide (DMA), N,N-dimethylformamide (DMF), dimethylsulfoxide (DMSO), di-tert-butyl azodicarboxylate (DBAD), diethyl azodicarboxylate (DEAD), ethanol (EtOH), ethyl acetate (EtOAc), hydrochloric acid (HCl), lithium aluminum hydride (LiAlH$_4$), methanol (MeOH), potassium carbonate (K$_2$CO$_3$), sodium bicarbonate (NaHCO$_3$), sodium hydroxide (NaOH), sodium sulfate (Na$_2$SO$_4$), sodium carbonate (Na$_2$CO$_3$), tetrabutylammonium fluoride (TBAF), tetrahydrofuran (THF), thionyl chloride (SOCl$_2$), triethylamine (Et$_3$N), trifluoroacetic acid (TFA), triphenylphosphine (Ph$_3$P). Other abbreviations used are: aqueous (aq.), equivalents (eq.), minutes (min), saturated (sat.).

Hydrogenation reactions were performed using H-Cube™ continuous hydrogenation equipment (SS-reaction line version), employing disposable catalyst cartridges (CatCart™) preloaded with the required heterogeneous catalyst. Microwave heating was performed using Explorer™-48 positions instrument (CEM).

UPLC-MS analyses were run on a Waters ACQUITY UPLC-MS instrument consisting of a SQD Single Quadropole Mass Spectrometer equipped with an electrospray ionization interface and a photodiode array (PDA) detector. The UPLC column was an ACQUITY UPLC BEH C18 column (50×2.1 mmID, particle size 1.7 μm) with a VanGuard BEH C18 pre-column (5×2.1 mmID, particle size 1.7 μm). The mobile phases were 10 mM ammonium acetate at pH 5 adjusted with acetic acid (A) and 10 mM ammonium acetate in MeCN-water (95:5) at pH 5 (B). Electrospray ionization in positive and negative mode was used in the mass scan range 100-500 Da, and PDA range was 210-400 nm.

Purifications by automated column chromatography were done using a Teledyne ISCO apparatus (CombiFlash™ Rf) with pre-packed silica gel columns of different sizes (from 4-80 g). Mixtures of increasing polarity of cyclohexane (A) and EtOAc (B) or DCM (A) and MeOH (B) were used as eluents.

Purification by preparative HPLC-MS were run on a Waters Autopurification system consisting of a 3100 Single Quadropole Mass Spectrometer equipped with an electrospray ionization interface and a 2998 Photodiode Array Detector. The HPLC system included a 2747 Sample Manager, 2545 Binary Gradient Module, System XBridge™ Prep C18 OBD column (100×19 mmID, particle size 5 μm) with a XBridge™ Prep C18 (10×19 mmID, particle size 5 μm) Guard Cartridge. The mobile phases were either 1) water (A) and MeCN (B) or 2) 10 mM ammonium acetate at pH 5 adjusted with acetic acid (A) and 10 mM ammonium acetate in MeCN:water (95:5) at pH 5 (B). Electrospray ionization in positive and negative mode was used in the mass scan range 100-500 Da.

NMR experiments were run on a Bruker Avance III 400 system (400.13 MHz for $^1$H, and 100.62 MHz for $^{13}$C), equipped with a BBI probe and Z-gradients. Spectra were acquired at 300 K, using deuterated dimethylsulfoxyde (DMSO-d$_6$) or deuterated chloroform (CDCl$_3$) as solvents. Chemical shifts for $^1$H and $^{13}$C spectra were recorded in parts per million using the residual non-deuterated solvent as the internal standard (for CDCl$_3$: 7.26 ppm, $^1$H and 77.16 ppm, $^{13}$C; for DMSO-d$_6$: 2.50 ppm, $^1$H; 39.52 ppm, $^{13}$C). All final compounds were >95% pure by NMR ($^1$H, $^{13}$C, $^1$H—$^1$H COSY, $^1$H—$^{13}$C HSQC) and UPLC (UV). DMSO stock solutions of final compounds used for biological tests were evaluated prior to tests (NMR, UPLC), and the concentration was evaluated by quantitative NMR.

General Procedure I: Synthesis of Compounds of Formula (I), (Ia) (Scheme 1)

Method A:

The optionally substituted 3H-1,3-benzoxazol-2-one II (1 eq.) was dissolved in dry pyridine (6 mL per mmol II). DMAP (1.1 eq.) was added and the reaction mixture stirred under nitrogen atmosphere at room temperature for 30 min. The isocyanate or thioisocyanate III (1.1 eq.) was added and the resulting mixture was stirred for 15 hours. The solvent was removed under reduced pressure, and the compound was purified by column chromatography using the Teledyne ISCO apparatus (cyclohexane:EtOAc).

Method B:

Triphosgene (1 eq.) was placed in an oven-dried flask, cooled to 0° C., and dissolved in dry pyridine (5 mL per mmol triphosgene) at 0° C. The optionally substituted 3H-1,3-benzoxazol-2-one II (1.0 eq.) dissolved in dry pyridine (1.9 mL per mmol II) was added, and the reaction mixture was stirred under nitrogen for 30 min at room temperature. The solution was cooled to 0° C. and the amine IV (1.5 eq.), dissolved in dry pyridine (3.5 mL per mmol IV), was added. The reaction was allowed to warm to room temperature and stirred for 3 hours. The solvent was removed under reduced pressure, and the compound was purified by column chromatography using the Teledyne ISCO apparatus (cyclohexane:EtOAc).

Method C:

In an oven-dried flask, triphosgene (1.0 eq.) was dissolved in dry DCM (5 mL per mmol triphosgene). A solution of the optionally substituted 3H-1,3-benzoxazol-2-one II (1.0 eq.) and Et$_3$N (4.0 eq.) in dry DCM (5.6 mL per mmol II) was added at 0° C., and the reaction was stirred for 1 hour at room temperature under nitrogen. Then a solution of the amine IV (1.5 eq.) and Et$_3$N (1.5 eq.) in dry DCM (6.5 mL per mmol IV) was added at 0° C., and the reaction was stirred at room temperature for 3 hours. The reaction mixture was diluted with DCM (20 mL per mmol II) and quenched with sat. aq. NH$_4$Cl (30 mL per mmol II). The two phases were separated and the aqueous layer was extracted with DCM (3×20 mL per mmol II). The combined organic phases were dried over Na$_2$SO$_4$, evaporated on celite or silica, and the compound was purified by column chromatography using the Teledyne ISCO apparatus (cyclohexane:EtOAc).

General Procedure II: Synthesis of Compounds of Formula II (Scheme 2a)

1,1'-Carbonyldiimidazole (1.6 eq.) was added to a solution of the optionally substituted aminophenol V (1 eq.) in DMF (2.7 mL per mmol V), and the solution was heated to 60° C. for 2 hours. After cooling to room temperature, the reaction mixture was poured into water (15 mL per mmol V) and extracted with EtOAc (3×15 mL per mmol V). The combined organic phases were washed with brine (15 mL per mmol V), dried over Na$_2$SO$_4$, and evaporated on celite. The compound was purified by column chromatography using the Teledyne ISCO apparatus (cyclohexa ne:EtOAc).

General Procedure III: Synthesis of Compounds of Formula II (Scheme 2b)

VI, e.g. bromo-substituted 3H-1,3-benzoxazol-2-one, (1 eq.) was suspended in a 1:1 toluene/EtOH mixture (10 mL per mmol VI). The boronic acid VII (1.5 eq.) was added followed by aq. Na$_2$CO$_3$ (2 M, 0.55 mL per mmol VI, 1.1 eq.). The resulting suspension was degassed under nitrogen for 10 min, followed by addition of tetrakis(triphenylphosphine) palladium(0) (0.1 eq.) and heating under microwave irradiation at 100° C. for 30 min. The reaction mixture was diluted with EtOAc (40 mL per mmol VI), and water (40 mL per mmol VI) was added. The two phases were separated and the aqueous layer was extracted with EtOAc (2×40 mL per mmol VI). The combined organic phases were dried over Na₂SO₄, evaporated on celite, and the compound was purified by column chromatography using the Teledyne ISCO apparatus (cyclohexane:EtOAc).

General Procedure IV: Synthesis of Compounds of Formula II (Scheme 2c)

This procedure is similar to the General Procedure III, except that vinylboronic acids VIII are used instead of boronic acids VII.

General Procedure V: Synthesis of Compounds of Formula II (Scheme 2d)

The ethenyl-substituted 3H-1,3-benzoxazol-2-one II (1 eq.), was dissolved in EtOAc (75 mL per mmol II) and hydrogenated in the H-Cube apparatus at 50° C. using 10% Pd/C as catalyst-cartridge and 1 bar hydrogen pressure. The reaction mixture was concentrated under reduced pressure affording pure product.

General Procedure VI: Synthesis of Compounds of Formula II (Scheme 2e)

Step 1:

The hydroxy-substituted and N-MEM-protected 1,3-benzoxazol-2-one IX (1 eq.) and Ph₃P (2 eq.) were solubilized in DCM (5.7 mL per mmol IX) and THF (3 mL per mmol IX) at room temperature. The alcohol (2 eq.) was added, the flask was evacuated, and a nitrogen balloon attached. DBAD (2 eq.) was solubilized in DCM (3 mL per mmol IX) and added slowly to the mixture, which was then stirred for 1 hour. TFA was added (5.5 mL per mmol IX) and the mixture stirred for 1 hour. The reaction mixture was evaporated and taken up in DCM (40 mL per mmol IX). The organic phase was washed with water (40 mL per mmol IX), and the aqueous layer was extracted with DCM (3×40 mL per mmol IX). The combined organic phases were washed with brine (40 mL per mmol IX), dried over Na₂SO₄, and evaporated. The compound X was purified by column chromatography using the Teledyne ISCO apparatus (cyclohexane:EtOAc).

Step 2a:

X (1 eq.) was treated with TFA (18 mL per mmol X) at room temperature. The reaction was heated to 50° C. and stirred for 2 hours. TFA was concentrated under reduced pressure and co-evaporated twice with DCM, and the residue was taken up in EtOAc (30 mL per mmol X). The organic phase was washed with water (30 mL per mmol X), the two phases were separated, and the aqueous layer was extracted with EtOAc (2×30 mL per mmol X). The combined organic phases were dried over Na₂SO₄, evaporated, and purified by column chromatography using the Teledyne ISCO apparatus (cyclohexane:EtOAc).

Step 2b:

The resulting compound from step 2 was treated with DMF (15 mL per mmol X) at 153° C. for 3 hours. After cooling to room temperature, the reaction mixture was poured into water (60 mL per mmol X) and extracted with EtOAc (3×60 mL per mmol X). The combined organic phases were washed with brine (30 mL per mmol X), dried over Na₂SO₄, and evaporated on celite. The compound was purified by column chromatography using the Teledyne ISCO apparatus (cyclohexane:EtOAc).

General Procedure VII: Synthesis of Compounds of Formula II (Scheme 2f)

Step 1:

The acid chloride (2.4 eq.) was added dropwise over 10 min to a solution of 3H-1,3-benzoxazol-2-one XI (1 eq.) and Et₃N (1.2 eq.) in dry THF (1 mL per mmol XI) cooled at 0° C. The reaction mixture was heated under reflux for 2 hours, and the solution was transferred to a flask with ice-cold water (20 mL per mmol XI), which was then stirred for 30 min. The resulting precipitate was filtered, washed with ice-cold water, and transferred to a round-bottom flask. The compound was solubilized in EtOH, heated to obtain a clear solution, and then placed on ice. After 30 minutes, the crystals were filtered, washed with ice-cold EtOH, and placed under vacuum to obtain pure product XII.

Step 2:

XII (1 eq.) and AlCl₃ (2.5 eq.) was thoroughly mixed together, slowly heated to 165° C., and stirred for 3 hours. After cooling to room temperature, 0.1 N HCl (10 mL per mmol XII) was added to the brown syrup on ice, and the solution was stirred for 30 min. EtOAc (10 mL per mmol XII) was added and the two phases separated. The water phase was extracted once with EtOAc (10 mL per mmol XII), and the combined organic phases were washed once with brine (10 mL per mmol XII), dried over Na₂SO₄, and evaporated onto celite. The compound was purified by column chromatography using the Teledyne ISCO apparatus (cyclohexane:EtOAc).

General Procedure VIII: Synthesis of Compounds of Formula IV (Scheme 3)

Step 1:

In an oven-dried flask, phthalimide (1.0 eq.), Ph₃P (1.0 eq.) and alcohol XIII (1.0 eq.) were dissolved in dry THF (1.4 mL per mmol XIII). The resulting solution was cooled to 0° C. and a solution of DEAD (40% wt in toluene, 1.0 eq.) in dry THF (0.5 mL per mmol XIII) was added dropwise. The reaction mixture was allowed to warm to room temperature and stirred under nitrogen for 15 hours. The solvent was evaporated under reduced pressure, the residue suspended in diethyl ether, and the flask placed on ice. The precipitate was filtered off and the filtrate was evaporated on celite or silica. Pure compound XIV was obtained by column chromatography using the Teledyne ISCO apparatus (cyclohexane:EtOAc).

Step 2:

XIV (1.0 eq) and hydrazine monohydrate (1.0 eq) in EtOH (8 mL per mmol XIV) were refluxed for 3 hours. A precipitate was formed, and the suspension was cooled to room temperature, filtered, acidified with conc. HCl, and filtered once more. The filtrate was concentrated under reduced pressure to afford amine IV as the HCl salt, which was used in the following step without further purification.

Intermediate 1. 5-nitro-3H-1,3-benzoxazol-2-one

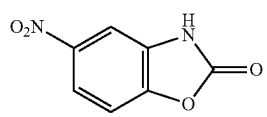 [SMILES: O=c1[nH]c2cc([N+](=O)[O-])ccc2o1]

The title compound was obtained according to the General Procedure II, starting from 2-amino-4-nitro-phenol (116 mg, 0.75 mmol). Yellow solid (125 mg, 92%). ¹H NMR (400 MHz, DMSO-d₆) δ 7.53 (d, J=8.8 Hz, 1H), 7.85 (d, J=2.4 Hz, 1H), 8.06 (dd, J=8.8, 2.4 Hz, 1H), 12.20 (s, 1H). MS (ESI) m/z: 179 [M−H]⁻. [In a similar way, but using THF as solvent, Abdelaal S M et al., *J. Heterocyclic Chem.*, 1992, 29, 1069-1076 has synthesized this compound; Spectral data has been reported by Maleski R J et al., *J Heterocyclic Chem.*, 1991, 28, 1937-1939].

Intermediate 2. 6-Nitro-3H-1,3-benzoxazol-2-one

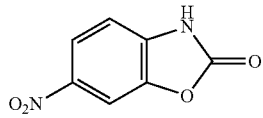

The title compound was obtained according to the General Procedure II, starting from 2-amino-5-nitro-phenol (770 mg, 5 mmol). The reaction was heated for 4 hours. Yellow solid (781 mg, 87%). $^1$H NMR (400 MHz, DMSO-d$_6$) δ 7.28 (d, J=8.6 Hz, 1H), 8.13 (dd, J=8.6 Hz, 1H), 8.20 (d, J=2.2 Hz, 1H), 12.40 (br s, 1H). MS (ESI) m/z: 179 [M−H]$^-$. [In a similar way, but using THF as solvent, Nachman R J, *J. Heterocyclic Chem.*, 1982, 19, 1545-1547 has reported the synthesis and analytical data of the title compound].

Intermediate 3.
5-(Trifluoromethyl)-3H-1,3-benzoxazol-2-one

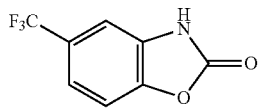 [SMILES: O=c1[nH]c2cc(C(F)(F)F)ccc2o1]

The title compound was obtained according to the General Procedure II, starting from 2-amino-4-(trifluoromethyl)phenol (133 mg, 0.75 mmol). White solid (130 mg, 85%). $^1$H NMR (400 MHz, DMSO-d$_6$) δ 7.36-7.38 (m, 1H), 7.45-7.51 (m, 2H), 12.02 (s, 1H). MS (ESI) m/z: 202 [M−H]$^-$.

Intermediate 4.
6-(Trifluoromethyl)-3H-1,3-benzoxazol-2-one

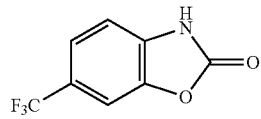

The title compound was obtained according to the General Procedure II, starting from 2-amino-5-(trifluoromethyl)phenol (443 mg, 2.5 mmol). The reaction was heated 60° C. for 1 hour. White solid (458 mg, 90%). $^1$H NMR (400 MHz, DMSO-d$_6$) δ 7.26 (d, J=8.2 Hz, 1H), 7.52 (dd, J=8.4 Hz, 1H), 7.72 (d, J=1.7 Hz, 1H), 12.07 (s, 1H). MS (ESI) m/z: 202 [M−H]$^-$.

Intermediate 5.
2-Oxo-3H-1,3-benzoxazole-5-carbonitrile

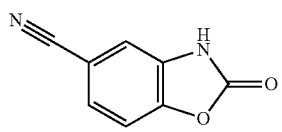

The title compound was obtained according to the General Procedure II, starting from 3-amino-4-hydroxy-benzonitrile (101 mg, 0.75 mmol). White solid (103 mg, 86%). $^1$H NMR (400 MHz, DMSO-d$_6$) δ 7.49 (dd, J=8.2, 0.5 Hz, 1H), 7.57-7.59 (m, 1H), 7.61 (d, J=1.7 Hz, 1H), 12.10 (s, 1H). MS (ESI) m/z: 159 [M−H]$^-$.

Intermediate 6.
5,6-Dichloro-3H-1,3-benzoxazol-2-one

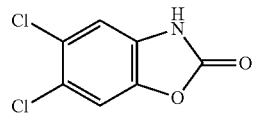

The title compound was obtained according to the General Procedure II, starting from 2-amino-4,5-dichloro-phenol (134 mg, 0.75 mmol). White solid (123 mg, 80%). $^1$H NMR (400 MHz, DMSO-d$_6$) δ 7.35 (s, 1H), 7.70 (s, 1H), 11.99 (s, 1H). MS (ESI) m/z: 204 [M−H]$^-$.

Intermediate 7. 4-Methyl-3H-1,3-benzoxazol-2-one

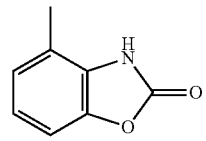

The title compound was obtained according to the General Procedure II, starting from 2-amino-3-methyl-phenol (92 mg, 0.75 mmol). Light-brown solid (95.2 mg, 85%). $^1$H NMR (400 MHz, DMSO-d$_6$) δ 2.29 (s, 3H), 6.94-7.00 (m, 2H), 7.05-7.11 (m, 1H), 11.66 (s, 1H). MS (ESI) m/z: 148 [M−H]$^-$. [For analytical data of title compound, see also: Quaranta L et al, *Organic Letters*, 2002, 4, 39-42].

Intermediate 8. 7-Methyl-3H-1,3-benzoxazol-2-one

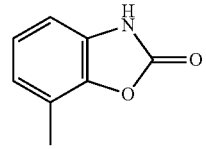

The title compound was obtained according to the General Procedure II, starting from 2-amino-6-methyl-phenol (92 mg, 0.75 mmol). Light-brown solid (82.8 mg, 74%). $^1$H NMR (400 MHz, DMSO-d$_6$) δ 2.30 (s, 3H), 6.88-6.93 (m, 2H), 7.03 (t, J=7.7 Hz, 1H), 11.52 (s, 1H). MS (ESI) m/z: 148 [M−H]$^-$. [For analytical data of title compound, see also: Clark R D et al., *J. Org. Chem.*, 1982, 47, 2804-2806].

Intermediate 9. 7-Bromo-3H-1,3-benzoxazol-2-one

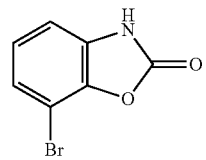 [SMILES: O=c1[nH]c2cccc(Br)c2o1]

The title compound was obtained according to the General Procedure II, starting from 2-amino-6-bromo-phenol (470 mg, 2.5 mmol). Light-brown solid (477 mg, 89%). $^1$H NMR (400 MHz, DMSO-d$_6$) δ 7.07-7.13 (m, 2H), 7.25-7.31 (m, 2H), 11.93 (s, 1H). MS (ESI) m/z: 212.0 and 214 [M−H]$^-$. [In a similar way, but using THF as solvent, Fukaya T et al., *Bioorg. Med. Chem.*, 2012, 20, 5568-5582 has reported the synthesis and analytical data of the title compound].

Intermediate 10. 5-Phenyl-3H-1,3-benzoxazol-2-one

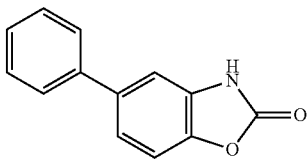 [SMILES: O=c1[nH]c2cc(-c3ccccc3)ccc2o1]

The title compound was obtained according to the General Procedure III, starting from 5-bromobenzoxazolone (80 mg, 0.374 mmol) and phenylboronic acid (68 mg, 0.561 mmol). In total, two microwave cycles were applied using fresh palladium catalyst and boronic acid each time. White solid (14.9 mg, 19%). $^1$H NMR (400 MHz, CDCl$_3$) δ 7.26-7.28 (m, 2H), 7.32-7.39 (m, 2H), 7.42-7.47 (m, 2H), 7.52-7.55 (m, 2H), 8.06 (s, 1H). MS (ESI) m/z: 210 [M−H]$^-$. [For analytical data of title compound, see also: Fukaya T et al., *Bioorg. Med. Chem.*, 2012, 20, 5568-5582].

Intermediate 11. 5-(4-Methoxyphenyl)-3H-1,3-benzoxazol-2-one

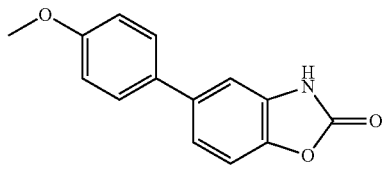 [SMILES: COc1ccc(-c2ccc3oc(=O)[nH]c3c2)cc1]

The title compound was obtained according to the General Procedure III, starting from 5-bromobenzoxazolone (80 mg, 0.374 mmol) and (4-methoxyphenyl)boronic acid (85 mg, 0.561 mmol). In total, two microwave cycles were applied using fresh palladium catalyst and boronic acid each time. Title compound was obtained as an off-white/yellowish solid (41.0 mg, 45%). $^1$H NMR (400 MHz, CDCl$_3$) δ 3.86 (s, 3H), 6.96-7.00 (m, 2H), 7.20-7.23 (m, 1H), 7.26-7.31 (m, 2H), 7.44-7.48 (m, 2H), 7.98 (s, 1H). MS (ESI) m/z: 242 [M−H]$^+$.

Intermediate 12. 5-(4-Fluorophenyl)-3H-1,3-benzoxazol-2-one

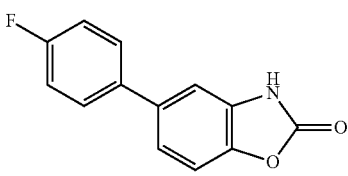 [SMILES: O=c1[nH]c2cc(-c3ccc(F)cc3)ccc2o1]

The title compound was obtained according to the General Procedure III, starting from 5-bromobenzoxazolone (80 mg, 0.374 mmol) and (4-fluorophenyl)boronic acid (78 mg, 0.561 mmol). In total, two microwave cycles were applied using fresh palladium catalyst and boronic acid each time. Title compound was obtained as a white solid (26.0 mg, 30%). $^1$H NMR (400 MHz, CDCl$_3$) δ 7.11-7.16 (m, 2H), 7.19-7.21 (m, 1H), 7.25-7.28 (m, 2H), 7.45-7.51 (m, 2H), 7.97 (s, 1H). MS (ESI) m/z: 228 [M−H]$^-$.

Intermediate 13. 6-Phenyl-3H-1,3-benzoxazol-2-one

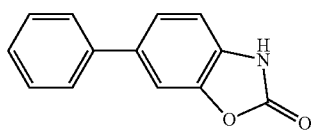 [SMILES: O=c1[nH]c2ccc(-c3ccccc3)cc2o1]

The title compound was obtained according to the General Procedure III, starting from 6-bromobenzoxazolone (80 mg, 0.374 mmol) and phenylboronic acid (68 mg, 0.561 mmol). White solid (29.1 mg, 37%). $^1$H NMR (400 MHz, CDCl$_3$) δ 7.11 (d, J=8.1 Hz, 1H), 7.33-7.41 (m, 2H), 7.42-7.47 (m, 3H), 7.53-7.56 (m, 2H), 7.98 (s, 1H). MS (ESI) m/z: 212 [M−H]$^+$. [For analytical data of title compound, see also: Fukaya T et al., *Bioorg. Med. Chem.*, 2012, 20, 5568-5582].

Intermediate 14. 6-(4-Methoxyphenyl)-3H-1,3-benzoxazol-2-one

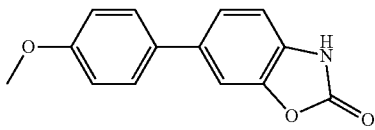 [SMILES: COc1ccc(-c2ccc3[nH]c(=O)oc3c2)cc1]

The title compound was obtained according to the General Procedure III, starting from 6-bromobenzoxazolone (80 mg, 0.374 mmol) and (4-methoxyphenyl)boronic acid (85 mg, 0.561 mmol). White solid (36.0 mg, 40%). $^1$H NMR (400 MHz, CDCl$_3$) δ 3.86 (s, 3H), 6.96-7.00 (m, 2H), 7.07 (d, J=8.1 Hz, 1H), 7.34 (dd, J=8.1, 1.6 Hz, 1H), 7.39 (d, J=1.3 Hz, 1H), 7.46-7.49 (m, 2H), 7.73 (s, 1H). MS (ESI) m/z: 240 [M−H]$^-$.

Intermediate 15. 6-(4-Fluorophenyl)-3H-1,3-benzoxazol-2-one

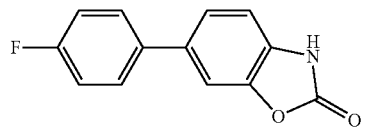

The title compound was obtained according to the General Procedure III, starting from 6-bromobenzoxazolone (80 mg, 0.374 mmol) and (4-fluorophenyl)boronic acid (78 mg, 0.561 mmol). White solid (34.6 mg, 40%). $^1$H NMR (400

MHz, CDCl₃) δ 7.08 (m, 3H), 7.33 (dd, J=8.1, 1.6 Hz, 1H), 7.39 (d, J=1.4 Hz, 1H), 7.47-7.52 (m, 2H), 7.91 (s, 1H). MS (ESI) m/z: 228 [M−H]⁻.

Intermediate 16. 4-Phenyl-3H-1,3-benzoxazol-2-one

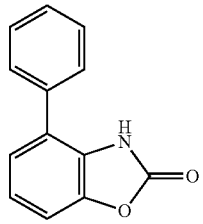 [SMILES: O=c1[nH]c2c(-c3ccccc3)cccc2o1]

The title compound was obtained according to the General Procedure III, starting from 4-bromobenzoxazolone (160 mg, 0.75 mmol) and phenylboronic acid (137 mg, 1.125 mmol). In total, three microwave cycles were applied using fresh palladium catalyst and boronic acid each time. Compound was obtained as a white solid after two purifications by column chromatography, but still only in low purity (~70% by UPLC and NMR; Impurities were triphenylphosphine oxide and 4-bromobenzoxazolone). Yield is therefore reported as crude yield of 95 mg (61%). ¹H NMR (400 MHz, CDCl₃) δ 7.10-7.30 (m, 3H), 7.40-7.47 (m, 1H), 7.47-7.57 (m, 4H), 8.24 (s, 1H). MS (ESI) m/z: 210 [M−H]⁻. [For analytical data of title compound, see also: Fukaya T et al., *Bioorg. Med. Chem.*, 2012, 20, 5568-5582].].

Intermediate 17. 7-Phenyl-3H-1,3-benzoxazol-2-one

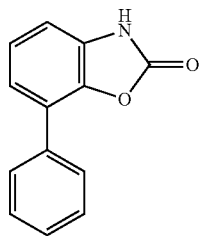 [SMILES: O=c1[nH]c2cccc(-c3ccccc3)c2o1]

The title compound was obtained according to the General Procedure III, starting from 7-bromobenzoxazolone (Intermediate 9; 160 mg, 0.75 mmol) and phenylboronic acid (137 mg, 1.125 mmol). In total, eight microwave cycles were applied using fresh palladium catalyst and boronic acid each time to get full consumption of starting material (important for the following step). Crude title compound was obtained as an orange solid (399 mg) after two purifications by column chromatography, first with cyclohexane:EtOAc as eluents and second with DCM/20% MeOH in DCM. However, purity was low (~30% by UPLC and NMR), as title compound was isolated together with triphenylphosphine oxide and derivatives of the phenylboronic acid. Still, the compound was successfully used in the subsequent step without further purifications. MS (ESI) m/z: 210 [M−H]⁻.

Intermediate 18. 6-[(E)-Styryl]-3H-1,3-benzoxazol-2-one

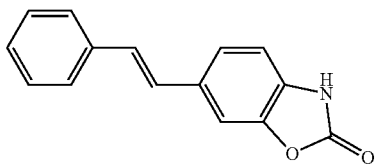 [SMILES: O=c1[nH]c2ccc(/C=C/c3ccccc3)cc2o1]

The title compound was obtained according to the General Procedure IV, starting from 6-bromobenzoxazolone (160 mg, 0.750 mmol) and [(E)-styryl]boronic acid (166 mg, 1.122 mmol). White solid (131.2 mg, 74%). ¹H NMR (400 MHz, CDCl₃) δ 7.03 (d, J=8.1 Hz, 1H), 7.07 (d, J=6.4 Hz, 1H), 7.26-7.31 (m, 3H), 7.32-7.44 (m, 3H), 7.47-7.53 (m, 2H), 7.98 (s, 1H). MS (ESI) m/z: 236 [M−H]⁻.

Intermediate 19. 6-[(E)-2-Cyclohexylvinyl]-3H-1,3-benzoxazol-2-one

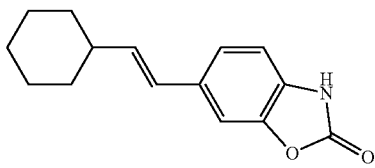 [SMILES: O=c1[nH]c2ccc(/C=C/C3CCCCC3)cc2o1]

The title compound was obtained according to the General Procedure IV, starting from 6-bromobenzoxazolone (160 mg, 0.750 mmol) and [(E)-2-cyclohexylvinyl]boronic acid (172 mg, 1.122 mmol). White solid (102.8 mg, 56%). ¹H NMR (400 MHz, CDCl₃) δ 1.13-1.35 (m, 6H), 1.64-1.83 (m, 4H), 2.07-2.17 (m, 1H), 6.11 (dd, J=15.9, 6.9 Hz, 1H), 6.32 (d, J=16.0 Hz, 1H), 6.95 (d, J=8.1 Hz, 1H), 7.10 (dd, J=8.1, 1.6 Hz, 1H), 7.23 (d, J=1.5 Hz, 1H), 7.92 (s, 1H). MS (ESI) m/z: 244 [M−H]⁺.

Intermediate 20. 6-Phenethyl-3H-1,3-benzoxazol-2-one

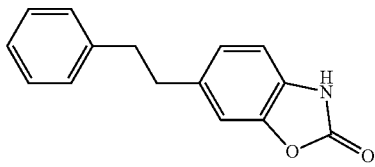 [SMILES: O=c1[nH]c2ccc(CCc3ccccc3)cc2o1]

The title compound was obtained according to the General Procedure V, starting from Intermediate 18 (48.2 mg, 0.203 mmol). White solid (48.4 mg, 100%). ¹H NMR (400 MHz, CDCl₃) δ 2.88-2.99 (m, 4H), 6.94 (br s, 2H), 7.02 (br s, 1H), 7.12-7.24 (m, 3H), 7.27-7.32 (m, 2H), 8.30 (s, 1H). MS (ESI) m/z: 240 [M−H]⁺.

Intermediate 21.
6-(2-Cyclohexylethyl)-3H-1,3-benzoxazol-2-one

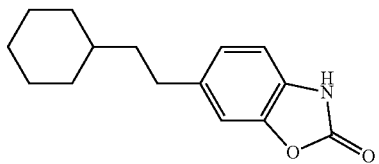 [SMILES: O=c1[nH]c2ccc(CCC3CCCCC3)cc2o1]

The title compound was obtained according to the General Procedure V, starting from Intermediate 19 (42 mg, 0.173 mmol). White solid (42.5 mg, 100%). $^1$H NMR (400 MHz, CDCl$_3$) δ 0.86-0.99 (m, 2H), 1.10-1.30 (m, 4H), 1.44-1.53 (m, 2H), 1.61-1.79 (m, 5H), 2.60-2.66 (m, 2H), 6.91-6.97 (m, 2H), 7.04 (br s, 1H), 7.87 (br s, 1H). MS (ESI) m/z: 246 [M–H]$^+$.

Intermediate 22. 6-[Tert-butyl(diphenyl)silyl]oxy-3H-1,3-benzoxazol-2-one

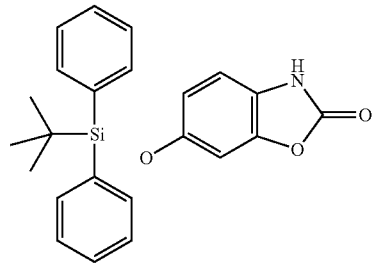

Imidazole (0.128 g, 1.875 mmol) and tert-butyldiphenylsilyl chloride (TBDPSCl, 0.412 g, 0.390 mL, 1.5 mmol) were added to a solution of 6-hydroxy-3H-1,3-benzoxazol-2-one (0.189 mg, 1.25 mmol) in MeCN/DCM (1:1, 6 mL) at room temperature. The resulting light-brown slurry was stirred for 1.5 hour at which point the reaction had turned white. The reaction was quenched with sat. aq. NH$_4$Cl (20 mL) and diluted with EtOAc (10 mL), followed by separation of the two phases. The organic phase was washed with brine (20 mL), dried over Na$_2$SO$_4$, and concentrated by vacuum. Pure compound was obtained by column chromatography. Clear colorless thick oil (291.3 mg, 60%). $^1$H NMR (400 MHz, CDCl$_3$) δ 1.10 (s, 9H), 6.55 (dd, J=8.5, 2.3 Hz, 1H), 6.66 (d, J=2.3 Hz, 1H), 6.71 (d, J=8.5 Hz, 1H), 7.34-7.40 (m, 4H), 7.41-7.47 (m, 2H), 7.67-7.71 (m, 4H), 7.92 (br s, 1H). MS (ESI) m/z: 388 [M–H]$^-$.

Intermediate 23. 6-[Tert-butyl(diphenyl)silyl]oxy-3-(2-methoxyethoxymethyl)-1,3-benzoxazol-2-one

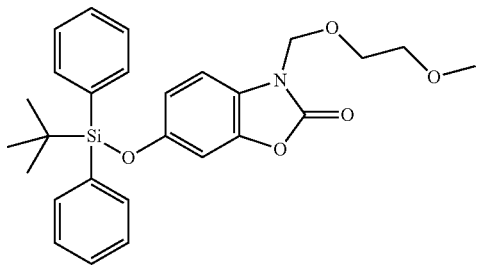 [SMILES: COCCOCn1c(=O)oc2cc(O[Si](c3ccccc3)(c3ccccc3)C(C)(C)C)ccc21]

To a solution of Intermediate 22 (1.8 g, 4.61 mmol) in DMF (14 mL), K$_2$CO$_3$ (1.92 g, 13.9 mmol) was added. The reaction was stirred at 80° C. for 1 hour and 2-methoxyethoxymethyl chloride (13.9 mmol, 1.58 mL) was added, whereby the red solution turned into a light-orange slurry. The solution was stirred for 1.5 hour at 80° C., quenched with aq. sat. NH$_4$Cl (40 mL) and diluted with EtOAc (60 mL). Water (20 mL) was added to obtain clear phases, and the organic phase was washed with water (60 mL), dried over Na$_2$SO$_4$, and evaporated. Pure title compound was obtained by column chromatography (cyclohexane:EtOAc) as a clear colorless oil (1.59 g, 72%). $^1$H NMR (400 MHz, CDCl$_3$) δ 1.43 (s, 9H), 3.30 (s, 3H), 3.46-3.50 (m, 2H), 3.66-3.71 (m, 2H), 5.23 (s, 2H), 6.59 (dd, J=8.5, 2.3 Hz, 1H), 6.66 (d, J=2.3 Hz, 1H), 6.84 (d, J=8.5 Hz, 1H), 7.34-7.40 (m, 4H), 7.41-7.47 (m, 2H), 7.68-7.72 (m, 4H). MS (ESI) m/z: 478 [M–H]$^+$.

Intermediate 24. 6-Hydroxy-3-(2-methoxyethoxymethyl)-1,3-benzoxazol-2-one

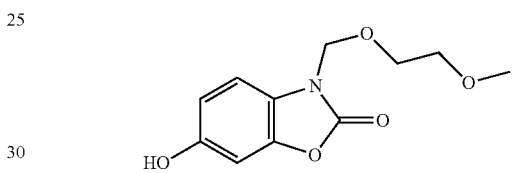

Intermediate 23 (1.59 g, 3.33 mmol) was treated with TBAF (1 M solution in THF, 25 mL, 25 mmol) for 30 min at room temperature. The solution was evaporated, co-evaporated twice with diethyl ether, and evaporated to dryness on a celite/silica mixture using EtOAc. Pure title product was obtained by column chromatography (DCM: 20% MeOH in DCM) as a white solid (752 mg, 95%). $^1$H NMR (400 MHz, DMSO-d$_6$) δ 3.19 (s, 3H), 3.40-3.43 (m, 2H), 3.60-3.63 (m, 2H), 5.22 (s, 2H), 6.64 (dd, J=8.5, 2.3 Hz, 1H), 6.78 (d, J=2.2 Hz, 1H), 7.11 (d, J=8.4 Hz, 1H), 9.52 (s, 1H). MS (ESI) m/z: 240 [M–H]$^+$.

Intermediate 25. 6-Butoxy-3-(2-methoxyethoxymethyl)-1,3-benzoxazol-2-one

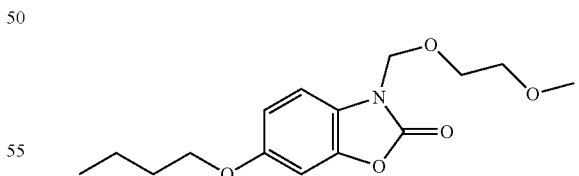

The title compound was obtained according to the General Procedure VI (Step 1), starting from Intermediate 24 (168 mg, 0.702 mmol) and 1-buthanol (104 mg, 1.404 mmol). Clear colorless oil (143 mg, 69%). $^1$H NMR (400 MHz, CDCl$_3$) δ 0.98 (t, J=7.4 Hz, 3H), 1.44-1.55 (m, 2H), 1.71-1.81 (m, 2H), 3.34 (s, 3H), 3.49-3.53 (m, 2H), 3.70-3.74 (m, 2H), 3.94 (t, J=6.5 Hz, 2H), 5.30 (s, 2H), 6.74 (d, J=8.5 Hz, 1H), 6.82-6.84 (m, 1H), 7.04 (d, J=8.5 Hz, 1H). MS (ESI) m/z: 296 [M–H]$^+$.

Intermediate 26. 6-(2-Cyclohexylethoxy)-3-(2-methoxyethoxymethyl)-1,3-benzoxazol-2-one

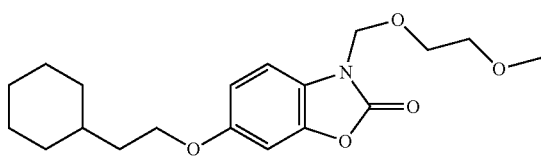 [SMILES: COCCOCn1c(=O)oc2cc(OCCC3CCCCC3)ccc21]

The title compound was obtained according to the General Procedure VI (Step 1), starting from Intermediate 24 (168 mg, 0.702 mmol) and 2-cyclohexylethanol (180 mg, 1.404 mmol). Clear colorless oil (225 mg, 92%). $^1$H NMR (400 MHz, CDCl$_3$) δ 0.89-1.00 (m, 2H), 1.08-1.27 (m, 4H), 1.56-1.76 (m, 7H), 3.34 (s, 3H), 3.50-3.53 (m, 2H), 3.70-3.74 (m, 2H), 3.97 (t, J=6.7 Hz, 2H), 5.31 (s, 2H), 6.73 (dd, J=8.6, 2.4 Hz, 1H), 6.83 (d, J=2.3 Hz, 1H), 7.04 (d, J=8.6 Hz, 1H). MS (ESI) m/z: 350 [M−H]$^+$.

Intermediate 27. 3-(2-Methoxyethoxymethyl)-6-phenethyloxy-1,3-benzoxazol-2-one

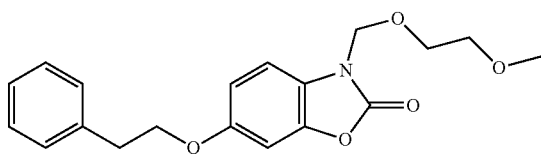 [SMILES: COCCOCn1c(=O)oc2cc(OCCc3ccccc3)ccc21]

The title compound was obtained according to the General Procedure VI (Step 1), starting from Intermediate 24 (168 mg, 0.702 mmol) and 2-phenylethanol (172 mg, 1.404 mmol). Clear colorless oil (191 mg, 79%). $^1$H NMR (400 MHz, CDCl$_3$) δ 3.10 (t, J=7.0 Hz, 2H), 3.33 (s, 3H), 3.49-3.52 (m, 2H), 3.69-3.73 (m, 2H), 4.16 (t, J=7.0 Hz, 2H), 5.30 (s, 2H), 6.73 (dd, J=8.5, 2.2 Hz, 1H), 6.83 (d, J=2.3 Hz, 1H), 7.04 (d, J=8.6 Hz, 1H), 7.22-7.35 (m, 5H). MS (ESI) m/z: 344 [M−H]$^+$.

Intermediate 28. 6-Butoxy-3-(hydroxymethyl)-1,3-benzoxazol-2-one

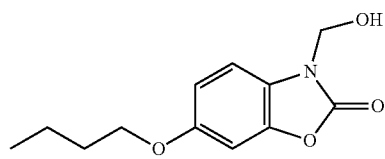 [SMILES: CCCCOc1ccc2c(c1)oc(=O)n2CO]

The title compound was obtained according to the General Procedure VI (Step 2), starting from Intermediate 25 (143 mg, 0.484 mmol). White solid (73 mg, 63%). $^1$H NMR (400 MHz, CDCl$_3$) δ 0.98 (t, J=7.4 Hz, 3H), 1.44-1.55 (m, 2H), 1.64-1.88 (m, 3H), 3.94 (t, J=6.5 Hz, 2H), 5.35 (s, 2H), 6.74-6.78 (m, 1H), 6.84 (br s, 1H), 7.03 (d, J=8.6 Hz, 1H). MS (ESI) m/z: 238 [M−H]$^+$.

Intermediate 29. 6-(2-Cyclohexylethoxy)-3-(hydroxymethyl)-1,3-benzoxazol-2-one

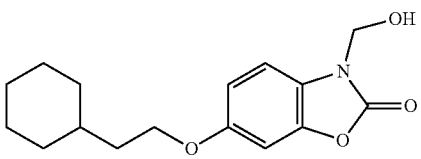 [SMILES: O=c1oc2cc(OCCC3CCCCC3)ccc2n1CO]

The title compound was obtained according to the General Procedure VI (Step 2), starting from Intermediate 26 (225 mg, 0.644 mmol). White solid (89 mg, 48%). $^1$H NMR (400 MHz, DMSO-d$_6$) δ 0.86-1.01 (m, 2H), 1.06-1.27 (m, 3H), 1.39-1.51 (m, 1H), 1.55-1.76 (m, 7H), 3.98 (t, J=6.7 Hz, 2H), 5.17 (s, 2H), 6.65 (br s, 1H), 6.81 (dd, J=8.6, 2.4 Hz, 1H), 7.05 (d, J=2.4 Hz, 1H), 7.20 (d, J=8.6 Hz, 1H). MS (ESI) m/z: 292 [M−H]$^+$.

Intermediate 30. 3-(Hydroxymethyl)-6-phenethyloxy-1,3-benzoxazol-2-one

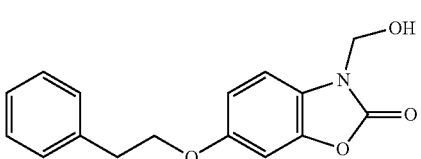

The title compound was obtained according to the General Procedure VI (Step 2), starting from Intermediate 27 (191 mg, 0.557 mmol). White solid (102 mg, 64%). $^1$H NMR (400 MHz, DMSO-d$_6$) δ 3.03 (t, J=6.9 Hz, 2H), 4.19 (t, J=6.9 Hz, 2H), 5.16 (s, 1H), 5.18 (s, 1H), 6.64 (t, J=7.3 Hz, 1H), 6.82 (dd, J=8.6, 2.4 Hz, 1H), 7.07 (d, J=2.4 Hz, 1H), 7.20 (d, J=8.6 Hz, 1H), 7.30-7.35 (m, 5H). MS (ESI) m/z: 286 [M−H]$^+$.

Intermediate 31. 6-Butoxy-3H-1,3-benzoxazol-2-one

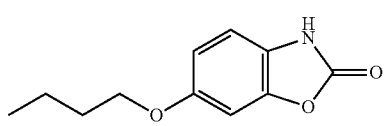

The title compound was obtained according to the General Procedure VI (Step 3), starting from Intermediate 28 (73 mg, 0.307 mmol). White solid (49 mg, 77%). $^1$H NMR (400 MHz, CDCl$_3$) δ 0.98 (t, J=7.4 Hz, 3H), 1.43-1.55 (m, 2H), 1.72-1.81 (m, 2H), 3.94 (t, J=6.5 Hz, 2H), 6.71 (dd, J=8.6, 2.4 Hz, 1H), 6.83 (d, J=2.3 Hz, 1H), 6.93 (d, J=8.6 Hz, 1H), 8.30 (s, 1H). MS (ESI) m/z: 208 [M−H]$^+$.

Intermediate 32.
6-(2-Cyclohexylethoxy)-3H-1,3-benzoxazol-2-one

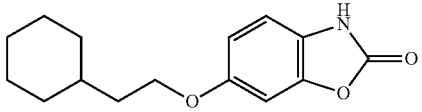 [SMILES: O=c1[nH]c2ccc(OCCC3CCCCC3)cc2o1]

The title compound was obtained according to the General Procedure VI (Step 3), starting from Intermediate 29 (76 mg, 0.262 mmol). White solid (50 mg, 72%). $^1$H NMR (400 MHz, CDCl$_3$) δ 0.91-1.03 (m, 2H), 1.10-1.33 (m, 3H), 1.44-1.54 (m, 1H), 1.62-1.80 (m, 7H), 3.96 (t, J=6.7 Hz, 2H), 6.70 (dd, J=8.6, 2.4 Hz, 1H), 6.82 (d, J=2.3 Hz, 1H), 6.92 (d, J=8.6 Hz, 1H), 8.10 (s, 1H). MS (ESI) m/z: 262 [M−H]$^+$.

Intermediate 33.
6-Phenethyloxy-3H-1,3-benzoxazol-2-one

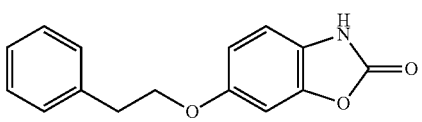 [SMILES: O=c1[nH]c2ccc(OCCc3ccccc3)cc2o1]

The title compound was obtained according to the General Procedure VI (Step 3), starting from Intermediate 30 (98 mg, 0.344 mmol). White solid (65 mg, 74%). $^1$H NMR (400 MHz, CDCl$_3$) δ 3.10 (t, J=7.0 Hz, 2H), 4.15 (t, J=7.0 Hz, 2H), 6.70 (dd, J=8.6, 2.4 Hz, 1H), 6.82 (d, J=2.2 Hz, 1H), 6.92 (d, J=8.5 Hz, 1H), 7.35-7.22 (m, 5H), 8.21 (s, 1H). MS (ESI) m/z: 254 [M−H]$^+$.

Intermediate 34.
6-Propanoyl-3H-1,3-benzoxazol-2-one

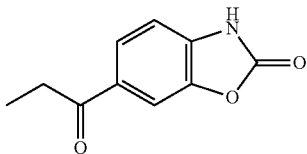

The title compound was obtained according to the General Procedure VII (Step 1-2). See literature (Ucar H et al., *Tetrahedron*, 1998, 54, 1763-1772) for procedure and analytical data of title compound.

Intermediate 35.
6-Benzoyl-3H-1,3-benzoxazol-2-one

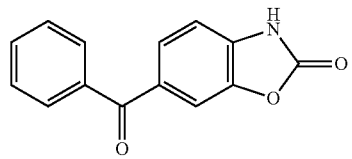 [SMILES: O=C(c1ccccc1)c1ccc2[nH]c(=O)oc2c1]

The title compound was obtained according to the General Procedure VII (Step 1-2). See literature (Ucar H et al., *Tetrahedron*, 1998, 54, 1763-1772) for procedure and analytical data of title compound.

Intermediate 36.
6-(4-Chlorobenzoyl)-3H-1,3-benzoxazol-2-one

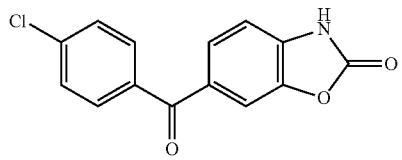 [SMILES: O=C(c1ccc(Cl)cc1)c1ccc2[nH]c(=O)oc2c1]

The title compound was obtained according to the General Procedure VII (Step 1-2). See literature (Ucar H et al., *Tetrahedron*, 1998, 54, 1763-1772) for procedure and analytical data of title compound.

Intermediate 37. 4-cyclohexylbutan-1-amine hydrochloride

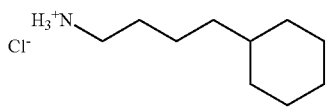

The title compound was obtained according to the General Procedure VIII (Step 1-2). See literature (Więcek M et al., *Bioorg. Med. Chem.*, 2011, 19, 2850-2858) for procedure and analytical data of title compound.

Intermediate 38. 2-[(4-Propylcyclohexyl)methyl] isoindoline-1,3-dione

In an oven-dried flask, LiAlH$_4$ (2 M in THF, 17.6 mL, 35 mmol) was dissolved in dry THF (45 mL). The solution was cooled to 0° C. and the commercially available trans-4-(prop-1-yl)cyclohexane carboxylic acid (1.5 g, 8.81 mmol), dissolved in dry THF was added dropwise. The reaction mixture was stirred under nitrogen at room temperature for 5 hours. The reaction was then cooled to 0° C. and H$_2$O (0.5 mL) was added dropwise, followed by aq. KOH (3 M, 0.5 mL) and H$_2$O (1.5 mL). The mixture was stirred for 1 hour at 0° C. and filtered to remove the solid residue; the organic phase dried over Na$_2$SO$_4$ and the solvent was evaporated under reduced pressure to afford the crude (4-propylcyclohexyl)methanol (1.15 g), as colorless oil. The crude alcohol was used without further purification in the next step (Scheme 3, Step 1). $^1$H NMR (400 MHz, DMSO-d$_6$) δ 0.80-0.88 (m, 7H), 1.10-1.18 (m, 3H), 1.23-1.33 (m, 3H), 1.64-1.79 (m, 4H), 3.18 (t, J=5.52 Hz, 2H), 4.30 (t, J=5.52 Hz, 1H).

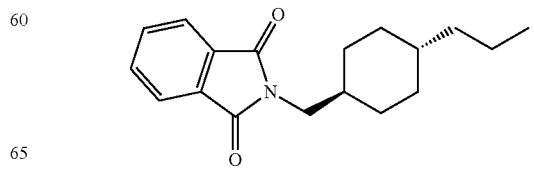

The title compound was obtained according to the General Procedure VIII (Step 1), starting from the crude (4-propylcyclohexyl)methanol (1.15 g, 7.35 mmol). White powder (1.56 g, 62% over two steps). ¹H NMR (400 MHz, DMSO-d₆) δ 0.80-0.88 (m, 7H), 1.10-1.18 (m, 3H), 1.23-1.33 (m, 3H), 1.64-1.79 (m, 4H), 3.46 (d, J=5.52 Hz, 2H), 7.75-7.95 (m, 4H). MS (ESI) m/z: 286 [M−H]⁺.

Intermediate 39. (4-Propylcyclohexyl)methanamine hydrochloride

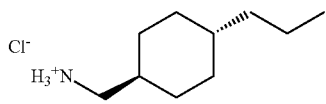

The title compound was obtained according to the General Procedure VIII (Step 2), starting from intermediate 38 (1.56 g, 5.46 mmol). White powder (1.19 g, crude). ¹H NMR (400 MHz, DMSO-d₆) δ 0.85 (t, J=7.3 Hz, 3H), 0.89-1.01 (m, 3H), 1.07-1.21 (m, 4H), 1.23-1.35 (m, 2H), 1.41-1.58 (m, 1H), 1.65-1.86 (m, 4H), 2.56-2.68 (m, 2H). MS (ESI) m/z: 156 [M−H]⁺.

Intermediate 40. 2-[(4-Propylphenyl)methyl]isoindoline-1,3-dione (4-Propylphenyl)methanol was obtained from the corresponding commercially available 4-propyl benzoic acid (700 mg, 4.26 mmol) according to the procedure described for Intermediate 38. The crude alcohol (520 mg) was obtained as colorless oil and it was used without further purification in the next step (Scheme 3, Step 1). ¹H NMR (400 MHz, DMSO-d₆) δ 0.88 (t, J=7.3 Hz, 3H), 1.45-1.72 (m, 2H), 2.51-2.57 (m, 2H), 4.45 (d, J=5.6 Hz, 2H), 5.07 (t, J=5.4 Hz, 1H), 7.13 (d, J=8.0 Hz, 2H), 7.17-7.28 (m, 2H).

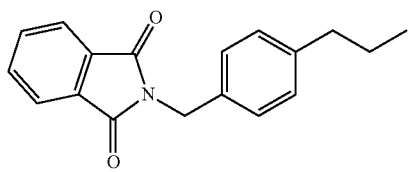 [SMILES: CCCc1ccc(CN2C(=O)c3ccccc3C2=O)cc1]

The title compound was obtained according to the General Procedure VIII (Step 1), starting from (4-propylphenyl)methanol (520 mg, 3.46 mmol). Pale yellow solid (750 mg, 63% over two steps). ¹H NMR (400 MHz, DMSO-d₆) δ 0.86 (t, J=7.3 Hz, 3H), 1.46-1.64 (m, 2H), 2.47-2.53 (m, 2H), 4.73 (s, 2H), 7.10-7.17 (m, 2H), 7.17-7.24 (m, 2H), 7.60-8.22 (m, 4H). MS (ESI) m/z: 280 [M−H]⁺.

Intermediate 41. (4-Propylphenyl)methanamine hydrochloride

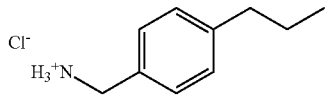

The title compound was obtained according to the General Procedure VIII (Step 2), starting from Intermediate 40 (720 mg, 2.58 mmol). White powder (280 mg, crude). ¹H NMR (400 MHz, DMSO-d₆) δ 0.88 (t, J=7.3 Hz, 3H), 1.49-1.67 (m, 2H), 2.52-2.62 (m, 2H), 3.97 (q, J=5.9 Hz, 2H), 7.17-7.31 (m, 2H), 7.29-7.49 (m, 2H). MS (ESI) m/z: 150 [M−H]⁺.

Intermediate 42. 2-[4-(2-Thienyl)butyl]isoindoline-1,3-dione 4-(2-Thienyl)butan-1-ol was obtained from the corresponding commercially available 4-(2-thienyl)butanoic acid (851 mg, 5 mmol) according to the procedure described for Intermediate 38. The crude alcohol (770 mg) was obtained as orange clear oil and it was used without further purification in the next step (Scheme 3, Step 1). ¹H NMR (400 MHz, DMSO-d₆) δ 1.41-1.50 (m, 2H), 1.58-1.68 (m, 2H), 2.79 (td, J=7.6, 1.0 Hz, 2H), 3.41 (td, J=6.5, 5.2 Hz, 2H), 4.37 (t, J=5.2 Hz, 1H), 6.82-6.84 (m, 1H), 6.92 (dd, J=5.1, 3.4 Hz, 1H), 7.29 (dd, J=5.1, 1.2 Hz, 1H). m/z: 157 [M−H]⁺.

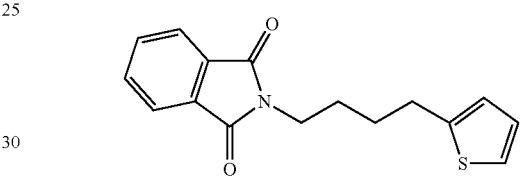

The title compound was obtained according to the General Procedure VIII (Step 1), starting from 4-(2-thienyl)butan-1-ol (769 mg, 4.92 mmol). White solid (1.086 g, 76% over two steps). ¹H NMR (400 MHz, CDCl₃) δ 1.68-1.81 (m, 4H), 2.88 (t, J=6.8 Hz, 2H), 3.72 (t, J=6.7 Hz, 2H), 6.78 (d, J=3.3 Hz, 1H), 6.90 (dd, J=5.0, 3.5 Hz, 1H), 7.09 (d, J=4.9 Hz, 1H), 7.71 (dd, J=5.4, 3.1 Hz, 2H), 7.84 (dd, J=5.4, 3.1 Hz, 2H). MS (ESI) m/z: 286 [M−H]⁺. [For analytical data of title compound, see also: Dowle M D et al., *Synthesis*, 1983, 1, 73-75].

Intermediate 43. 4-(2-Thienyl)butan-1-amine hydrochloride

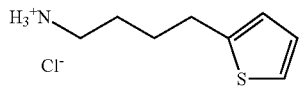

The title compound was obtained according to the General Procedure VIII (Step 2), starting from intermediate 42 (1.086 g, 3.805 mmol). White solid (642 mg, crude). ¹H NMR (400 MHz, DMSO-d₆) δ 1.54-1.71 (m, 4H), 2.73-2.85 (m, 4H), 6.85-6.88 (m, 1H), 6.94 (dd, J=5.1, 3.4 Hz, 1H), 7.31 (dd, J=5.1, 1.2 Hz, 1H), 7.91 (br s, 3H). MS (ESI) m/z: 156 [M−H]⁺.

Intermediate 44. 2-[4-(4-Methoxyphenyl)butyl]isoindoline-1,3-dione

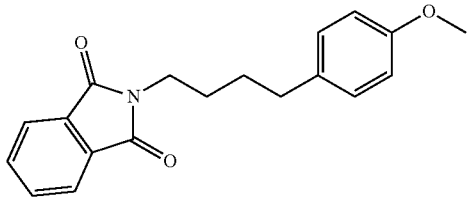 [SMILES: COc1ccc(CCCCN2C(=O)c3ccccc3C2=O)cc1]

The title compound was obtained according to the General Procedure VIII (Step 1), starting from the corresponding commercially available 4-(4-methoxyphenyl)butan-1-ol (887 mg, 4.923 mmol). White solid (1.17 g, 77%). $^1$H NMR (400 MHz, CDCl$_3$) δ 1.59-1.76 (m, 4H), 2.60 (t, J=7.4 Hz, 2H), 3.70 (t, J=7.0 Hz, 2H), 3.77 (s, 3H), 6.81 (d, J=8.5 Hz, 2H), 7.08 (d, J=8.5 Hz, 2H), 7.70 (dd, J=5.5, 3.0 Hz, 2H), 7.83 (dd, J=5.4, 3.1 Hz, 2H). MS (ESI) m/z: 310 [M−H]$^+$. [For analytical data of title compound, see also: Apelt J et al., *J. Med. Chem.* 2002, 45, 1128-1141].

Intermediate 45. 4-(4-Methoxyphenyl)butan-1-amine hydrochloride

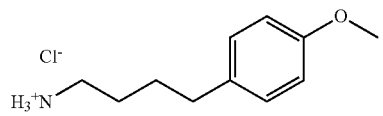

The title compound was obtained according to the General Procedure VIII (Step 2). See literature (Shang G et al., *Chemistry—A European Journal*, 2007, 13, 7780-7784) for procedure and analytical data of title compound.

Intermediate 46. 2-[4-(4-Fluorophenyl)butyl]isoindoline-1,3-dione 4-(4-Fluorophenyl)butan-1-ol was obtained from the corresponding commercially available 4-(4-fluorophenyl) butanoic acid (800 mg, 4.39 mmol) according to the procedure described for Intermediate 38. The crude alcohol (730 mg) was obtained as colorless oil and it was used without further purification in the next step (Scheme 3, Step 1). $^1$H NMR (400 MHz, DMSO-d$_6$) δ 1.33-1.49 (m, 2H), 1.51-1.65 (m, 2H), 2.56 (t, J=7.6 Hz, 2H), 3.40 (td, J=6.5, 5.1 Hz, 2H), 4.36 (t, J=5.2 Hz, 1H), 7.03-7.13 (m, 2H), 7.17-7.25 (m, 2H). [For analytical data of 4-(4-fluorophenyl)butan-1-ol, see also: Ganellin C et al, *Archiv der Pharmazie*, 1998, 331, 395-404].

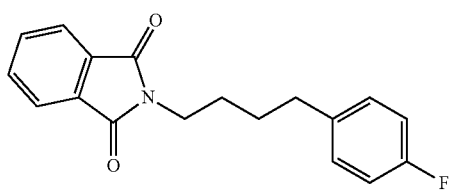 [SMILES: O=C1c2ccccc2C(=O)N1CCCCc1ccc(F)cc1]

The title compound was obtained according to the General Procedure VIII (Step 1), starting from 4-(4-Fluorophenyl)butan-1-ol (730 mg, 4.34 mmol). White solid (920 mg, 70% over two steps). $^1$H NMR (400 MHz, DMSO-d$_6$) δ 1.41-1.73 (m, 4H), 2.58 (t, J=7.2 Hz, 2H), 3.59 (t, J=6.6 Hz, 2H), 6.97-7.14 (m, 2H), 7.14-7.31 (m, 2H), 7.73-7.98 (m, 4H). MS (ESI) m/z: 296 [M−H]$^−$. [For analytical data of title compound, see also: Ganellin C et al, *Archiv der Pharmazie*, 1998, 331, 395-404].

Intermediate 47. 4-(4-Fluorophenyl)butan-1-amine hydrochloride

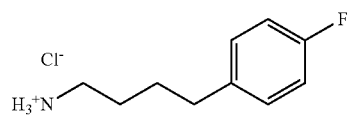

The title compound was obtained according to the General Procedure VIII (Step 2), starting from intermediate 46 (920 mg, 3.10 mmol). Pale yellow solid (450 mg, crude). $^1$H NMR (400 MHz, DMSO-d$_6$) δ 1.44-1.68 (m, 4H), 2.57 (t, J=7.1 Hz, 2H), 2.69-2.85 (m, 2H), 7.01-7.14 (m, 2H), 7.18-7.29 (m, 2H). MS (ESI) m/z: 168 [M−H]$^+$. [For analytical data of title compound, see also: Ganellin C et al, *Archiv der Pharmazie*, 1998, 331, 395-404].

Intermediate 48. 2-[4-(p-Tolyl)butyl]isoindoline-1,3-dione 4-(p-Tolyl)butan-1-ol was obtained from the corresponding commercially available 4-(p-tolyl) butanoic acid (800 mg, 4.49 mmol) according to the procedure described for Intermediate 38. The crude alcohol (570 mg) was obtained as colorless oil and it was used without further purification in the next step (Scheme 3, Step 1). $^1$H NMR (400 MHz, DMSO-d$_6$) δ 1.34-1.48 (m, 2H), 1.49-1.61 (m, 2H), 2.24 (s, 3H), 2.47-2.58 (m, 2H), 3.36-3.46 (m, 2H), 4.34 (t, J=5.2 Hz, 1H), 7.06 (s, 4H). [For analytical data of 4-(p-tolyl)butan-1-ol, see also: Jackman L M et al., *J. Am. Chem. Soc.*, 1974, 96, 5130-5138].

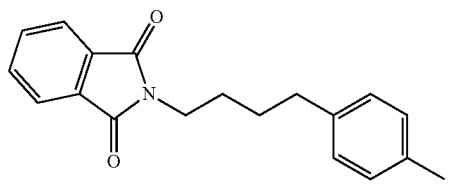 [SMILES: Cc1ccc(CCCCN2C(=O)c3ccccc3C2=O)cc1]

The title compound was obtained according to the General Procedure VIII (Step 1), starting from 4-(p-tolyl)butan-1-ol (570 mg, 3.47 mmol). White solid (680 mg, 52% over two steps). $^1$H NMR (400 MHz, DMSO-d$_6$) δ 1.46-1.66 (m, 4H), 2.23 (s, 3H), 2.54 (t, J=7.3 Hz, 2H), 3.58 (t, J=6.7 Hz, 2H), 7.05 (s, 4H), 7.71-8.00 (m, 4H). MS (ESI) m/z: 294 [M−H]$^+$, 311 [M−NH$_4$]$^+$.

Intermediate 49. 4-(p-Tolyl)butan-1-amine hydrochloride

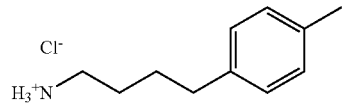

The title compound was obtained according to the General Procedure VIII (Step 2), starting from intermediate 48 (680 mg, 2.33 mmol). Pale yellow solid (370 mg, crude). $^1$H NMR (400 MHz, DMSO-$d_6$) δ 1.32-1.79 (m, 4H), 2.25 (s, 3H), 2.54 (t, J=7.2 Hz, 2H), 2.77 (q, J=6.6 Hz, 2H), 7.08 (s, 4H). MS (ESI) m/z: 164 [M−H]$^+$.

Intermediate 50. 2-[4-(4-Nitrophenyl)butyl]isoindoline-1,3-dione

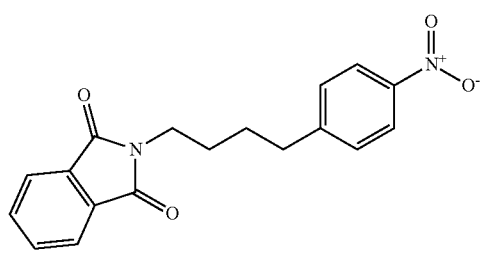 [SMILES: O=C1c2ccccc2C(=O)N1CCCCc1ccc([N+](=O)[O-])cc1]

The title compound was obtained according to the General Procedure VIII (Step 1), starting from commercially available 4-(4-nitrophenyl)butan-1-ol (500 mg, 2.56 mmol). White solid (535 mg, 64%). $^1$H NMR (400 MHz, CDCl$_3$) δ 1.63-1.79 (m, 4H), 2.77 (t, J=7.1 Hz, 2H), 3.72 (t, J=6.5 Hz, 2H), 7.32 (d, J=8.2 Hz, 2H), 7.68-7.78 (m, 2H), 7.80-7.90 (m, 2H), 8.12 (d, J=8.1 Hz, 2H). MS (ESI) m/z: 325 [M−H]$^+$.

Intermediate 51. 4-(4-Nitrophenyl)butan-1-amine hydrochloride

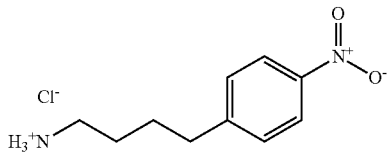

The title compound was obtained according to the General Procedure VIII (Step 2), starting from intermediate 50 (535 mg, 1.649 mmol). White solid (380 mg, crude). $^1$H NMR (400 MHz, DMSO-$d_6$) δ 1.52-1.61 (m, 2H), 1.61-1.71 (m, 2H), 2.71-2.83 (m, 4H), 7.49-7.54 (m, 2H), 7.97 (br s, 3H), 8.14-8.19 (m, 2H). MS (ESI) m/z: 195 [M−H]$^+$.

Intermediate 52. 2-[3-(3-Pyridyl)propyl]isoindoline-1,3-dione

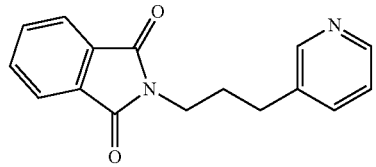 [SMILES: O=C1c2ccccc2C(=O)N1CCCc1cccnc1]

The title compound was obtained according to the General Procedure VIII (Step 1), starting from commercially available 3-(3-pyridyl)propan-1-ol (405 mg, 2.953 mmol). Title compound (606 mg, 77%) was isolated as a 1:1 mixture (NMR) with triphenylphosphine oxide (630 mg) as a white solid, and was used like this in the following step. $^1$H NMR (400 MHz, CDCl$_3$) δ 1.99-2.09 (m, 2H), 2.70 (t, J=7.9 Hz, 2H), 3.76 (t, J=7.1 Hz, 2H), 7.20-7.24 (m, 1H), 7.69-7.75 (m, 2H), 7.52-7.57 (m, 1H), 7.81-7.87 (m, 2H), 8.40-8.48 (m, 2H). MS (ESI) m/z: 267 [M−H]$^+$. [For analytical data of title compound, see also: Mayer J M, Testa B, *Helvetica Chimica Acta*, 1982, 65, 1868-1884].

Intermediate 53. 3-(3-Pyridyl)propan-1-amine dihydrochloride

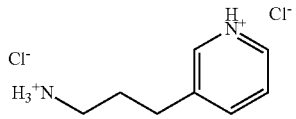

The title compound was obtained according to the General Procedure VIII (Step 2), starting from intermediate 52 (399 mg, 1.498 mmol). Pure compound was obtained by additional extractions, as compound was taken up in water (40 mL) and DCM (30 mL), the two phases separated, and the aqueous phase washed with DCM (9×20 mL). The aqueous phase was lyophilized to afford intermediate 53 (292 mg, 93%). $^1$H NMR (400 MHz, DMSO-$d_6$) δ 1.96 (p, J=7.5 Hz, 2H), 2.73-2.83 (m, 2H), 2.91 (t, J=7.6 Hz, 2H), 8.02 (dd, J=8.0, 5.6 Hz, 1H), 8.21 (br s, 3H), 8.51 (dt, J=8.2, 1.7 Hz, 1H), 8.80 (d, J=5.3 Hz, 1H), 8.89 (d, J=1.6 Hz, 1H). MS (ESI) m/z: 137 [M−H]$^+$. [For analytical data of title compound, see also: Mayer J M, Testa B, *Helvetica Chimica Acta*, 1982, 65, 1868-1884].

Intermediate 54. 2-[3-(3-Fluorophenyl)propyl]isoindoline-1,3-dione 3-(3-Fluorophenyl)propan-1-ol was obtained from the corresponding commercially available 3-(3-fluorophenyl)propanoic acid (505 mg, 3 mmol) according to the procedure described for Intermediate 38. The crude alcohol (455 mg) was obtained as a colorless clear oil and it was used without further purification in the next step (Scheme 3, Step 1). $^1$H NMR (400 MHz, DMSO-$d_6$) δ 1.66-1.73 (m, 2H), 2.60-2.65 (m, 2H), 3.40 (td, J=6.4, 5.1 Hz, 2H), 4.47 (t, J=5.1 Hz, 1H), 6.94-7.05 (m, 3H), 7.27-7.34 (m, 1H).

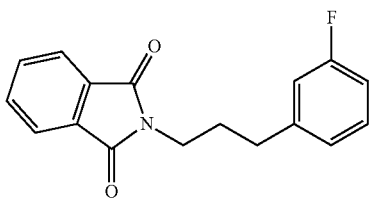 [SMILES: O=C1c2ccccc2C(=O)N1CCCc1cccc(F)c1]

The title compound was obtained according to the General Procedure VIII (Step 1), starting from 3-(3-fluorophenyl)propan-1-ol (455 mg, 2.953 mmol). White solid (603 mg, 71% over two steps). $^1$H NMR (400 MHz, CDCl$_3$) δ 1.99-2.08 (m, 2H), 2.68 (t, J=7.8 Hz, 2H), 3.74 (t, J=7.1 Hz, 2H), 6.82 (td, J=8.5, 2.6 Hz, 1H), 6.90 (dt, J=10.0, 2.1 Hz, 1H), 6.97 (d, J=7.7 Hz, 1H), 7.20 (td, J=7.9, 6.1 Hz, 1H), 7.71 (dd, J=5.5, 3.1 Hz, 2H), 7.83 (dd, J=5.4, 3.1 Hz, 2H). MS (ESI) m/z: 282 [M–H]$^+$.

Intermediate 55. 3-(3-Fluorophenyl)propan-1-amine hydrochloride

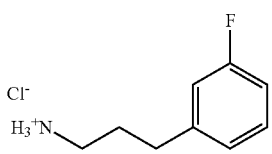

The title compound was obtained according to the General Procedure VIII (Step 2), starting from intermediate 54 (603 mg, 2.129 mmol). Yellow solid (354 mg, crude). $^1$H NMR (400 MHz, DMSO-d$_6$) δ 1.82-1.91 (m, 2H), 2.68 (t, J=7.6 Hz, 2H), 2.72-2.79 (m, 2H), 6.99-7.11 (m, 3H), 7.34 (td, J=8.1, 6.3 Hz, 1H), 8.06 (br s, 3H). MS (ESI) m/z: 154 [M–H]$^+$. [For analytical data of title compound, see also: Banister S D et al., Bioorg. Med. Chem. Lett., 2012, 22, 6053-6058].

Intermediate 56. 2-[3-(2-Chlorophenyl)propyl]isoindoline-1,3-dione 3-(2-chlorophenyl)propan-1-ol was obtained from the corresponding commercially available 2-chloro-benzenepropanoic acid (0.8 g, 4.33 mmol) according to the procedure described for Intermediate 38. The crude alcohol (0.55 g) was obtained as colorless oil and it was used without further purification in the next step (Scheme 3, Step 1). $^1$H NMR (400 MHz, DMSO-d$_6$) δ 1.63-1.78 (m, 2H), 2.67-2.78 (m, 2H), 3.43 (td, J=6.5, 5.2 Hz, 2H), 4.53 (t, J=5.1 Hz, 1H), 7.22 (dd, J=7.6, 2.0 Hz, 1H), 7.26 (td, J=7.4, 1.5 Hz, 1H), 7.33 (dd, J=7.5, 1.9 Hz, 1H), 7.39 (dd, J=7.7, 1.5 Hz, 1H). [For analytical data of title compound, see also: Houghton R P et al., J. Chem. Res. Miniprint, 1989, 8, 1872-1892.]

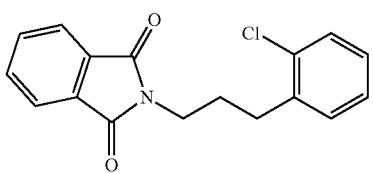 [SMILES: O=C1c2ccccc2C(=O)N1CCCc1ccccc1Cl]

The title compound was obtained according to the General Procedure VIII (Step 1), starting from 3-(2-chlorophenyl)propan-1-ol (0.55 g, 3.22 mmol). White solid (0.55 g, 42% over two steps). $^1$H NMR (400 MHz, DMSO-d$_6$) δ 1.83-1.98 (m, 2H), 2.67-2.77 (m, 2H), 3.64 (t, J=7.1 Hz, 2H), 7.18-7.30 (m, 2H), 7.38 (dt, J=7.4, 1.6 Hz, 2H), 7.80-7.90 (m, 4H). MS (ESI) m/z: 300 [M–H]$^+$.

Intermediate 57. 3-(2-Chlorophenyl)propan-1-amine hydrochloride

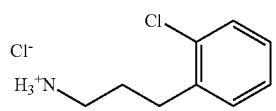

The title compound was obtained according to the General Procedure VIII (Step 2), starting from intermediate 56 (0.55 g, 1.83 mmol). White solid (0.22 g, crude). $^1$H NMR (400 MHz, DMSO-d$_6$) δ 1.85 (tt, J=9.4, 6.3 Hz, 2H), 2.78 (s, 2H), 2.82 (dt, J=8.6, 5.8 Hz, 2H), 7.09-7.60 (m, 4H). MS (ESI) m/z: 170 [M–H]$^+$. [For analytical data of title compound, see also: Gautier F-M et al, Org. Biomol. Chem., 2011, 9, 7860-7868].

Intermediate 58. 2-[4-(2-Naphthyl)butyl]isoindoline-1,3-dione 4-(2-Naphthyl)butan-1-ol was obtained from the corresponding commercially available methyl 4-(2-naphthyl)butanoate (250 mg, 1.10 mmol) according to the procedure described for Intermediate 38. The crude alcohol (200 mg) was obtained as brown oil and it was used without further purification in the next step (Scheme 3, Step 1). $^1$H NMR (400 MHz, DMSO-d$_6$) δ 1.37-1.57 (m, 2H), 1.62-1.76 (m, 2H), 2.75 (t, J=7.6 Hz, 2H), 3.43 (td, J=6.5, 5.1 Hz, 2H), 4.36 (t, J=5.2 Hz, 1H), 7.36-7.50 (m, 3H), 7.67-7.69 (m, 1H), 7.80-7.88 (m, 3H). [For analytical data of title compound, see also: Lee T and Jones J B, J. Am. Chem. Soc. 1997, 119, 10260-10268].

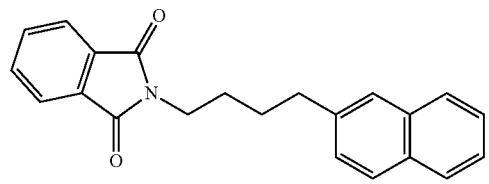 [SMILES: O=C1c2ccccc2C(=O)N1CCCCc1ccc2ccccc2c1]

The title compound was obtained according to the General Procedure VIII (Step 1), starting from 4-(2-naphthyl)butan-1-ol (200 mg, 0.99 mmol). White solid (133 mg, 37% over two steps). $^1$H NMR (400 MHz, DMSO-d$_6$) δ 1.57-1.74 (m, 4H), 2.77 (t, J=7.0 Hz, 2H), 3.58-3.70 (m, 2H), 7.32-7.52 (m, 3H), 7.67 (d, J=1.8 Hz, 1H), 7.77-7.89 (m, 7H).

Intermediate 59. 4-(2-Naphthyl)butan-1-amine hydrochloride

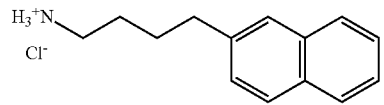

The title compound was obtained according to the General Procedure VIII (Step 2), starting from intermediate 58 (133 mg, 0.40 mmol). Pale yellow solid (68 mg, crude). $^1$H NMR (400 MHz, DMSO-$d_6$) δ 1.52-1.64 (m, 2H), 1.65-1.80 (m, 2H), 2.78 (t, J=7.4 Hz, 2H), 2.80-2.86 (m, 2H), 7.35-7.55 (m, 3H), 7.70 (d, J=1.6 Hz, 1H), 7.80-7.93 (m, 3H). MS (ESI) m/z: 200 [M−H]$^+$.

Intermediate 60. 6-(Tert-butyl-cyclohexa-2,4-dien-1-yl-phenyl-silyl)oxy-2-oxo-N-(4-phenylbutyl)-1,3-benzoxazole-3-carboxamide

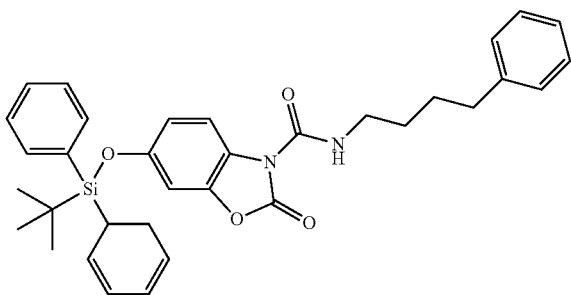 [SMILES: CC(C)(C)[Si](Oc1ccc2c(c1)oc(=O)n2C(=O)NCCCCc1ccccc1)(c1ccccc1)C1C=CC=CC1]

The title compound was obtained according to the General Procedure I (Method A), starting from Intermediate 22 (291 mg, 0.748 mmol) and 4-phenylbutyl isocyanate (144 mg, 0.141 mL, 0.823 mmol). Clear colorless oil (366 mg, 87%). $^1$H NMR (400 MHz, CDCl$_3$) δ 1.11 (s, 9H), 1.60-1.73 (m, 4H), 2.65 (t, J=7.2 Hz, 2H), 3.40 (q, J=6.6 Hz, 2H), 6.63 (d, J=2.4 Hz, 1H), 6.67 (dd, J=8.7, 2.4 Hz, 1H), 7.14-7.20 (m, 3H), 7.24-7.30 (m, 2H), 734-7.40 (m, 4H), 7.41-7.47 (m, 2H), 7.67-7.71 (m, 4H), 7.73 (d, J=8.7 Hz, 1H), 7.95 (t, J=5.8 Hz, 1H). MS (ESI) m/z: 565 [M−H]$^+$.

Intermediate 61. 4-Fluoro-3H-1,3-benzoxazol-2-one

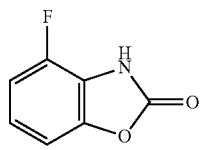

The title compound was obtained according to the General Procedure II, starting from 2-amino-3-fluoro-phenol (63.6 mg, 0.50 mmol). Orange solid (73 mg, 95%). $^1$H NMR (400 MHz, CDCl$_3$) δ 6.98 (ddd, J=9.5, 8.1, 1.5 Hz, 1H), 7.04-7.13 (m, 2H), 9.63 (s, 1H). MS (ESI) m/z: 152 [M−H]$^−$.

Intermediate 62. 2-(5-Phenylpentyl)isoindoline-1,3-dione

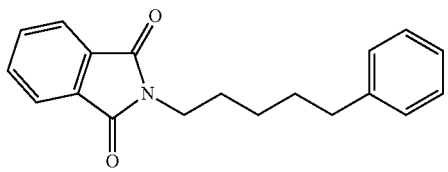 [SMILES: O=C1c2ccccc2C(=O)N1CCCCCc1ccccc1]

In an oven-dried flask, phthalimide (736 mg, 5.0 mmol), 5-bromopentylbenzene (1.14 g, 5.0 mmol) and K$_2$CO$_3$ (691 mg, 5.0 mmol) were dissolved in dry DMF (10 mL) and the solution was stirred under nitrogen at room temperature for 15 hours. EtOAc (20 mL) was added, the precipitate was filtered off and the filtrate was evaporated leaving the crude product which was used in the following step without further purification.

Intermediate 63. 5-Phenylhexan-1-amine hydrochloride

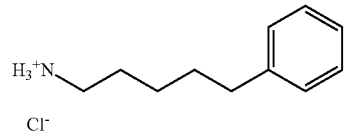

The title compound was obtained according to the General Procedure VIII (Step 2), starting from intermediate 62. Colourless solid (807 mg, 81% over two steps). $^1$H NMR (400 MHz, CDCl$_3$) δ 1.38-1.51 (m, 2H), 1.60-1.72 (m, 2H), 1.75-1.88 (m, 2H), 2.62 (t, J=7.6 Hz, 2H), 2.94-3.03 (m, 2H), 7.13-7.21 (m, 3H), 7.25-7.31 (m, 2H), 8.27 (s, 3H). MS (ESI) m/z: 164 [M−H]$^+$.

Intermediate 64. 6-Phenylhexan-1-amine hydrochloride

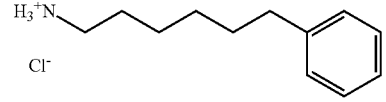

The title compound was obtained according to the General Procedure VIII (Step 1-2). See literature (Butini S et al., *J. Med. Chem*, 2012, 55, 6898-6915) for procedure and analytical data of title compound.

The following Examples provide embodiments illustrative of the present invention.

Example 1

2-Oxo-N-(4-phenylbutyl)-1,3-benzoxazole-3-carboxamide

The title compound was obtained according to the General Procedure I (Method A), starting from 3H-1,3-benzoxazol-2-one (50 mg, 0.37 mmol) and 4-phenylbutyl isocyanate (104 mg, 0.59 mmol). White solid (95 mg, 83%). $^1$H NMR (400 MHz, DMSO-$d_6$) δ 1.47-1.74 (m, 4H), 2.61 (t, J=7.21 Hz, 2H), 3.34 (q, J=6.81 Hz, 2H), 7.04-7.33 (m, 7H), 7.37-7.47 (m, 1H), 7.84-7.95 (m, 1H), 8.14 (t, J=5.80 Hz, 1H). $^{13}$C NMR (101 MHz, DMSO-$d_6$) δ 28.61, 29.06, 35.22, 39.94, 110.39, 114.99, 124.58, 124.95, 126.13, 126.21, 128.70, 128.76, 141.99, 142.50, 149.81, 152.65. MS (ESI) m/z: 311 [M−H]$^+$.

Example 2

5-Fluoro-2-oxo-N-(4-phenylbutyl)-1,3-benzoxazole-3-carboxamide

The title compound was obtained according to the General Procedure I (Method A), starting from 5-fluoro-3H-1, 3-benzoxazol-2-one (61 mg, 0.400 mmol) and 4-phenylbutyl isocyanate (77 mg, 0.075 mL, 0.44 mmol). White solid (111 mg, 85%). $^1$H NMR (400 MHz, CDCl$_3$) δ 1.64-1.78 (m, 4H), 2.67 (t, J=7.1 Hz, 2H), 3.44 (q, J=6.6 Hz, 2H), 6.94 (td, J=9.0, 2.7 Hz, 1H), 7.15-7.21 (m, 4H), 7.26-7.31 (m, 2H), 7.85 (dd, J=8.5, 2.7 Hz, 1H), 8.01 (t, J=6.3 Hz, 1H). $^{13}$C NMR (101 MHz, CDCl$_3$) δ 28.64, 29.11, 35.55, 40.29, 104.28 (d, J=31.3 Hz), 110.52 (d, J=9.5 Hz), 111.18 (d, J=25.1 Hz), 126.01, 128.50 (4C), 128.67 (d, J=14.0 Hz), 137.80 (d, J=2.2 Hz), 141.95, 149.52, 153.40, 159.81 (d, J=242.4 Hz). MS (ESI) m/z: 327 [M−H]$^+$.

Example 3

6-Fluoro-2-oxo-N-(4-phenylbutyl)-1,3-benzoxazole-3-carboxamide

The title compound was obtained according to the General Procedure I (Method A), starting from 6-fluoro-3H-1,3-benzoxazol-2-one (51 mg, 0.334 mmol) and 4-phenylbutyl isocyanate (64 mg, 0.063 mL, 0.367 mmol). White solid (87 mg, 79%). $^1$H NMR (400 MHz, CDCl$_3$) δ 1.63-1.78 (m, 4H), 2.67 (t, J=7.2 Hz, 2H), 3.44 (td, J=6.7, 5.6 Hz, 2H), 6.96-7.04 (m, 2H), 7.16-7.21 (m, 3H), 7.25-7.31 (m, 2H), 7.96 (t, J=5.7 Hz, 1H), 8.00-8.05 (m, 1H). $^{13}$C NMR (101 MHz, CDCl$_3$) δ 28.66, 29.14, 35.56, 40.27, 99.12 (d, J=28.8 Hz), 111.82 (d, J=23.4 Hz), 116.32 (d, J=9.0 Hz), 124.35 (d, J=2.6 Hz), 126.01, 128.50 (4C), 141.85, 141.97 (d, J=2.3 hz), 149.65, 153.16, 159.73 (d, J=245.2 Hz). MS (ESI) m/z: 329 [M−H]$^+$.

Example 4

5-Chloro-2-oxo-N-(4-phenylbutyl)-1,3-benzoxazole-3-carboxamide

The title compound was obtained according to the General Procedure I (Method A), starting from 5-chloro-3H-1,3-benzoxazol-2-one (68 mg, 0.400 mmol) and 4-phenylbutyl isocyanate (77 mg, 0.075 mL, 0.44 mmol). Clear colorless oil (127 mg, 92%). $^1$H NMR (400 MHz, CDCl$_3$) δ 1.64-1.79 (m, 4H), 2.67 (t, J=7.1 Hz, 2H), 3.44 (td, J=6.7, 5.5 Hz, 2H), 7.13-7.24 (m, 5H), 7.26-7.31 (m, 2H), 7.98 (t, J=5.2 Hz, 1H), 8.12 (d, J=2.1 Hz, 1H). $^{13}$C NMR (101 MHz, CDCl$_3$) δ 28.67, 29.14, 35.58, 40.36, 110.84, 116.27, 124.71, 126.05, 128.54 (4C), 128.89, 130.76, 140.32, 141.98, 149.51, 153.05. MS (ESI) m/z: 345 [M−H]$^+$.

Example 5

6-Chloro-2-oxo-N-(4-phenylbutyl)-1,3-benzoxazole-3-carboxamide

The title compound was obtained according to the General Procedure I (Method A), starting from 6-chloro-3H-1,3-benzoxazol-2-one (56 mg, 0.334 mmol) and 4-phenylbutyl isocyanate (64 mg, 0.063 mL, 0.367 mmol). White solid (77 mg, 67%). $^1$H NMR (400 MHz, CDCl$_3$) δ 1.64-1.78 (m, 4H), 2.67 (t, J=7.2 Hz, 2H), 3.44 (td, J=6.7, 5.6 Hz, 2H), 7.16-7.20 (m, 3H), 7.24-7.31 (m, 4H), 7.93-8.02 (m, 2H). $^{13}$C NMR (101 MHz, CDCl$_3$) δ 28.68, 29.15, 35.58, 40.33, 110.93, 116.44, 125.36, 126.06, 126.84, 128.54 (4C), 130.24, 141.97, 142.06, 149.57, 152.88. MS (ESI) m/z: 168 [M−CONH(CH$_2$)$_4$Ph]$^−$.

Example 6

5-Bromo-2-oxo-N-(4-phenylbutyl)-1,3-benzoxazole-3-carboxamide

The title compound was obtained according to the General Procedure I (Method A), starting from 5-bromo-3H-1,3-benzoxazol-2-one (100 mg, 0.467 mmol) and 4-phenylbutyl isocyanate (90 mg, 0.088 mL, 0.514 mmol). White solid (88 mg, 48%). $^1$H NMR (400 MHz, CDCl$_3$) δ 1.64-1.77 (m, 4H), 2.67 (t, J=7.2 Hz, 2H), 3.44 (td, J=6.8, 5.6 Hz, 2H), 7.11 (d, J=8.6 Hz, 1H), 7.16-7.21 (m, 3H), 7.26-7.31 (m, 2H), 7.37 (dd, J=8.6, 2.1 Hz, 1H), 7.97 (t, J=4.6 Hz, 1H), 8.27 (d, J=2.0 Hz, 1H). $^{13}$C NMR (101 MHz, CDCl$_3$) δ 28.67, 29.14, 35.58, 40.37, 111.30, 117.91, 118.98, 126.05, 127.62, 128.54 (4C), 129.17, 140.82, 141.97, 149.49, 152.88. MS (ESI) m/z: 212 and 214 [M−CONH(CH$_2$)$_4$Ph]$^−$.

Example 7

6-Bromo-2-oxo-N-(4-phenylbutyl)-1,3-benzoxazole-3-carboxamide

The title compound was obtained according to the General Procedure I (Method A), starting from 6-bromo-3H-1,3-benzoxazol-2-one (100 mg, 0.47 mmol) and 4-phenylbutyl isocyanate (90 mg, 0.088 mL, 0.51 mmol). White solid (149 mg, 82%). $^1$H NMR (400 MHz, CDCl$_3$) δ 1.64-1.74 (m, 4H), 2.67 (t, J=7.2 Hz, 2H), 3.44 (td, J=6.8, 5.7 Hz, 2H), 7.16-7.20 (m, 3H), 7.26-7.30 (m, 2H), 7.39-7.42 (m, 2H), 7.95 (d, J=9.0 Hz, 1H), 7.93-7.97 (m, 1H). $^{13}$C NMR (101 MHz, CDCl$_3$) δ 28.68, 29.15, 35.58, 40.34, 100.15, 113.65, 116.87, 117.20, 126.06, 128.24, 128.54 (4C), 141.97, 142.21, 149.55, 152.74. MS (ESI) m/z: 212 and 214 [M−CONH(CH$_2$)$_4$Ph]$^−$.

Example 8

5-Methyl-2-oxo-N-(4-phenylbutyl)-1,3-benzoxazole-3-carboxamide

The title compound was obtained according to the General Procedure I (Method A), starting from 5-methyl-3H-1,3-benzoxazol-2-one (50 mg, 0.334 mmol) and 4-phenylbutyl isocyanate (64 mg, 0.063 mL, 0.367 mmol). White solid (99 mg, 91%). $^1$H NMR (400 MHz, CDCl$_3$) δ 1.64-1.77 (m, 4H), 2.41 (s, 3H), 2.67 (t, J=7.2 Hz, 2H), 3.44 (td, J=6.7, 5.5 Hz, 2H), 7.00-7.04 (m, 1H), 7.08-7.11 (m, 1H), 7.16-7.21 (m, 3H), 7.26-7.30 (m, 2H), 7.90 (br s, 1H), 8.08 (t, J=4.9 Hz, 1H). $^{13}$C NMR (101 MHz, CDCl$_3$) δ 21.71, 28.71, 29.21, 35.61, 40.24, 109.51, 116.14, 125.04, 126.02, 128.03, 128.52 (2C), 128.55 (2C), 135.20, 139.91, 142.05, 150.13, 153.62. MS (ESI) m/z: 325 [M−H]$^+$.

Example 9

6-Methyl-2-oxo-N-(4-phenylbutyl)-1,3-benzoxazole-3-carboxamide

The title compound was obtained according to the General Procedure I (Method A), starting from 6-methyl-3H-1,3-benzoxazol-2-one (50 mg, 0.334 mmol) and 4-phenylbutyl isocyanate (64 mg, 0.063 mL, 0.367 mmol). White solid (73 mg, 68%). $^1$H NMR (400 MHz, CDCl$_3$) δ 1.63-1.78 (m, 4H), 2.41 (s, 3H), 2.67 (t, J=7.2 Hz, 2H), 3.44 (td, J=6.7, 5.5 Hz, 2H), 7.03-7.08 (m, 2H), 7.15-7.21 (m, 3H), 7.26-7.30 (m, 2H), 7.89-7.92 (m, 1H), 8.04 (t, J=5.4 Hz, 1H). $^{13}$C NMR (101 MHz, CDCl$_3$) δ 21.60, 28.72, 29.22, 35.61, 40.23, 110.51, 115.25, 125.63, 125.73, 126.02, 128.52 (2C), 128.55 (2C), 134.99, 141.97, 142.06, 150.05, 153.49. MS (ESI) m/z: 325 [M−H]$^+$.

Example 10

6-Methoxy-2-oxo-N-(4-phenylbutyl)-1,3-benzoxazole-3-carboxamide

The title compound was obtained according to the General Procedure I (Method A), starting from 6-methoxy-3H-1,3-benzoxazol-2-one (77 mg, 0.467 mmol) and 4-phenylbutyl isocyanate (90 mg, 0.088 mL, 0.514 mmol). White solid (143 mg, 90%). $^1$H NMR (400 MHz, CDCl$_3$) δ 1.63-1.78 (m, 4H), 2.67 (t, J=7.2 Hz, 2H), 3.44 (td, J=6.8, 5.6 Hz, 2H), 3.82 (s, 3H), 6.79 (d, J=2.5 Hz, 1H), 6.80-6.83 (m, 1H), 7.16-7.20 (m, 3H), 7.26-7.30 (m, 2H), 7.93 (d, J=8.7 Hz, 1H), 7.99 (t, J=4.4 Hz, 1H). $^{13}$C NMR (101 MHz, CDCl$_3$) δ 28.71, 29.23, 35.61, 40.23, 56.08, 97.08, 110.48, 116.03, 121.61, 126.02, 128.52 (2C), 128.55 (2C), 142.06, 142.62, 150.01, 153.51, 157.39. MS (ESI) m/z: 341 [M−H]$^+$.

Example 11

5-Nitro-2-oxo-N-(4-phenylbutyl)-1,3-benzoxazole-3-carboxamide

The title compound was obtained according to the General Procedure I (Method A), starting from Intermediate 1 (124 mg, 0.688 mmol) and 4-phenylbutyl isocyanate (133 mg, 0.130 mL, 0.757 mmol). White solid (150 mg, 61%). $^1$H NMR (400 MHz, CDCl$_3$) δ 1.65-1.79 (m, 4H), 2.68 (t, J=7.1 Hz, 2H), 3.47 (td, J=6.7, 5.6 Hz, 2H), 7.16-7.21 (m, 3H), 7.26-7.31 (m, 2H), 7.37 (d, J=8.9 Hz, 1H), 7.88 (t, J=5.3 Hz, 1H), 8.24 (dd, J=8.9, 2.4 Hz, 1H), 8.98 (d, J=2.4 Hz, 1H). $^{13}$C NMR (101 MHz, CDCl$_3$) δ 28.64, 29.08, 35.55, 40.52, 110.23, 112.03, 121.14, 126.08, 128.54 (2C), 128.54 (2C), 128.60, 141.89, 145.35, 145.60, 148.92, 152.60. MS (ESI) m/z: 354 [M−H]$^+$.

Example 12

6-Nitro-2-oxo-N-(4-phenylbutyl)-1,3-benzoxazole-3-carboxamide

The title compound was obtained according to the General Procedure I (Method A), starting from Intermediate 2 (72 mg, 0.40 mmol) and 4-phenylbutyl isocyanate (77 mg, 0.075 mL, 0.44 mmol). White solid (86 mg, 60%). $^1$H NMR (400 MHz, CDCl$_3$) δ 1.64-1.79 (m, 4H), 2.68 (t, J=7.0 Hz, 2H), 3.47 (q, J=6.4 Hz, 2H), 7.15-7.21 (m, 3H), 7.26-7.31 (m, 2H), 7.94 (t, J=5.8 Hz, 1H), 8.15 (t, J=1.2 Hz, 1H), 8.23-8.28 (m, 2H). $^{13}$C NMR (101 MHz, CDCl$_3$) δ 28.64, 29.05, 35.55, 40.54, 106.34, 115.64, 121.52, 126.11, 128.53 (2C), 128.56 (2C), 133.31, 141.35, 141.87, 144.75, 148.97, 152.69. MS (ESI) m/z: 179 [M−CONH(CH$_2$)$_4$Ph]$^-$.

Example 13

2-Oxo-N-(4-phenylbutyl)-5-(trifluoromethyl)-1,3-benzoxazole-3-carboxamide

The title compound was obtained according to the General Procedure I (Method A), starting from Intermediate 3 (128 mg, 0.630 mmol) and 4-phenylbutyl isocyanate (121 mg, 0.119 mL, 0.693 mmol). White solid (166 mg, 70%). $^1$H NMR (400 MHz, CDCl$_3$) δ 1.65 (m, 4H), 2.68 (t, J=7.1 Hz, 2H), 3.46 (q, J=6.5 Hz, 2H), 7.16-7.21 (m, 3H), 7.26-7.31 (m, 2H), 7.34 (d, J=8.5 Hz, 1H), 7.53-7.57 (m, 1H), 7.96 (t, J=5.7 Hz, 1H), 8.40 (d, J=1.9 Hz, 1H). $^{13}$C NMR (101 MHz, CDCl$_3$) δ 28.64, 29.10, 35.54, 40.39, 110.25, 113.46 (q, J=4.0 Hz), 122.21 (q, J=3.9 Hz), 123.78 (q, J=272.0 Hz), 126.03, 127.84 (q, J=33.3 Hz), 128.46, 128.51 (4C), 141.92, 143.82, 149.38, 152.80. MS (ESI) m/z: 379 [M−H]$^+$.

Example 14

2-Oxo-N-(4-phenylbutyl)-6-(trifluoromethyl)-1,3-benzoxazole-3-carboxamide

The title compound was obtained according to the General Procedure I (Method A), starting from Intermediate 4 (81 mg, 0.40 mmol) and 4-phenylbutyl isocyanate (77 mg, 0.075 mL, 0.44 mmol). White solid (91 mg, 60%). $^1$H NMR (400 MHz, CDCl$_3$) δ 1.64-1.79 (m, 4H), 2.68 (t, J=7.1 Hz, 2H), 3.46 (q, J=6.6 Hz, 2H), 7.15-7.21 (m, 3H), 7.26-7.31 (m, 2H), 7.51 (d, J=1.7 Hz, 1H), 7.55-7.59 (m, 1H), 7.98 (t, J=5.9 Hz, 1H), 8.20 (d, J=8.4 Hz, 1H). $^{13}$C NMR (101 MHz, CDCl$_3$) δ 28.65, 29.10, 35.56, 40.40, 107.56 (q, J=4.0 Hz), 115.94, 122.59 (q, J=3.9 Hz), 123.68 (q, J=272.1 Hz), 126.05, 127.24 (q, J=33.3 Hz), 128.52 (4C), 130.92, 141.57, 141.92, 149.35, 152.85. MS (ESI) m/z: 202 [M−CONH(CH$_2$)$_4$Ph]$^-$.

Example 15

5-Cyano-2-oxo-N-(4-phenylbutyl)-1,3-benzoxazole-3-carboxamide

The title compound was obtained according to the General Procedure I (Method A), starting from Intermediate 5 (102 mg, 0.637 mmol) and 4-phenylbutyl isocyanate (123 mg, 0.120 mL, 0.701 mmol). White solid (171 mg, 80%). $^1$H NMR (400 MHz, CDCl$_3$) δ 1.63-1.78 (m, 4H), 2.68 (t, J=7.1 Hz, 2H), 3.46 (q, J=6.4 Hz, 2H), 7.15-7.22 (m, 3H), 7.26-7.31 (m, 2H), 7.34 (d, J=8.4 Hz, 1H), 7.58 (dd, J=8.4, 1.7 Hz, 1H), 7.89 (t, J=5.7 Hz, 1H), 8.41 (d, J=1.7 Hz, 1H). $^{13}$C NMR (101 MHz, CDCl$_3$) δ 28.62, 29.07, 35.54, 40.47, 109.34, 111.05, 118.05, 119.50, 126.07, 128.53 (4C), 128.81, 129.57, 141.89, 144.42, 149.05, 152.35. MS (ESI) m/z: 159 [M−CONH(CH$_2$)$_4$Ph]$^-$.

Example 16

5,6-Dichloro-2-oxo-N-(4-phenylbutyl)-1,3-benzoxazole-3-carboxamide

The title compound was obtained according to the General Procedure I (Method A), starting from Intermediate 6 (121 mg, 0.593 mmol) and 4-phenylbutyl isocyanate (114 mg, 0.112 mL, 0.652 mmol). White solid (203 mg, 90%). $^1$H NMR (400 MHz, CDCl$_3$) δ 1.63-1.78 (m, 4H), 2.67 (t, J=7.1 Hz, 2H), 3.44 (td, J=6.7, 5.5 Hz, 2H), 7.16-7.21 (m, 3H), 7.26-7.31 (m, 2H), 7.37 (s, 1H), 7.84 (t, J=5.8 Hz, 1H), 8.22 (s, 1H). $^{13}$C NMR (101 MHz, CDCl$_3$) δ 28.65, 29.10, 35.56, 40.43, 112.04, 117.28, 126.08, 127.46, 128.54 (4C), 128.64, 129.35, 140.42, 141.92, 149.18, 152.57. MS (ESI) m/z: 202 [M−CONH(CH$_2$)$_4$Ph]$^-$.

Example 17

4-Methyl-2-oxo-N-(4-phenylbutyl)-1,3-benzoxazole-3-carboxamide

The title compound was obtained according to the General Procedure I (Method A), starting from Intermediate 7

(94 mg, 0.630 mmol) and 4-phenylbutyl isocyanate (121 mg, 0.119 mL, 0.693 mmol). Clear colorless oil (49 mg, 24%). $^1$H NMR (400 MHz, CDCl$_3$) δ 1.64-1.79 (m, 4H), 2.53 (s, 3H), 2.68 (t, J=7.2 Hz, 2H), 3.45 (q, J=6.6 Hz, 2H), 7.04-7.09 (m, 2H), 7.11-7.21 (m, 4H), 7.26-7.31 (m, 2H), 7.60 (t, J=4.5 Hz, 1H). $^{13}$C NMR (101 MHz, CDCl$_3$) δ 21.48, 28.65, 29.09, 35.59, 40.87, 107.65, 124.82, 126.01, 126.41, 126.64, 128.37, 128.52 (2C), 128.55 (2C), 142.06, 142.99, 149.33, 153.98. MS (ESI) m/z: 325 [M−H]$^+$.

Example 18

7-Methyl-2-oxo-N-(4-phenylbutyl)-1,3-benzoxazole-3-carboxamide

The title compound was obtained according to the General Procedure I (Method A), starting from Intermediate 8 (83 mg, 0.556 mmol) and 4-phenylbutyl isocyanate (107 mg, 0.105 mL, 0.612 mmol). White solid (128 mg, 71%). $^1$H NMR (400 MHz, CDCl$_3$) δ 1.63-1.78 (m, 4H), 2.39 (s, 3H), 2.67 (t, J=7.1 Hz, 2H), 3.44 (q, J=6.6 Hz, 2H), 7.04 (d, J=7.8 Hz, 1H), 7.12-7.20 (m, 4H), 7.26-7.31 (m, 2H), 7.88 (dd, J=8.0, 1.2 Hz, 1H), 8.09 (t, J=5.5 Hz, 1H). $^{13}$C NMR (101 MHz, CDCl$_3$) δ 14.54, 28.72, 29.21, 35.60, 40.25, 113.11, 120.51, 124.88, 126.01, 126.14, 127.76, 128.51 (2C), 128.55 (2C), 140.53, 142.05, 150.06, 153.49. MS (ESI) m/z: 325 [M−H]$^+$.

Example 19

7-Bromo-2-oxo-N-(4-phenylbutyl)-1,3-benzoxazole-3-carboxamide

The title compound was obtained according to the General Procedure I (Method A), starting from Intermediate 9 (140 mg, 0.654 mmol) and 4-phenylbutyl isocyanate (126 mg, 0.123 mL, 0.720 mmol). White solid (143 mg, 56%). $^1$H NMR (400 MHz, CDCl$_3$) δ 1.61-1.78 (m, 4H), 2.67 (t, J=7.1 Hz, 2H), 3.44 (q, J=6.4 Hz, 2H), 7.13-7.21 (m, 4H), 7.26-7.31 (m, 2H), 7.38 (dd, J=8.3, 1.1 Hz, 1H), 7.99 (t, J=6.0 Hz, 1H), 8.02 (dd, J=8.2, 1.0 Hz, 1H). $^{13}$C NMR (101 MHz, CDCl$_3$) δ 28.68, 29.13, 35.57, 40.38, 102.45, 114.68, 126.05, 126.19, 127.89, 128.54 (4C), 128.95, 140.05, 141.97, 149.58, 152.37. MS (ESI) m/z: 388 [M−H]$^+$.

Example 20

2-Oxo-5-phenyl-N-(4-phenylbutyl)-1,3-benzoxazole-3-carboxamide

The title compound was obtained according to the General Procedure I (Method A), starting from Intermediate 10 (14 mg, 0.071 mmol) and 4-phenylbutyl isocyanate (33 mg, 0.032 mL, 0.187 mmol). Clear colourless sticky oil (17 mg, 63%). $^1$H NMR (400 MHz, CDCl$_3$) δ 1.65-1.80 (m, 4H), 2.68 (t, J=7.1 Hz, 2H), 3.46 (q, J=6.4 Hz, 2H), 7.15-7.21 (m, 3H), 7.25-7.31 (m, 3H), 7.33-7.38 (m, 1H), 7.41-7.47 (m, 3H), 7.57-7.61 (m, 2H), 8.08 (t, J=5.3 Hz, 1H), 8.34 (d, J=1.9 Hz, 1H). $^{13}$C NMR (101 MHz, CDCl$_3$) δ 28.73, 29.21, 35.61, 40.31, 110.11, 114.56, 123.62, 126.03, 127.48 (2C), 127.75, 128.53 (2C), 128.55 (2C), 128.64, 129.00 (2C), 138.98, 140.41, 141.32, 142.04, 150.01, 153.51. MS (ESI) m/z: 210 [M−CONH(CH$_2$)$_4$Ph]$^−$.

Example 21

5-(4-Methoxyphenyl)-2-oxo-N-(4-phenylbutyl)-1,3-benzoxazole-3-carboxamide

The title compound was obtained according to the General Procedure I (Method A), starting from Intermediate 11 (41 mg, 0.170 mmol) and 4-phenylbutyl isocyanate (33 mg, 0.032 mL, 0.187 mmol). White solid (33 mg, 47%). $^1$H NMR (400 MHz, CDCl$_3$) δ 1.65-1.78 (m, 4H), 2.68 (t, J=7.1 Hz, 2H), 3.46 (q, J=6.6 Hz, 2H), 3.86 (s, 3H), 6.94-6.99 (m, 2H), 7.15-7.21 (m, 3H), 7.24-7.30 (m, 3H), 7.40 (dd, J=8.4, 1.9 Hz, 1H), 7.50-7.54 (m, 2H), 8.09 (t, J=5.3 Hz, 1H), 8.29 (d, J=1.8 Hz, 1H). $^{13}$C NMR (101 MHz, CDCl$_3$) δ 28.73, 29.21, 35.61, 40.30, 55.53, 110.05, 114.09, 114.43 (2C), 123.13, 126.03, 128.51 (2C), 128.52 (2C), 128.56 (2C), 128.61, 132.95, 138.63, 140.91, 142.04, 150.06, 153.55, 159.55. MS (ESI) m/z: 417 [M−H]$^+$.

Example 22

5-(4-Fluorophenyl)-2-oxo-N-(4-phenylbutyl)-1,3-benzoxazole-3-carboxamide

The title compound was obtained according to the General Procedure I (Method A), starting from Intermediate 12 (26 mg, 0.113 mmol) and 4-phenylbutyl isocyanate (33 mg, 0.032 mL, 0.187 mmol). White solid (26 mg, 58%). $^1$H NMR (400 MHz, CDCl$_3$) δ 1.64-1.78 (m, 4H), 2.68 (t, J=7.1 Hz, 2H), 3.46 (q, J=6.5 Hz, 2H), 7.09-7.16 (m, 2H), 7.17-7.21 (m, 3H), 7.26-7.31 (m, 3H), 7.39 (dd, J=8.4, 1.9 Hz, 1H), 7.51-7.57 (m, 2H), 8.07 ((t, J=5.5 Hz, 1H), 8.28 (d, J=1.9 Hz, 1H). $^{13}$C NMR (101 MHz, CDCl$_3$) δ 28.72, 29.20, 35.61, 40.33, 110.17, 114.45, 115.89 (d, J=21.5 Hz, 2C), 123.48, 126.04, 128.53 (2C), 128.55 (2C), 128.67, 129.07 (d, J=7.7 Hz, 2C), 136.53, 136.57, 141.29, 142.01, 149.99, 153.44, 162.78 (d, J=246.9 Hz). MS (ESI) m/z: 280 [M−CONH(CH$_2$)$_4$Ph]$^−$.

Example 23

2-Oxo-6-phenyl-N-(4-phenylbutyl)-1,3-benzoxazole-3-carboxamide

The title compound was obtained according to the General Procedure I (Method A), starting from Intermediate 13 (29 mg, 0.138 mmol) and 4-phenylbutyl isocyanate (29 mg, 0.028 mL, 0.165 mmol). White solid (33 mg, 62%). $^1$H NMR (400 MHz, CDCl$_3$) δ 1.65-1.79 (m, 4H), 2.68 (t, J=7.2 Hz, 2H), 3.47 (td, J=6.7, 5.6 Hz, 2H), 7.16-7.21 (m, 3H), 7.25-7.31 (m, 2H), 7.34-7.40 (m, 1H), 7.43-7.50 (m, 4H), 7.55-7.59 (m, 2H), 8.06 (t, J=5.3 Hz, 1H), 8.11 (d, J=8.4 Hz, 1H). $^{13}$C NMR (101 MHz, CDCl$_3$) δ 28.72, 29.22, 35.62, 40.31, 108.69, 115.81, 124.07, 126.04, 127.26 (2C), 127.32, 127.91, 128.54 (2C), 128.56 (2C), 129.13 (2C), 138.57, 140.05, 142.04, 142.43, 149.90, 153.41. MS (ESI) m/z: 387 [M−H]$^+$.

Example 24

6-(4-Methoxyphenyl)-2-oxo-N-(4-phenylbutyl)-1,3-benzoxazole-3-carboxamide

The title compound was obtained according to the General Procedure I (Method A), starting from Intermediate 14 (36 mg, 0.149 mmol) and 4-phenylbutyl isocyanate (29 mg, 0.028 mL, 0.165 mmol). White solid (52 mg, 84%). $^1$H NMR (400 MHz, CDCl₃) δ 1.65-1.78 (m, 4H), 2.68 (t, J=7.1 Hz, 2H), 3.46 (td, J=6.8, 5.6 Hz, 2H), 3.86 (s, 3H), 6.96-7.01 (m, 2H), 7.15-7.21 (m, 3H), 7.26-7.31 (m, 2H), 7.41 (d, J=1.5 Hz, 1H), 7.44 (dd, J=8.4, 1.7 Hz, 1H), 7.48-7.52 (m, 2H), 8.03-8.09 (m, 2H). ¹³C NMR (101 MHz, CDCl₃) δ 28.72, 29.22, 35.62, 40.29, 55.55, 108.23, 114.57 (2C), 115.75, 123.57, 126.03, 126.79, 128.30 (2C), 128.53 (2C), 128.56 (2C), 132.57, 138.25, 142.05, 142.46, 149.94, 153.44, 159.67. MS (ESI) m/z: 240 [M−H]⁻.

Example 25

6-(4-Fluorophenyl)-2-oxo-N-(4-phenylbutyl)-1,3-benzoxazole-3-carboxamide

The title compound was obtained according to the General Procedure I (Method A), starting from Intermediate 15 (35 mg, 0.150 mmol) and 4-phenylbutyl isocyanate (29 mg, 0.028 mL, 0.165 mmol). White solid (51 mg, 83%). ¹H NMR (400 MHz, CDCl₃) δ 1.65-1.77 (m, 4H), 2.68 (t, J=7.2 Hz, 2H), 3.46 (td, J=6.7, 5.6 Hz, 2H), 7.11-7.21 (m, 5H), 7.26-7.31 (m, 2H), 7.40 (d, J=1.5 Hz, 1H), 7.44 (dd, J=8.3, 1.7 Hz, 1H), 7.50-7.55 (m, 2H), 8.05 (t, J=5.4 Hz, 1H), 8.10 (d, J=8.3 Hz, 1H). ¹³C NMR (101 MHz, CDCl₃) δ 28.72, 29.21, 35.61, 40.32, 108.99, 115.87, 116.05 (d, J=21.7 Hz, 2C), 123.94, 126.04, 127.33, 128.54 (2C), 128.55 (2C), 128.87 (d, J=7.7 Hz, 2C), 136.22, 137.56, 142.02, 142.43, 149.85, 153.35, 160.21 (d, J=285.3 Hz). MS (ESI) m/z: 405 [M−H]⁺.

Example 26

2-Oxo-4-phenyl-N-(4-phenylbutyl)-1,3-benzoxazole-3-carboxamide

The title compound was obtained according to the General Procedure I (Method A), starting from Intermediate 16 (139 mg, 0.658 mmol) and 4-phenylbutyl isocyanate (127 mg, 0.124 mL, 0.724 mmol). In total, four portions of 4-phenylbutyl isocyanate were added with ca. 3 hours in between. Two purifications were necessary to obtain pure title compound. Waxy white solid (18 mg, 7%). ¹H NMR (400 MHz, CDCl₃) δ 1.47-1.58 (m, 2H), 1.59-1.68 (m, 2H), 2.61 (t, J=7.5 Hz, 2H), 3.20 (td, J=6.8, 5.7 Hz, 2H), 7.09 (t, J=5.1 Hz, 1H), 7.15-7.25 (m, 4H), 7.26-7.38 (m, 9H). ¹³C NMR (101 MHz, CDCl₃) δ 28.53, 29.06, 35.63, 40.79, 108.85, 124.89, 125.05, 126.02, 126.45, 127.28, 127.34 (2C), 127.64, 128.41 (2C), 128.51 (2C), 128.54 (3C), 139.40, 142.07, 143.58, 147.90. MS (ESI) m/z: 387 [M−H]⁺.

Example 27

2-Oxo-7-phenyl-N-(4-phenylbutyl)-1,3-benzoxazole-3-carboxamide

The title compound was obtained according to the General Procedure I (Method A), starting from the crude Intermediate 17 and 4-phenylbutyl isocyanate (67 mg, 0.066 mL, 0.385 mmol). Yellow solid (52 mg, 18% over 2 steps, i.e. from Intermediate 9). ¹H NMR (400 MHz, CDCl₃) δ 1.65-1.80 (m, 4H), 2.68 (t, J=7.1 Hz, 2H), 3.47 (q, J=6.6 Hz, 2H), 7.16-7.21 (m, 3H), 7.25-7.32 (m, 2H), 7.33-7.36 (m, 1H), 7.38-7.44 (m, 2H), 7.46-7.52 (m, 2H), 7.69-7.73 (m, 2H), 8.07 (dd, J=7.9, 1.3 Hz, 1H), 8.11 (t, J=5.6 Hz, 1H). ¹³C NMR (101 MHz, CDCl₃) δ 28.71, 29.20, 35.60, 40.30, 114.57, 124.41, 124.49, 125.45, 126.01, 128.52 (4C), 128.54 (3C), 128.68, 128.98 (2C), 134.37, 139.05, 142.04, 149.96, 153.34. MS (ESI) m/z: 387 [M−H]⁺.

Example 28

2-Oxo-N-(4-phenylbutyl)-6-[(E)-styryl]-1,3-benzoxazole-3-carboxamide

The title compound was obtained according to the General Procedure I (Method A), starting from Intermediate 18 (80 mg, 0.337 mmol) and 4-phenylbutyl isocyanate (65 mg, 0.064 mL, 0.371 mmol). White solid (72 mg, 52%). ¹H NMR (400 MHz, CDCl₃) δ 1.64-1.79 (m, 4H), 2.68 (t, J=7.1 Hz, 2H), 3.45 (q, J=6.6 Hz, 2H), 7.09 (br s, 2H), 7.16-7.21 (m, 3H), 7.24-7.31 (m, 3H), 7.35-7.42 (m, 4H), 7.49-7.53 (m, 2H), 8.02 (d, J=8.2 Hz, 1H), 8.02-8.06 (m, 1H). ¹³C NMR (101 MHz, CDCl₃) δ 28.72, 29.21, 35.61, 40.30, 107.18, 115.71, 124.03, 126.04, 126.72 (2C), 127.33, 127.54, 128.13, 128.53 (2C), 128.56 (2C), 128.92 (2C), 129.60, 134.81, 136.94, 142.03, 142.46, 149.85, 153.37. MS (ESI) m/z: 236 [M−CONH(CH₂)₄Ph]⁻.

Example 29

6-[(E)-2-Cyclohexylvinyl]-2-oxo-N-(4-phenylbutyl)-1,3-benzoxazole-3-carboxamide

The title compound was obtained according to the General Procedure I (Method A), starting from Intermediate 19 (58 mg, 0.238 mmol) and 4-phenylbutyl isocyanate (46 mg, 0.045 mL, 0.262 mmol). White solid (81 mg, 82%). ¹H NMR (400 MHz, CDCl₃) δ 1.13-1.39 (m, 5H), 1.63-1.86 (m, 9H), 2.08-2.18 (m, 1H), 2.67 (t, J=7.1 Hz, 2H), 3.44 (q, J=6.4 Hz, 2H), 6.16 (dd, J=15.9, 6.8 Hz, 1H), 6.33 (dd, J=15.9, 1.2 Hz, 1H), 7.15-7.27 (m, 5H), 7.26-7.30 (m, 2H), 7.93 (d, J=8.3 Hz, 1H), 8.04 (t, J=5.6 Hz, 1H). ¹³C NMR (101 MHz, CDCl₃) δ 26.15 (2C), 26.28, 28.72, 29.21, 33.02 (2C), 35.61, 40.26, 41.26, 106.83, 115.45, 123.29, 126.02, 126.35, 126.62, 128.52 (2C), 128.55 (2C), 135.60, 137.87, 142.05, 142.34, 149.94, 153.46. MS (ESI) m/z: 242 [M−CONH(CH₂)₄Ph]⁻.

Example 30

2-Oxo-6-phenethyl-N-(4-phenylbutyl)-1,3-benzoxazole-3-carboxamide

The title compound was obtained according to the General Procedure I (Method A), starting from Intermediate 20 (48 mg, 0.201 mmol) and 4-phenylbutyl isocyanate (46 mg, 0.045 mL, 0.262 mmol). White solid (65 mg, 78%). ¹H NMR (400 MHz, CDCl₃) δ 1.65-1.80 (m, 4H), 2.70 (t, J=7.2 Hz, 2H), 2.91-3.03 (m, 4H), 3.46 (q, J=6.4 Hz, 2H), 7.03 (d, J=1.6 Hz, 1H), 7.07 (dd, J=8.2, 1.6 Hz, 1H), 7.14-7.17 (m, 2H), 7.18-7.24 (m, 4H), 7.27-7.33 (m, 4H), 7.95 (d, J=8.2 Hz, 1H), 8.07 (t, J=5.7 Hz, 1H). ¹³C NMR (101 MHz, CDCl₃) δ 28.72, 29.22, 35.61, 37.86, 38.04, 40.24, 110.02, 115.36, 125.24, 126.03, 126.14, 126.29, 128.53 (2C), 128.56 (4C), 128.62 (2C), 138.91, 141.09, 141.94, 142.06, 150.03, 153.48. MS (ESI) m/z: 415 [M−H]⁺.

Example 31

6-(2-Cyclohexylethyl)-2-oxo-N-(4-phenylbutyl)-1,3-benzoxazole-3-carboxamide

The title compound was obtained according to the General Procedure I (Method A), starting from Intermediate 21

(42 mg, 0.173 mmol) and 4-phenylbutyl isocyanate (40 mg, 0.033 mL, 0.194 mmol). White solid (55 mg, 75%). $^1$H NMR (400 MHz, CDCl$_3$) δ 0.87-0.98 (m, 2H), 1.10-1.29 (m, 4H), 1.45-1.56 (m, 2H), 1.62-1.78 (m, 9H), 2.62-2.69 (m, 4H), 3.44 (q, J=6.6 Hz, 2H), 7.05 (s, 1H), 7.07 (d, J=1.2 Hz, 1H), 7.15-7.20 (m, 3H), 7.26-7.31 (m, 2H), 7.92 (d, J=8.2 Hz, 1H), 8.05 (t, J=5.8 Hz, 1H). $^{13}$C NMR (101 MHz, CDCl$_3$) δ 26.45 (2C), 26.78, 28.72, 29.22, 33.30, 33.42 (2C), 35.61, 37.29, 39.52, 40.22, 109.78, 115.29, 125.02, 125.81, 126.01, 128.52 (2C), 128.55 (2C), 140.53, 142.01, 142.06, 150.06, 153.54. MS (ESI) m/z: 244 [M−CONH(CH$_2$)$_4$Ph]$^-$.

Example 32

6-Butoxy-2-oxo-N-(4-phenylbutyl)-1,3-benzoxazole-3-carboxamide

The title compound was obtained according to the General Procedure I (Method A), starting from Intermediate 31 (49 mg, 0.238 mmol) and 4-phenylbutyl isocyanate (46 mg, 0.045 mL, 0.262 mmol). White solid (67 mg, 74%). $^1$H NMR (400 MHz, CDCl$_3$) δ 0.98 (t, J=7.4 Hz, 3H), 1.44-1.55 (m, 2H), 1.63-1.81 (m, 6H), 2.67 (t, J=7.2 Hz, 2H), 3.44 (q, J=6.4 Hz, 2H), 3.95 (t, J=6.5 Hz, 2H), 6.78 (d, J=2.3 Hz, 1H), 6.79-6.82 (m, 1H), 7.14-7.21 (m, 3H), 7.26-7.31 (m, 2H), 7.91 (d, J=8.7 Hz, 1H), 8.00 (t, J=5.2 Hz, 1H). $^{13}$C NMR (101 MHz, CDCl$_3$) δ 13.96, 19.35, 28.71, 29.23, 31.34, 35.61, 40.22, 68.71, 97.57, 111.14, 115.96, 121.40, 126.01, 128.51 (2C), 128.55 (2C), 142.05, 142.58, 150.03, 153.54, 156.92. MS (ESI) m/z: 383 [M−H]$^+$.

Example 33

6-(2-Cyclohexylethoxy)-2-oxo-N-(4-phenylbutyl)-1,3-benzoxazole-3-carboxamide The title compound was obtained according to the General Procedure I (Method A), starting from Intermediate 32 (50 mg, 0.190 mmol) and 4-phenylbutyl isocyanate (37 mg, 0.036 mL, 0.209 mmol). White solid (45 mg, 55%). $^1$H NMR (400 MHz, CDCl$_3$) δ 0.91-1.04 (m, 2H), 1.10-1.33 (m, 3H), 1.43-1.54 (m, 1H), 1.62-1.80 (m, 11H), 2.67 (t, J=7.2 Hz, 2H), 3.43 (q, J=6.4 Hz, 2H), 3.98 (t, J=6.7 Hz, 2H), 6.77 (d, J=2.3 Hz, 1H), 6.79-6.82 (m, 1H), 7.15-7.20 (m, 3H), 7.26-7.30 (m, 2H), 7.91 (d, J=8.7 Hz, 1H), 8.00 (t, J=5.7 Hz, 1H). $^{13}$C NMR (101 MHz, CDCl$_3$) δ 26.38 (2C), 26.66, 28.71, 29.23, 33.45 (2C), 34.68, 35.61, 36.65, 40.22, 67.02, 97.58, 111.15, 115.96, 121.39, 126.01, 128.51 (2C), 128.55 (2C), 142.06, 142.58, 150.04, 153.55, 156.91. MS (ESI) m/z: 260 [M−CONH(CH$_2$)$_4$Ph]$^-$.

Example 34

2-Oxo-6-phenethyloxy-N-(4-phenylbutyl)-1,3-benzoxazole-3-carboxamide

The title compound was obtained according to the General Procedure I (Method A), starting from Intermediate 33 (65 mg, 0.254 mmol) and 4-phenylbutyl isocyanate (49 mg, 0.048 mL, 0.279 mmol). White solid (71 mg, 65%). $^1$H NMR (400 MHz, CDCl$_3$) δ 1.61-1.77 (m, 4H), 2.67 (t, J=7.2 Hz, 2H), 3.10 (t, J=7.0 Hz, 2H), 3.43 (q, J=6.4 Hz, 2H), 4.17 (t, J=7.0 Hz, 2H), 6.78 (d, J=2.2 Hz, 1H), 6.79-6.82 (m, 1H), 7.15-7.21 (m, 4H), 7.22-7.36 (m, 6H), 7.91 (d, J=8.5 Hz, 1H), 7.99 (t, J=5.6 Hz, 1H). $^{13}$C NMR (101 MHz, CDCl$_3$) δ 28.71, 29.23, 35.61, 35.85, 40.23, 69.69, 97.76, 111.19, 116.01, 121.66, 126.02, 126.79, 128.52 (2C), 128.55 (2C), 128.71 (2C), 129.13 (2C), 130.40, 138.05, 142.06, 142.58, 150.02, 156.57. MS (ESI) m/z: 431 [M−H]$^+$.

Example 35

6-Hydroxy-2-oxo-N-(4-phenylbutyl)-1,3-benzoxazole-3-carboxamide

Intermediate 60 (366 mg, 0.649 mmol) was solubilized in a solution of AcOH/THF/H$_2$O (4:1:1 v/v/v, 15 mL) at room temperature and treated with TBAF (1 M solution in THF, 1.3 mL, 1.3 mmol) for 18 hours. Water (15 mL) and sat. aq. NaHCO$_3$ (10 mL) was added, and the aqueous solution extracted with EtOAc/cyclohexane (3:1, 3×25 mL). The combined organic phases were separated, dried over Na$_2$SO$_4$, and evaporated to dryness. Compound was solubilized in DCM, evaporated on celite, and purified by column chromatography (EtOAc/cyclohexane). White solid (147 mg, 69%). $^1$H NMR (400 MHz, CDCl$_3$) δ 1.64-1.74 (m, 4H), 2.66 (t, J=7.1 Hz, 2H), 3.44 (td, J=6.7, 5.6 Hz, 2H), 5.24 (s, 1H), 6.72 (dd, J=8.7, 2.5 Hz, 1H), 6.79 (d, J=2.4 Hz, 1H), 7.14-7.22 (m, 3H), 7.26-7.31 (m, 2H), 7.88 (d, J=8.7 Hz, 1H), 8.01 (t, J=5.6 Hz, 1H). $^{13}$C NMR (101 MHz, CDCl$_3$) δ 28.69, 29.19, 35.59, 40.26, 98.59, 111.84, 116.13, 121.65, 126.02, 128.52 (2C), 128.54 (2C), 142.02, 142.58, 150.06, 153.32, 153.46. MS (ESI) m/z: 325 [M−H]$^-$.

Example 36

2-Oxo-N-(4-phenylbutyl)-6-propanoyl-1,3-benzoxazole-3-carboxamide

The title compound was obtained according to the General Procedure I (Method A), starting from Intermediate 34 (29 mg, 0.153 mmol) and 4-phenylbutyl isocyanate (29 mg, 0.029 mL, 0.168 mmol). White solid (33 mg, 59%). $^1$H NMR (400 MHz, CDCl$_3$) δ 1.25 (t, J=7.2 Hz, 3H), 1.64-1.79 (m, 4H), 2.68 (t, J=7.1 Hz, 2H), 3.01 (q, J=7.2 Hz, 2H), 3.46 (q, J=6.4 Hz, 2H), 7.15-7.21 (m, 3H), 7.26-7.31 (m, 2H), 7.86 (d, J=1.4 Hz, 1H), 7.92 (dd, J=8.4, 1.5 Hz, 1H), 8.02 (t, J=5.1 Hz, 1H), 8.14 (d, J=8.4 Hz, 1H). $^{13}$C NMR (101 MHz, CDCl$_3$) δ 8.36, 28.68, 29.13, 31.97, 35.58, 40.40, 109.54, 115.34, 125.81, 126.06, 128.54 (4C), 131.75, 133.92, 141.95, 142.04, 149.50, 153.16, 198.89. MS (ESI) m/z: 367 [M−H]$^+$.

Example 37

6-Benzoyl-2-oxo-N-(4-phenylbutyl)-1,3-benzoxazole-3-carboxamide

The title compound was obtained according to the General Procedure I (Method A), starting from Intermediate 35 (100 mg, 0.418 mmol) and 4-phenylbutyl isocyanate (81 mg, 0.079 mL, 0.46 mmol). White solid (142 mg, 82%). $^1$H NMR (400 MHz, CDCl$_3$) δ 1.61-1.79 (m, 4H), 2.68 (t, J=6.6 Hz, 2H), 3.47 (q, J=6.3 Hz, 2H), 7.15-7.21 (m, 3H), 7.26-7.32 (m, 2H), 7.46-7.54 (m, 2H), 7.58-7.65 (m, 1H), 7.69-7.80 (m, 4H), 8.03 (t, J=5.3 Hz, 1H), 8.16 (d, J=8.6 Hz, 1H). $^{13}$C NMR (101 MHz, CDCl$_3$) δ 28.67, 29.15, 35.59, 40.43, 111.59, 115.16, 126.07, 128.12, 128.55 (4C), 128.61 (2C), 130.03 (2C), 131.58, 132.79, 134.36, 137.42, 141.79, 141.96, 149.51, 153.16, 194.90. MS (ESI) m/z: 238 [M−CONH(CH$_2$)$_4$Ph]$^-$.

Example 38

6-(4-Chlorobenzoyl)-2-oxo-N-(4-phenylbutyl)-1,3-benzoxazole-3-carboxamide

The title compound was obtained according to the General Procedure I (Method A), starting from Intermediate 36 (169 mg, 0.616 mmol) and 4-phenylbutyl isocyanate (119 mg, 0.116 mL, 0.678 mmol). White solid (66 mg, 26%). $^1$H NMR (400 MHz, CDCl$_3$) δ 1.65-1.79 (m, 4H), 2.68 (t, J=7.0 Hz, 2H), 3.47 (q, J=6.3 Hz, 2H), 7.16-7.22 (m, 3H), 7.26-7.31 (m, 2H), 7.47-7.51 (m, 2H), 7.69-7.75 (m, 4H), 8.02 (t, J=5.4 Hz, 1H), 8.17 (d, J=8.2 Hz, 1H). $^{13}$C NMR (101 MHz, CDCl$_3$) δ 28.68, 29.13, 35.58, 40.43, 111.48, 115.24, 126.07, 128.01, 128.54 (4C), 128.99 (2C), 131.43 (2C), 131.74, 133.93, 135.63, 139.36, 141.82, 141.94, 149.44, 153.06, 193.70. MS (ESI) m/z: 272 [M−CONH(CH$_2$)$_4$Ph]$^-$.

Example 39

N-(4-Cyclohexylbutyl)-2-oxo-1,3-benzoxazole-3-carboxamide

The title compound was obtained according to the General Procedure I (Method B), starting from 3H-1,3-benzoxazol-2-one (70 mg, 0.52 mmol) and Intermediate 37 (150 mg, 0.78 mmol). White powder (68 mg, 41%). $^1$H NMR (400 MHz, CDCl$_3$) δ 0.76-0.98 (m, 2H), 1.03-1.28 (m, 6H), 1.31-1.49 (m, 2H), 1.55-1.79 (m, 7H), 3.42 (td, J=7.1, 5.6 Hz, 2H), 7.21-7.24 (m, 2H), 7.24-7.29 (m, 1H), 7.98-8.13 (m, 2H). $^{13}$C NMR (101 MHz, CDCl$_3$) δ 24.23, 26.52, 26.83, 29.86, 33.48, 37.17, 37.66, 40.45, 109.98, 115.74, 124.58, 125.08, 128.19, 141.87, 149.92, 153.32. MS (ESI) m/z: 317 [M−H]$^+$, 334 [M−NH$_4$]$^+$.

Example 40

2-Oxo-N-[(4-propylcyclohexyl)methyl]-1,3-benzoxazole-3-carboxamide

The title compound was obtained according to the General Procedure I (Method C), starting from 3H-1,3-benzoxazol-2-one (30 mg, 0.22 mmol) and Intermediate 39 (64 mg, 0.33 mmol). White powder (40 mg, 57%). $^1$H NMR (400 MHz, CDCl$_3$) δ 0.90 (t, J=7.3 Hz, 3H), 0.93-1.11 (m, 4H), 1.16-1.25 (m, 3H), 1.27-1.40 (m, 2H), 1.51-1.65 (m, 1H), 1.76-1.91 (m, 4H), 3.26-3.35 (m, 2H), 7.22-7.32 (m, 3H), 8.06-8.11 (m, 1H), 8.11-8.19 (m, 1H). $^{13}$C NMR (101 MHz, CDCl$_3$) δ 14.50, 20.12, 30.84, 32.72, 37.42, 38.18, 39.71, 46.61, 109.99, 115.77, 124.59, 125.14, 128.21, 141.88, 150.04, 153.37. MS (ESI) m/z: 317 [M−H]$^+$, 334 [M−NH$_4$]$^+$.

Example 41

2-Oxo-N-[(4-propylphenyl)methyl]-1,3-benzoxazole-3-carboxamide

The title compound was obtained according to the General Procedure I (Method B), starting from 3H-1,3-benzoxazol-2-one (60 mg, 0.45 mmol) and Intermediate 41 (125 mg, 0.67 mmol). White powder (40 mg, 29%). $^1$H NMR (400 MHz, CDCl$_3$) δ 0.94 (t, J=7.3 Hz, 3H), 1.58-1.71 (m, 2H), 2.58 (dd, J=8.4, 6.8 Hz, 2H), 4.58 (d, J=5.7 Hz, 2H), 7.17 (d, J=8.1 Hz, 2H), 7.21-7.32 (m, 5H), 8.07-8.14 (m, 1H), 8.35-8.46 (m, 1H). $^{13}$C NMR (101 MHz, DMSO) δ 13.94, 24.66, 37.84, 44.09, 110.03, 115.78, 124.70, 125.13, 128.11, 129.05, 134.60, 141.90, 142.49, 149.96, 153.23. MS (ESI) m/z: 311 [M−H]$^+$, 328 [M−NH$_4$]$^+$.

Example 42

N-Octyl-2-oxo-1,3-benzoxazole-3-carboxamide

The title compound was obtained according to the General Procedure I (Method A), starting from 3H-1,3-benzoxazol-2-one (70 mg, 0.52 mmol) and octyl isocyanate (0.137 mL, 0.77 mmol). White powder (118 mg, 78%). $^1$H NMR (400 MHz, CDCl$_3$) δ 0.83-0.94 (m, 3H), 1.20-1.45 (m, 10H), 1.63 (m, 2H), 3.37-3.46 (m, 2H), 7.26 (s, 3H), 8.00-8.13 (m, 2H). $^{13}$C NMR (101 MHz, CDCl$_3$) δ 14.20, 22.76, 26.97, 29.30, 29.33, 29.56, 40.45, 109.97, 115.74, 124.57, 125.07, 128.18, 141.87, 149.92, 154.07. MS (ESI) m/z: 291 [M−H]$^+$, 308 [M−NH$_4$]$^+$.

Example 43

2-Oxo-N-(3-phenylpropyl)-1,3-benzoxazole-3-carboxamide

The title compound was obtained according to the General Procedure I (Method B), starting from 3H-1,3-benzoxazol-2-one (70 mg, 0.52 mmol) and 3-phenylpropan-1-amine (106 mg, 0.111 mL, 0.78 mmol). White solid (65 mg, 42%). $^1$H NMR (400 MHz, CDCl$_3$) δ 1.99 (p, J=7.4 Hz, 2H), 2.73 (t, J=7.6 Hz, 2H), 3.46 (q, J=6.6 Hz, 2H), 7.16-7.32 (m, 8H), 8.07 (d, J=7.5 Hz, 1H), 8.07-8.14 (m, 1H). $^{13}$C NMR (101 MHz, CDCl$_3$) δ 31.05, 33.19, 39.87, 110.04, 115.75, 124.67, 125.13, 126.22, 128.14, 128.52 (2C), 128.65 (2C), 141.13, 141.89, 149.98, 153.33. MS (ESI) m/z: 297 [M−H]$^+$.

Example 44

2-Oxo-N-[4-(2-thienyl)butyl]-1,3-benzoxazole-3-carboxamide

The title compound was obtained according to the General Procedure I (Method C), starting from 3H-1,3-benzoxazol-2-one (70 mg, 0.52 mmol) and Intermediate 43 (150 mg, 0.78 mmol). White solid (83 mg, 51%). $^1$H NMR (400 MHz, CDCl$_3$) δ 1.67-1.84 (m, 4H), 2.89 (t, J=7.2 Hz, 2H), 3.46 (q, J=6.7 Hz, 2H), 6.80 (d, J=3.3 Hz, 1H), 6.91 (dd, J=5.1, 3.4 Hz, 1H), 7.11 (dd, J=5.1, 1.2 Hz, 1H), 7.22-7.29 (m, 3H), 8.04-8.10 (m, 2H). $^{13}$C NMR (101 MHz, CDCl$_3$) δ 29.01, 29.06, 29.60, 40.13, 110.04, 115.75, 123.23, 124.46, 124.66, 125.13, 126.90, 128.14, 141.89, 144.79, 149.99, 153.33. MS (ESI) m/z: 317 [M−H]$^+$.

Example 45

N-[4-(4-Methoxyphenyl)butyl]-2-oxo-1,3-benzoxazole-3-carboxamide

The title compound was obtained according to the General Procedure I (Method C), starting from 3H-1,3-benzoxazol-2-one (70 mg, 0.52 mmol) and Intermediate 45 (168 mg, 0.78 mmol). White solid (42 mg, 24%). $^1$H NMR (400 MHz, CDCl$_3$) δ 1.61-1.75 (m, 4H), 2.61 (t, J=6.9 Hz, 2H), 3.44 (q, J=6.5 Hz, 2H), 3.78 (s, 3H), 6.79-6.85 (m, 2H), 7.07-7.12 (m, 2H), 7.21-7.33 (m, 3H), 8.03-8.09 (m, 2H). $^{13}$C NMR (101 MHz, CDCl$_3$) δ 28.93, 29.11, 34.66, 40.27, 55.40, 110.02, 113.95 (2C), 115.75, 124.64, 125.11, 128.16, 129.44 (2C), 134.12, 141.88, 149.96, 153.32, 157.96. MS (ESI) m/z: 341 [M−H]$^+$.

Example 46

N-[4-(4-Fluorophenyl)butyl]-2-oxo-1,3-benzoxazole-3-carboxamide

The title compound was obtained according to the General Procedure I (Method C), starting from 3H-1,3-benzoxazol-2-one (70 mg, 0.52 mmol) and Intermediate 47 (160 mg, 0.78 mmol). White solid (80 mg, 47%). $^1$H NMR (400 MHz, CDCl$_3$) δ 1.64-1.80 (m, 4H), 2.67 (t, J=7.0 Hz, 2H), 3.39-3.57 (m, 2H), 6.92-7.05 (m, 2H), 7.11-7.21 (m, 2H), 7.23-7.27 (m, 2H), 7.27-7.32 (m, 1H), 7.83-8.38 (m, 2H). $^{13}$C NMR (101 MHz, CDCl$_3$) δ 28.81, 29.10, 34.76, 40.18, 110.03, 115.23 (d, J=21.4 Hz, 2C), 115.73, 124.66, 125.13, 128.12, 129.82 (d, J=7.9 Hz, 2C), 137.62, 141.87, 149.97, 153.32, 161.43 (d, J=242.8 Hz, 1C). MS (ESI) m/z: 329 [M–H]$^+$, 346 [M–NH$_4$]$^+$, 351 [M–Na]$^+$.

Example 47

2-Oxo-N-[4-(p-tolyl)butyl]-1,3-benzoxazole-3-carboxamide

The title compound was obtained according to the General Procedure I (Method C), starting from 3H-1,3-benzoxazol-2-one (50 mg, 0.37 mmol) and Intermediate 49 (110 mg, 0.55 mmol). White solid (47 mg, 39%). $^1$H NMR (400 MHz, CDCl$_3$) δ 1.63-1.83 (m, 4H), 2.31 (s, 3H), 2.63 (t, J=7.1 Hz, 2H), 3.44 (td, J=6.7, 5.5 Hz, 2H), 7.04-7.15 (m, 4H), 7.22-7.29 (m, 3H), 8.01-8.13 (m, 2H). $^{13}$C NMR (101 MHz, CDCl$_3$) δ 21.12, 28.80, 29.16, 35.13, 40.28, 110.02, 115.76, 124.63, 125.12, 128.16, 128.42, 129.19, 135.46, 138.94, 141.89, 149.96, 153.32. MS (ESI) m/z: 323 [M–H]$^-$.

Example 48

N-[4-(4-Nitrophenyl)butyl]-2-oxo-1,3-benzoxazole-3-carboxamide

The title compound was obtained according to the General Procedure I (Method C), starting from 3H-1,3-benzoxazol-2-one (70 mg, 0.52 mmol) and Intermediate 51 (180 mg, 0.78 mmol). White solid (29 mg, 16%). $^1$H NMR (400 MHz, CDCl$_3$) δ 1.64-1.82 (m, 4H), 2.78 (t, J=7.4 Hz, 2H), 3.47 (q, J=6.7 Hz, 2H), 7.21-7.32 (m, 3H), 7.32-7.36 (m, 2H), 8.03-8.07 (m, 1H), 8.101 (t, J=5.0 Hz, 1H), 8.15-8.17 (m, 2H). $^{13}$C NMR (101 MHz, CDCl$_3$) δ 28.23, 29.19, 35.49, 40.00, 110.10, 115.71, 123.86 (2C), 124.77, 125.19, 128.06, 129.34 (2C), 141.88, 146.62, 149.85, 150.04, 153.35. MS (ESI) m/z: 356 [M–H]$^+$.

Example 49

2-Oxo-N-[3-(3-pyridyl)propyl]-1,3-benzoxazole-3-carboxamide

The title compound was obtained according to the General Procedure I (Method C), starting from 3H-1,3-benzoxazol-2-one (70 mg, 0.52 mmol) and Intermediate 53 (162 mg, 0.78 mmol). Intermediate 53 was here solubilized in 3 eq. Et$_3$N (i.e. 0.218 mL) and DCM (5 mL) before adding it to reaction. Yellowish waxy solid (53 mg, 34%). $^1$H NMR (400 MHz, CDCl$_3$) δ 2.00 (p, J=7.2 Hz, 2H), 2.74 (t, J=8.1, 7.6 Hz, 2H), 3.48 (q, J=6.6 Hz, 2H), 7.20-7.31 (m, 4H), 7.56 (dt, J=7.9, 1.9 Hz, 1H), 8.04-8.09 (m, 1H), 8.15 (t, J=6.1 Hz, 1H), 8.46 (dd, J=4.9, 1.5 Hz, 1H), 8.49 (d, J=1.7 Hz, 1H). $^{13}$C NMR (101 MHz, CDCl$_3$) δ 0.36, 30.88, 39.73, 110.08, 115.72, 123.63, 124.76, 125.18, 128.04, 136.14, 136.55, 141.88, 147.61, 149.78, 150.04, 153.34. MS (ESI) m/z: 298 [M–H]$^+$.

Example 50

N-[3-(3-Fluorophenyl)propyl]-2-oxo-1,3-benzoxazole-3-carboxamide

The title compound was obtained according to the General Procedure I (Method C), starting from 3H-1,3-benzoxazol-2-one (82 mg, 0.61 mmol) and Intermediate 55 (173 mg, 0.913 mmol). White solid (43 mg, 27%). $^1$H NMR (400 MHz, CDCl$_3$) δ 1.99 (p, J=7.3 Hz, 2H), 2.73 (t, J=7.7 Hz, 2H), 3.46 (q, J=6.7 Hz, 2H), 6.84-6.95 (m, 2H), 6.95-7.01 (m, 1H), 7.20-7.34 (m, 4H), 8.07 (d, J=7.4 Hz, 1H), 8.12 (s, 1H). $^{13}$C NMR (101 MHz, CDCl$_3$) δ 30.84, 32.93 (d, J=1.4 Hz), 39.77, 110.06, 113.15 (d, J=21.1 Hz), 115.35 (d, J=21.1 Hz), 115.74, 124.16 (d, J=3.0 Hz), 124.71, 125.16, 128.09, 130.06 (d, J=8.7 Hz), 141.89, 143.69 (d, J=7.0 Hz), 150.00, 153.34, 163.12 (d, J=245.5 Hz). MS (ESI) m/z: 315 [M–H]$^+$.

Example 51

N-[3-(2-Chlorophenyl)propyl]-2-oxo-1,3-benzoxazole-3-carboxamide

The title compound was obtained according to the General Procedure I (Method C), starting from 3H-1,3-benzoxazol-2-one (50 mg, 0.37 mmol) and Intermediate 57 (110 mg, 0.55 mmol). The crude product was purified by preparative HPLC. White solid (29 mg, 24%). $^1$H NMR (400 MHz, CDCl$_3$) δ 2.00 (tt, J=7.5, 6.5 Hz, 2H), 2.76-2.94 (m, 2H), 3.48 (td, J=7.0, 5.7 Hz, 2H), 7.11-7.22 (m, 2H), 7.22-7.26 (m, 2H), 7.26-7.29 (m, 1H), 7.35 (dd, J=7.7, 1.6 Hz, 1H), 8.02-8.11 (m, 1H), 8.11-8.22 (m, 1H). $^{13}$C NMR (101 MHz, CDCl$_3$) δ 29.53, 30.98, 39.88, 110.04, 115.74, 124.67, 125.13, 127.05, 127.77, 128.13, 129.76, 130.54, 134.09, 138.80, 141.90, 150.00, 153.31. MS (ESI) m/z: 331 [M–H]$^+$, 353 [M–Na]$^+$.

Example 52

N-[4-(2-Naphthyl)butyl]-2-oxo-1,3-benzoxazole-3-carboxamide

The title compound was obtained according to the General Procedure I (Method C), starting from 3H-1,3-benzoxazol-2-one (26 mg, 0.19 mmol) and Intermediate 59 (68 mg, 0.30 mmol). White solid (36 mg, 52%). $^1$H NMR (400 MHz, CDCl$_3$) δ 1.66-1.79 (m, 2H), 1.78-1.91 (m, 2H), 2.84 (t, J=7.4 Hz, 2H), 3.47 (td, J=7.0, 5.7 Hz, 2H), 7.21-7.30 (m, 3H), 7.34 (dd, J=8.4, 1.7 Hz, 1H), 7.38-7.49 (m, 2H), 7.60-7.66 (m, 1H), 7.74-7.84 (m, 3H), 8.01-8.12 (m, 2H). $^{13}$C NMR (101 MHz, CDCl$_3$) δ 28.54, 29.19, 35.71, 40.25, 110.01, 115.75, 124.63, 125.11, 125.29, 126.05, 126.59, 127.35, 127.55, 127.73, 128.09, 128.14, 132.17, 133.74, 139.51, 141.88, 149.98, 153.31. MS (ESI) m/z: non-ionizable compound under routine conditions used.

Example 53

N-hexyl-2-oxo-1,3-benzoxazole-3-carbothioamide

The title compound was obtained according to the General Procedure I (Method A), starting from 3H-1,3-benzoxazol-2-one (100 mg, 0.74 mmol) and hexyl isothiocyanate (117 mg, 0.126 mL, 0.814 mmol). After 2 hours, a second portion hexyl isothiocyanate was added, and the reaction was stirred for another 15 hours. Clear colorless solid (2.6 mg, 1.3%). $^1$H NMR (400 MHz, CDCl$_3$) δ 0.87-0.93 (m, 3H), 1.28-1.48 (m, 6H), 1.75 (p, J=7.4 Hz, 2H), 3.74 (td, J=7.2, 5.1 Hz, 2H), 7.24-7.29 (m, 3H), 8.93-8.98 (m, 1H), 10.16 (br s, 1H). $^{13}$C NMR (101 MHz, CDCl$_3$) δ 14.12, 22.65, 26.80, 27.89, 31.52, 45.74, 109.99, 117.97, 124.51, 125.12, 129.22, 141.93, 153.00, 176.32. MS (ESI) m/z: 279 [M−H]⁺.

Example 54

2-Oxo-N-(4-phenylbutyl)-1,3-benzoxazole-3-carbothioamide

The title compound was obtained according to the General Procedure I (Method A), starting from 3H-1,3-benzoxazol-2-one (100 mg, 0.740 mmol) and 4-phenylbutyl isothiocyanate (156 mg, 0.155 mL, 0.814 mmol). After 2 hours, a second portion 4-phenylbutyl isothiocyanate was added, and the reaction was stirred for another 15 hours. White solid (11.3 mg, 5%). $^1$H NMR (400 MHz, CDCl$_3$) δ 1.75-1.82 (m, 4H), 2.70 (t, J=7.0 Hz, 2H), 3.74-3.81 (m, 2H), 7.16-7.21 (m, 3H), 7.23-7.31 (m, 5H), 8.92-8.99 (m, 1H), 10.17 (br s, 1H). $^{13}$C NMR (101 MHz, CDCl$_3$) δ 27.52, 28.79, 35.54, 45.45, 110.00, 117.96, 124.53, 125.15, 126.06, 128.54 (4C), 129.18, 141.86, 141.91, 152.98, 176.39. MS (ESI) m/z: 327 [M−H]⁺.

Example 55

N-Methyl-2-oxo-N-(4-phenylbutyl)-1,3-benzoxazole-3-carboxamide

The title compound was obtained according to the General Procedure I (Method C), starting from 3H-1,3-benzoxazol-2-one (50 mg, 0.37 mmol) and N-methyl-4-phenylbutan-1-amine (90 mg, 0.55 mmol). Colorless oil (77 mg, 64%). $^1$H NMR (400 MHz, CDCl$_3$) δ 1.60-1.84 (m, 4H), 2.47-2.78 (m, 2H), 3.09 (s, 3H), 3.34-3.74 (m, 2H), 7.12-7.24 (m, 5H), 7.27 (d, J=5.3 Hz, 4H). $^{13}$C NMR (101 MHz, CDCl$_3$) δ 28.19, 35.48, 36.61, 49.67, 110.20, 112.79, 124.03, 124.44, 125.98, 128.47, 129.20, 142.04, 143.10, 149.95, 150.59. MS (ESI) m/z: 325 [M−H]⁺, 342 [M−NH$_4$]⁺.

Example 56

4-Fluoro-2-oxo-N-(4-phenylbutyl)-1,3-benzoxazole-3-carboxamide

The title compound was obtained according to the General Procedure I (Method A), starting from Intermediate 61 (61.2 mg, 0.400 mmol) and 4-phenylbutyl isocyanate (149 mg, 0.070 mL, 0.440 mmol). White solid (49 mg, 37%). $^1$H NMR (400 MHz, CDCl$_3$) δ 1.65-1.81 (m, 4H), 2.69 (t, J=7.2 Hz, 2H), 3.44-3.54 (m, 2H), 7.06-7.13 (m, 2H), 7.18-7.27 (m, 4H), 7.27-7.34 (m, 2H), 7.83-7.89 (m, 1H). $^{13}$C NMR (101 MHz, CDCl$_3$) δ 28.55, 28.94, 35.44, 40.71, 106.20 (d, J=4.4 Hz), 113.98 (d, J=22.2 Hz), 115.19 (d, J=13.9 Hz), 125.52 (d, J=7.8 Hz), 125.87, 128.38, 128.41, 141.90, 143.74 (d, J=5.1 Hz), 147.69, 148.04 (d, J=257.5 Hz), 152.62. MS (ESI) m/z: 329 [M−H]⁺.

Example 57

2-Oxo-N-(5-phenylpentyl)-1,3-benzoxazole-3-carboxamide

The title compound was obtained according to the General Procedure I (Method C), starting from 3H-1,3-benzoxazol-2-one (68 mg, 0.50 mmol) and Intermediate 63 (100 mg, 0.50 mmol). White solid (83 mg, 51%). $^1$H NMR (400 MHz, CDCl$_3$) δ 1.42-1.51 (m, 2H), 1.65-1.76 (m, 4H), 2.66 (t, J=7.6 Hz, 2H), 3.45 (td, J=7.1, 5.9 Hz, 2H), 7.16-7.22 (m, 3H), 7.24-7.32 (m, 5H), 8.06-8.13 (m, 2H). $^{13}$C NMR (101 MHz, CDCl$_3$) δ 26.42, 29.30, 31.00, 35.75, 40.20, 109.86, 115.61, 124.48, 124.97, 125.71, 128.03, 128.29, 128.38, 141.74, 142.32, 149.80, 153.18. MS (ESI) m/z: 325 [M−H]⁺.

Example 58

2-Oxo-N-(6-phenylhexyl)-1,3-benzoxazole-3-carboxamide

The title compound was obtained according to the General Procedure I (Method C), starting from 3H-1,3-benzoxazol-2-one (40 mg, 0.30 mmol) and Intermediate 64 (95 mg, 0.44 mmol). White solid (32 mg, 31%). $^1$H NMR (400 MHz, CDCl$_3$) δ 1.32-1.52 (m, 4H), 1.59-1.71 (m, 4H), 2.51-2.74 (m, 2H), 3.31-3.51 (m, 2H), 7.13-7.20 (m, 3H), 7.21-7.31 (m, 5H), 8.02-8.11 (m, 2H). $^{13}$C NMR (101 MHz, CDCl$_3$) δ 26.85, 29.00, 29.51, 31.42, 35.98, 40.40, 110.00, 115.76, 124.61, 125.10, 125.77, 128.18, 128.39, 128.52, 141.89, 142.72, 149.94, 153.33. MS (ESI) m/z: 339 [M−H]⁺, 356 [M−NH$_4$]⁺.

Example 59

N-Heptyl-2-oxo-1,3-benzoxazole-3-carboxamide

The title compound was obtained according to the General Procedure I (Method A), starting from 3H-1,3-benzoxazol-2-one (50 mg, 0.37 mmol) and heptyl isocyanate (58 mg, 0.066 mL, 0.41 mmol). White solid (71 mg, 69%). $^1$H NMR (400 MHz, CDCl$_3$) δ 0.88 (t, J=7.0 Hz, 3H), 1.22-1.44 (m, 8H), 1.55-1.73 (m, 2H), 3.42 (td, J=7.0, 6.0 Hz, 2H), 7.12-7.42 (m, 3H), 7.81-8.38 (m, 2H). $^{13}$C NMR (101 MHz, CDCl$_3$) δ 14.21, 22.72, 26.93, 29.04, 29.57, 31.84, 40.44, 110.00, 115.74, 124.60, 125.10, 128.16, 141.85, 149.94, 153.32. MS (ESI) m/z: 277 [M−H]⁺, 294 [M−NH$_4$]⁺.

Exemplary compounds according to the present invention are reported in the following Table 1.

TABLE 1

| | Exemplified compounds of the invention | | | |
|---|---|---|---|---|
| Example | Structure | Formula | MW | Name |
| 1 | 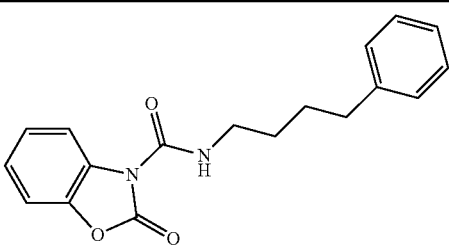 | C$_{18}$H$_{18}$N$_2$O$_3$ | 310.4 | 2-oxo-N-(4-phenylbutyl)-1,3-benzoxazole-3-carboxamide |

TABLE 1-continued

Exemplified compounds of the invention

| Example | Structure | Formula | MW | Name |
|---|---|---|---|---|
| 2 | 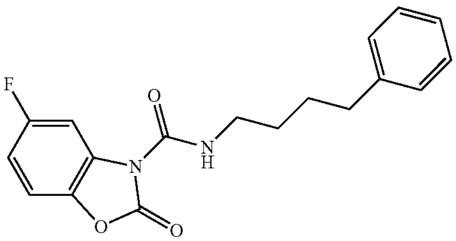 [SMILES: O=C(NCCCCc1ccccc1)n1c(=O)oc2ccc(F)cc21] | $C_{18}H_{17}FN_2O_3$ | 328.3 | 5-fluoro-2-oxo-N-(4-phenylbutyl)-1,3-benzoxazole-3-carboxamide |
| 3 | 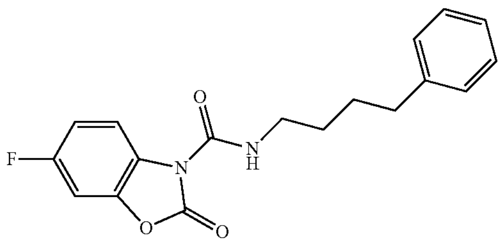 [SMILES: O=C(NCCCCc1ccccc1)n1c(=O)oc2cc(F)ccc21] | $C_{18}H_{17}FN_2O_3$ | 328.3 | 6-fluoro-2-oxo-N-(4-phenylbutyl)-1,3-benzoxazole-3-carboxamide |
| 4 | 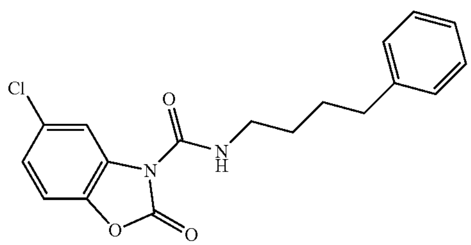 [SMILES: O=C(NCCCCc1ccccc1)n1c(=O)oc2ccc(Cl)cc21] | $C_{18}H_{17}ClN_2O_3$ | 344.8 | 5-chloro-2-oxo-N-(4-phenylbutyl)-1,3-benzoxazole-3-carboxamide |
| 5 | 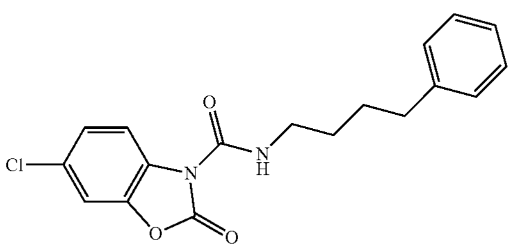 [SMILES: O=C(NCCCCc1ccccc1)n1c(=O)oc2cc(Cl)ccc21] | $C_{18}H_{17}ClN_2O_3$ | 344.8 | 6-chloro-2-oxo-N-(4-phenylbutyl)-1,3-benzoxazole-3-carboxamide |
| 6 | 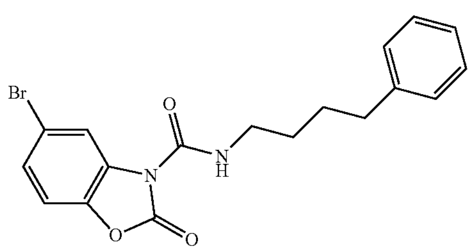 | $C_{18}H_{17}BrN_2O_3$ | 389.2 | 5-bromo-2-oxo-N-(4-phenylbutyl)-1,3-benzoxazole-3-carboxamide |
| 7 | 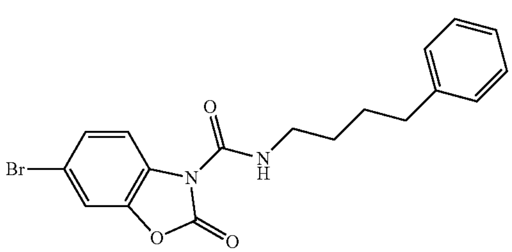 [SMILES: O=C(NCCCCc1ccccc1)n1c(=O)oc2cc(Br)ccc21] | $C_{18}H_{17}BrN_2O_3$ | 389.2 | 6-bromo-2-oxo-N-(4-phenylbutyl)-1,3-benzoxazole-3-carboxamide |

TABLE 1-continued

Exemplified compounds of the invention

| Example | Structure | Formula | MW | Name |
|---|---|---|---|---|
| 8 | 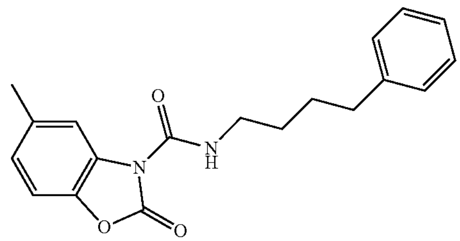 [SMILES: Cc1ccc2oc(=O)n(C(=O)NCCCCc3ccccc3)c2c1] | $C_{19}H_{20}N_2O_3$ | 324.4 | 5-methyl-2-oxo-N-(4-phenylbutyl)-1,3-benzoxazole-3-carboxamide |
| 9 | 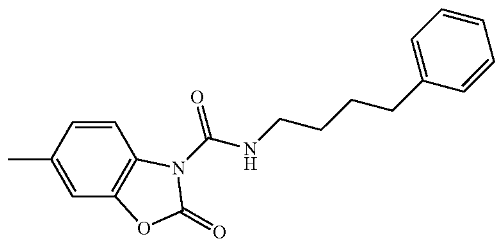 [SMILES: Cc1ccc2c(c1)oc(=O)n2C(=O)NCCCCc1ccccc1] | $C_{19}H_{20}N_2O_3$ | 324.4 | 6-methyl-2-oxo-N-(4-phenylbutyl)-1,3-benzoxazole-3-carboxamide |
| 10 | 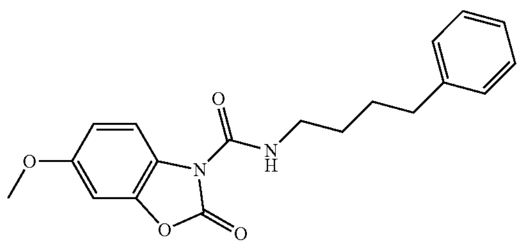 [SMILES: COc1ccc2c(c1)oc(=O)n2C(=O)NCCCCc1ccccc1] | $C_{19}H_{20}N_2O_4$ | 340.4 | 6-methoxy-2-oxo-N-(4-phenyl-butyl)-1,3-benzoxazole-3-carboxamide |
| 11 | 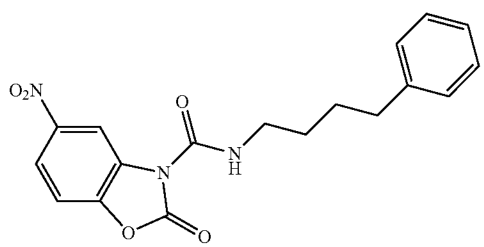 [SMILES: O=C(NCCCCc1ccccc1)n1c(=O)oc2ccc([N+](=O)[O-])cc21] | $C_{18}H_{17}N_3O_5$ | 355.3 | 5-nitro-2-oxo-N-(4-phenylbutyl)-1,3-benzoxazole-3-carboxamide |
| 12 | 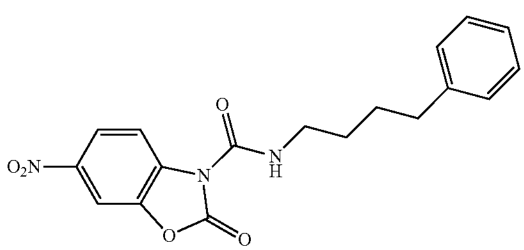 [SMILES: O=C(NCCCCc1ccccc1)n1c(=O)oc2cc([N+](=O)[O-])ccc21] | $C_{18}H_{17}N_3O_5$ | 355.3 | 6-nitro-2-oxo-N-(4-phenylbutyl)-1,3-benzoxazole-3-carboxamide |
| 13 | 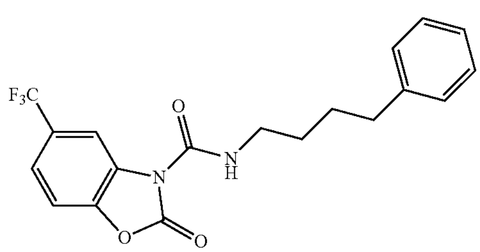 [SMILES: O=C(NCCCCc1ccccc1)n1c(=O)oc2ccc(C(F)(F)F)cc21] | $C_{19}H_{17}F_3N_2O_3$ | 378.3 | 2-oxo-N-(4-phenylbutyl)-5-(trifluoromethyl)-1,3-benzoxazole-3-carboxamide |

TABLE 1-continued

Exemplified compounds of the invention

| Example | Structure | Formula | MW | Name |
|---|---|---|---|---|
| 14 | 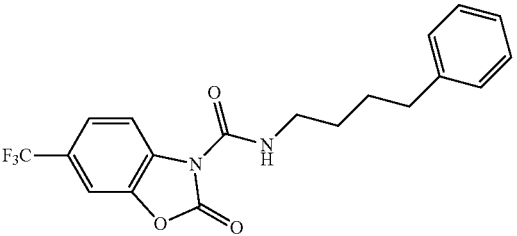 | $C_{19}H_{17}F_3N_2O_3$ | 378.3 | 2-oxo-N-(4-phenylbutyl)-6-(trifluoromethyl)-1,3-benzoxazole-3-carboxamide |
| 15 | 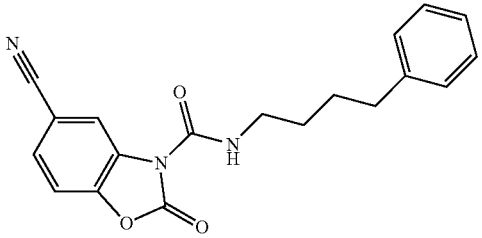 [SMILES: N#Cc1ccc2oc(=O)n(C(=O)NCCCCc3ccccc3)c2c1] | $C_{19}H_{17}N_3O_3$ | 335.4 | 5-cyano-2-oxo-N-(4-phenylbutyl)-1,3-benzoxazole-3-carboxamide |
| 16 | 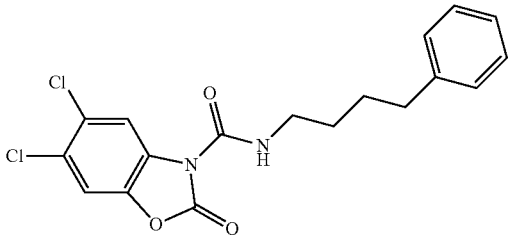 [SMILES: O=C(NCCCCc1ccccc1)n1c(=O)oc2cc(Cl)c(Cl)cc21] | $C_{18}H_{16}Cl_2N_2O_3$ | 379.2 | 5,6-dichloro-2-oxo-N-(4-phenylbutyl)-1,3-benzoxazole-3-carboxamide |
| 17 | 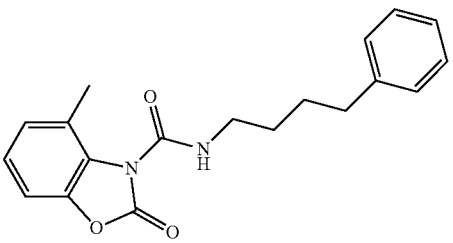 [SMILES: Cc1cccc2oc(=O)n(C(=O)NCCCCc3ccccc3)c12] | $C_{19}H_{20}N_2O_3$ | 324.4 | 4-methyl-2-oxo-N-(4-phenylbutyl)-1,3-benzoxazole-3-carboxamide |
| 18 | 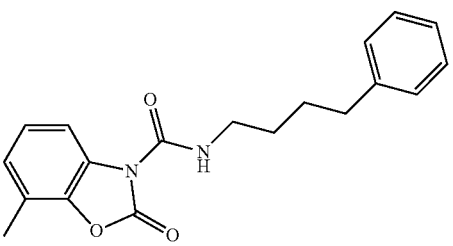 [SMILES: Cc1cccc2c1oc(=O)n2C(=O)NCCCCc1ccccc1] | $C_{19}H_{20}N_2O_3$ | 324.4 | 7-methyl-2-oxo-N-(4-phenylbutyl)-1,3-benzoxazole-3-carboxamide |
| 19 | 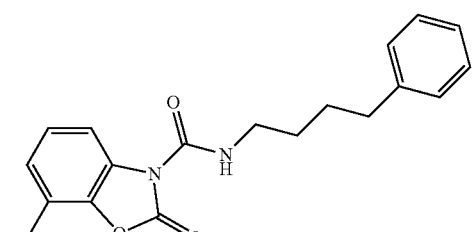 | $C_{18}H_{17}BrN_2O_3$ | 389.2 | 7-bromo-2-oxo-N-(4-phenylbutyl)-1,3-benzoxazole-3-carboxamide |

TABLE 1-continued

Exemplified compounds of the invention

| Example | Structure | Formula | MW | Name |
|---------|-----------|---------|------|------|
| 20 | 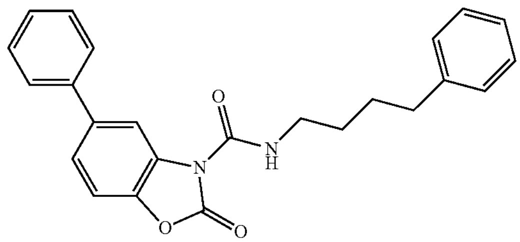 [SMILES: O=C(NCCCCc1ccccc1)n1c(=O)oc2ccc(-c3ccccc3)cc21] | $C_{24}H_{22}N_2O_3$ | 386.4 | 2-oxo-5-phenyl-N-(4-phenylbutyl)-1,3-benzoxazole-3-carboxamide |
| 21 | 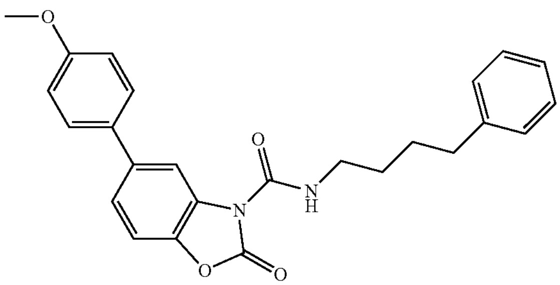 [SMILES: COc1ccc(-c2ccc3oc(=O)n(C(=O)NCCCCc4ccccc4)c3c2)cc1] | $C_{25}H_{24}N_2O_4$ | 416.5 | 5-(4-methoxyphenyl)-2-oxo-N-(4-phenylbutyl)-1,3-benzoxazole-3-carboxamide |
| 22 | 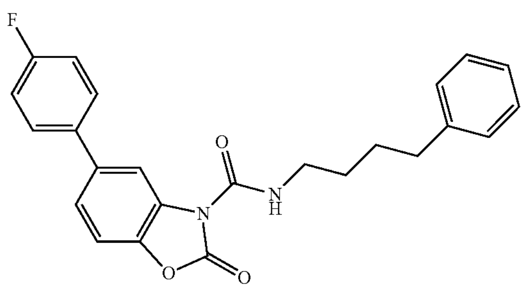 [SMILES: O=C(NCCCCc1ccccc1)n1c(=O)oc2ccc(-c3ccc(F)cc3)cc21] | $C_{24}H_{21}FN_2O_3$ | 404.4 | 5-(4-fluorophenyl)-2-oxo-N-(4-phenylbutyl)-1,3-benzoxazole-3-carboxamide |
| 23 | 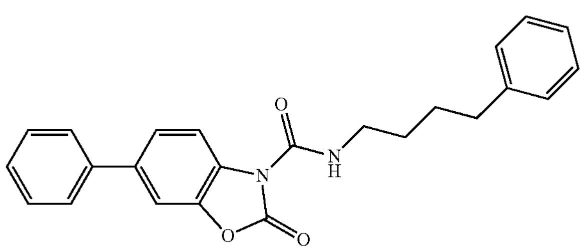 [SMILES: O=C(NCCCCc1ccccc1)n1c(=O)oc2cc(-c3ccccc3)ccc21] | $C_{24}H_{22}N_2O_3$ | 386.4 | 2-oxo-6-phenyl-N-(4-phenylbutyl)-1,3-benzoxazole-3-carboxamide |
| 24 | 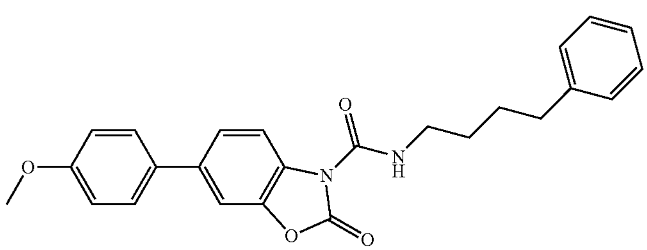 [SMILES: COc1ccc(-c2ccc3c(c2)oc(=O)n3C(=O)NCCCCc2ccccc2)cc1] | $C_{25}H_{24}N_2O_4$ | 416.5 | 6-(4-methoxyphenyl)-2-oxo-N-(4-phenylbutyl)-1,3-benzoxazole-3-carboxamide |
| 25 | 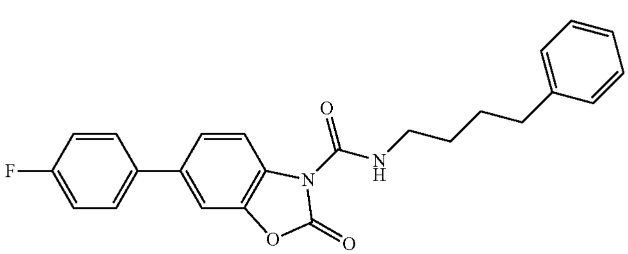 [SMILES: O=C(NCCCCc1ccccc1)n1c(=O)oc2cc(-c3ccc(F)cc3)ccc21] | $C_{24}H_{21}FN_2O_3$ | 404.4 | 6-(4-fluorophenyl)-2-oxo-N-(4-phenylbutyl)-1,3-benzoxazole-3-carboxamide |

TABLE 1-continued

Exemplified compounds of the invention

| Example | Structure | Formula | MW | Name |
|---|---|---|---|---|
| 26 | 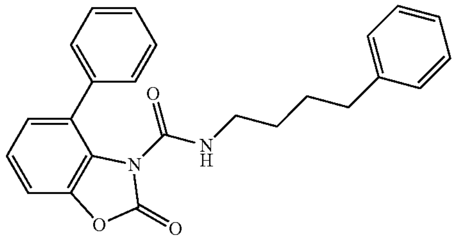 [SMILES: O=C(NCCCCc1ccccc1)n1c(=O)oc2cccc(-c3ccccc3)c21] | $C_{24}H_{22}N_2O_3$ | 386.4 | 2-oxo-4-phenyl-N-(4-phenylbutyl)-1,3-benzoxazole-3-carboxamide |
| 27 | 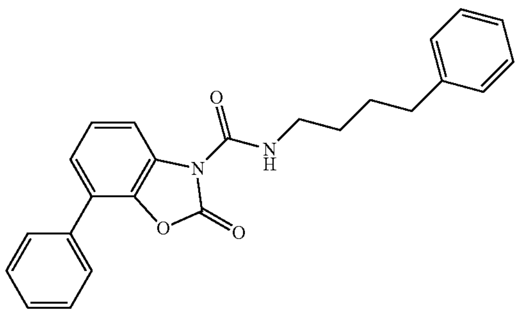 [SMILES: O=C(NCCCCc1ccccc1)n1c(=O)oc2c(-c3ccccc3)cccc21] | $C_{24}H_{22}N_2O_3$ | 386.4 | 2-oxo-7-phenyl-N-(4-phenylbutyl)-1,3-benzoxazole-3-carboxamide |
| 28 | 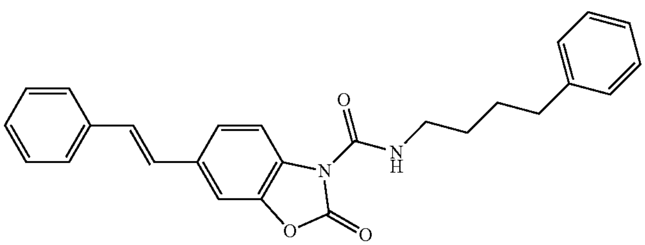 [SMILES: O=C(NCCCCc1ccccc1)n1c(=O)oc2cc(/C=C/c3ccccc3)ccc21] | $C_{26}H_{24}N_2O_3$ | 412.5 | 2-oxo-N-(4-phenylbutyl)-6-[(E)-styryl]-1,3-benzoxazole-3-carboxamide |
| 29 | 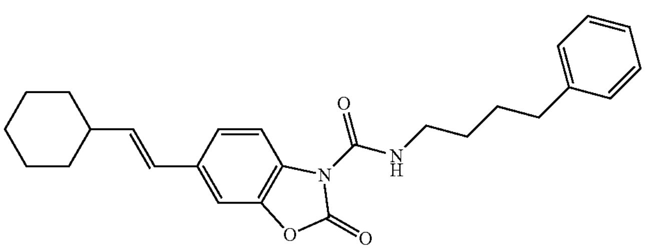 [SMILES: O=C(NCCCCc1ccccc1)n1c(=O)oc2cc(/C=C/C3CCCCC3)ccc21] | $C_{26}H_{30}N_2O_3$ | 418.5 | 6-[(E)-2-cyclohexylvinyl]-2-oxo-N-(4-phenylbutyl)-1,3-benzoxazole-3-carboxamide |
| 30 | 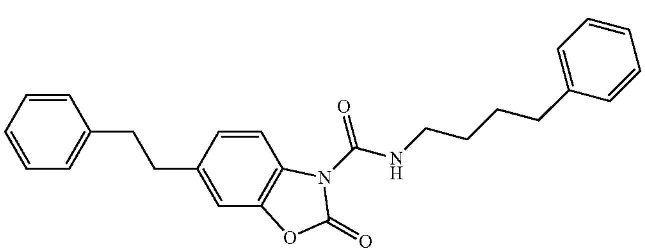 | $C_{26}H_{26}N_2O_3$ | 414.5 | 2-oxo-6-phenethyl-N-(4-phenylbutyl)-1,3-benzoxazole-3-carboxamide |

TABLE 1-continued

Exemplified compounds of the invention

| Example | Structure | Formula | MW | Name |
|---|---|---|---|---|
| 31 | 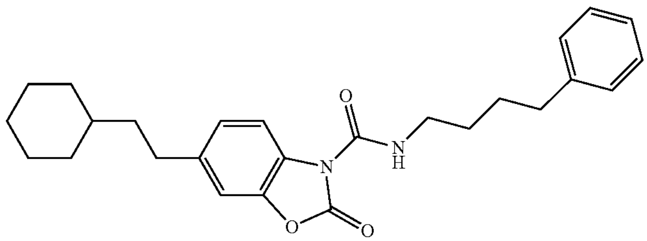 [SMILES: O=C(NCCCCc1ccccc1)n1c(=O)oc2cc(CCC3CCCCC3)ccc21] | $C_{26}H_{32}N_2O_3$ | 420.5 | 6-(2-cyclohexylethyl)-2-oxo-N-(4-phenylbutyl)-1,3-benzoxazole-3-carboxamide |
| 32 | 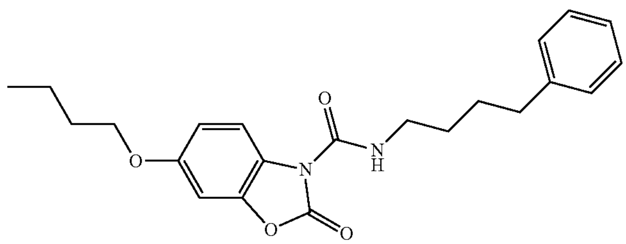 [SMILES: CCCCOc1ccc2c(c1)oc(=O)n2C(=O)NCCCCc1ccccc1] | $C_{22}H_{26}N_2O_4$ | 382.4 | 6-butoxy-2-oxo-N-(4-phenylbutyl)-1,3-benzoxazole-3-carboxamide |
| 33 | 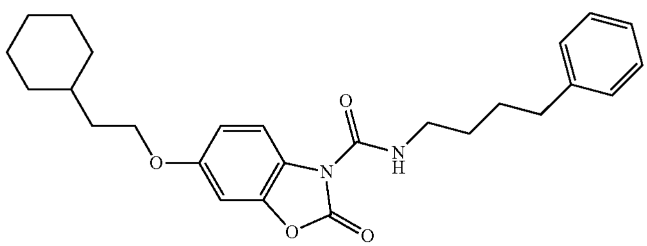 [SMILES: O=C(NCCCCc1ccccc1)n1c(=O)oc2cc(OCCC3CCCCC3)ccc21] | $C_{26}H_{32}N_2O_4$ | 436.5 | 6-(2-cyclohexylethoxy)-2-oxo-N-(4-phenylbutyl)-1,3-benzoxazole-3-carboxamide |
| 34 | 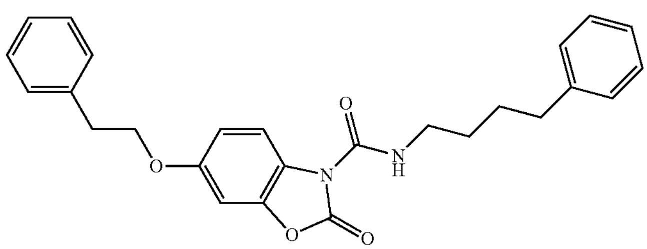 [SMILES: O=C(NCCCCc1ccccc1)n1c(=O)oc2cc(OCCc3ccccc3)ccc21] | $C_{26}H_{26}N_2O_4$ | 430.5 | 2-oxo-6-phenethyloxy-N-(4-phenylbutyl)-1,3-benzoxazole-3-carboxamide |
| 35 | 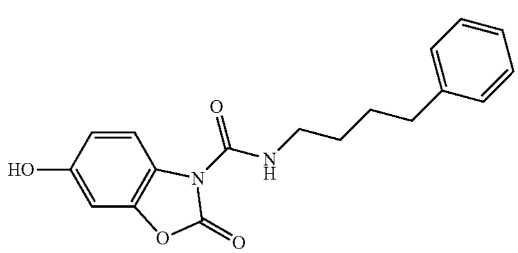 [SMILES: O=C(NCCCCc1ccccc1)n1c(=O)oc2cc(O)ccc21] | $C_{18}H_{18}N_2O_4$ | 326.4 | 6-hydroxy-2-oxo-N-(4-phenylbutyl)-1,3-benzoxazole-3-carboxamide |
| 36 | 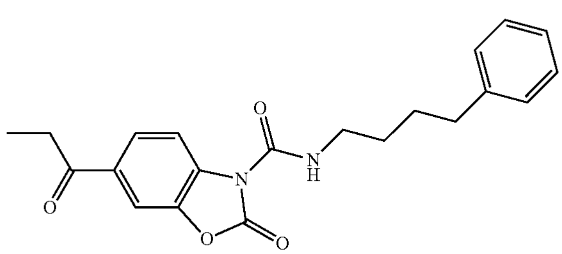 [SMILES: CCC(=O)c1ccc2c(c1)oc(=O)n2C(=O)NCCCCc1ccccc1] | $C_{21}H_{22}N_2O_4$ | 366.4 | 2-oxo-N-(4-phenylbutyl)-6-propanoyl-1,3-benzoxazole-3-carboxamide |

TABLE 1-continued

Exemplified compounds of the invention

| Example | Structure | Formula | MW | Name |
|---------|-----------|---------|-----|------|
| 37 | 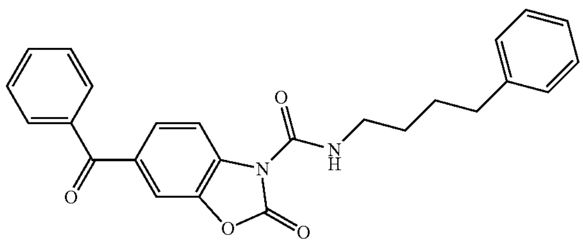 [SMILES: O=C(c1ccccc1)c1ccc2c(c1)oc(=O)n2C(=O)NCCCCc1ccccc1] | $C_{25}H_{22}N_2O_4$ | 414.4 | 6-benzoyl-2-oxo-N-(4-phenyl-butyl)-1,3-benzoxazole-3-carboxamide |
| 38 | 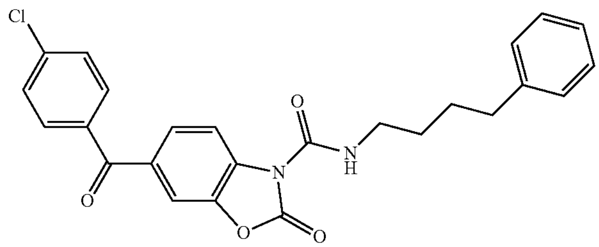 [SMILES: O=C(c1ccc(Cl)cc1)c1ccc2c(c1)oc(=O)n2C(=O)NCCCCc1ccccc1] | $C_{25}H_{21}ClN_2O_4$ | 448.9 | 6-(4-chlorobenzoyl)-2-oxo-N-(4-phenylbutyl)-1,3-benzoxazole-3-carboxamide |
| 39 | 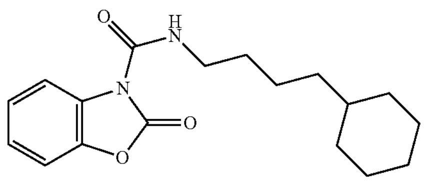 [SMILES: O=C(NCCCCC1CCCCC1)n1c(=O)oc2ccccc21] | $C_{18}H_{24}N_2O_3$ | 316.4 | N-(4-cyclohexylbutyl)-2-oxo-1,3-benzoxazole-3-carboxamide |
| 40 | 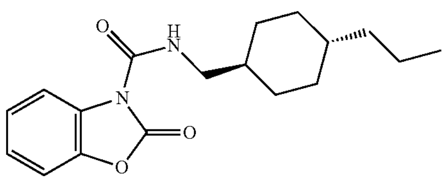 [SMILES: CCC[C@H]1CC[C@H](CNC(=O)n2c(=O)oc3ccccc32)CC1] | $C_{18}H_{24}N_2O_3$ | 316.4 | 2-oxo-N-[(4-propylcyclohexyl)methyl]-1,3-benzoxazole-3-carboxamide |
| 41 | 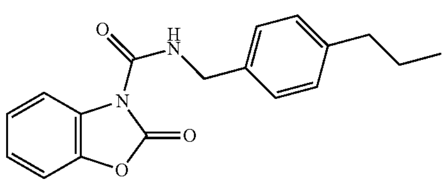 [SMILES: CCCc1ccc(CNC(=O)n2c(=O)oc3ccccc32)cc1] | $C_{18}H_{18}N_2O_3$ | 310.4 | 2-oxo-N-[(4-propylphenyl)methyl]-1,3-benzoxazole-3-carboxamide |
| 42 | 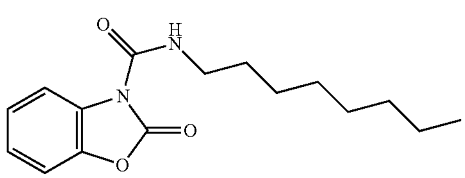 [SMILES: CCCCCCCCNC(=O)n1c(=O)oc2ccccc21] | $C_{16}H_{22}N_2O_3$ | 290.4 | N-octyl-2-oxo-1,3-benzoxazole-3-carboxamide |
| 43 | 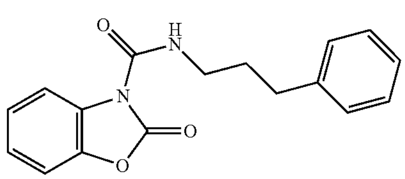 [SMILES: O=C(NCCCc1ccccc1)n1c(=O)oc2ccccc21] | $C_{17}H_{16}N_2O_3$ | 296.3 | 2-oxo-N-(3-phenylpropyl)-1,3-benzoxazole-3-carboxamide |

TABLE 1-continued

Exemplified compounds of the invention

| Example | Structure | Formula | MW | Name |
|---|---|---|---|---|
| 44 | 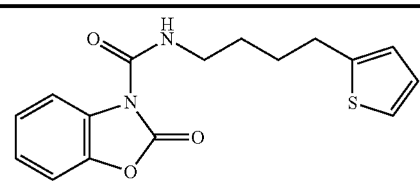 | $C_{16}H_{16}N_2O_3S$ | 316.4 | 2-oxo-N-[4-(2-thienyl)butyl]-1,3-benzoxazole-3-carboxamide |
| 45 | 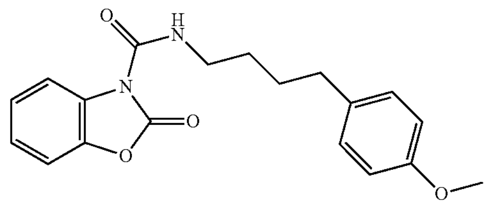 [SMILES: COc1ccc(CCCCNC(=O)n2c(=O)oc3ccccc32)cc1] | $C_{19}H_{20}N_2O_4$ | 340.4 | N-[4-(4-methoxyphenyl)butyl]-2-oxo-1,3-benzoxazole-3-carboxamide |
| 46 | 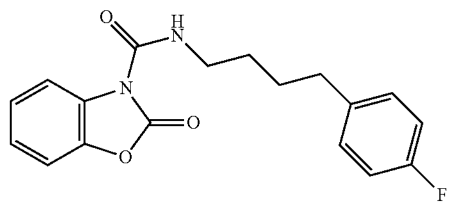 [SMILES: O=C(NCCCCc1ccc(F)cc1)n1c(=O)oc2ccccc21] | $C_{18}H_{17}FN_2O_3$ | 328.3 | N-[4-(4-fluorophenyl)butyl]-2-oxo-1,3-benzoxazole-3-carboxamide |
| 47 | 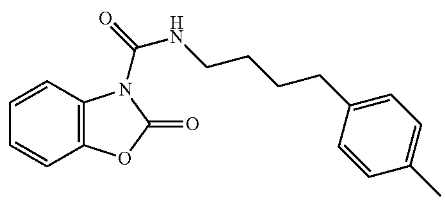 [SMILES: Cc1ccc(CCCCNC(=O)n2c(=O)oc3ccccc32)cc1] | $C_{19}H_{20}N_2O_3$ | 324.4 | 2-oxo-N-[4-(p-tolyl)butyl]-1,3-benzoxazole-3-carboxamide |
| 48 | 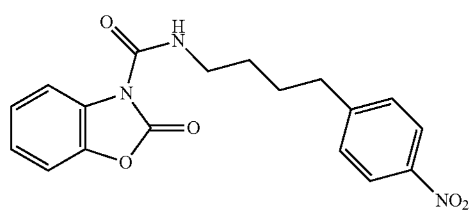 [SMILES: O=C(NCCCCc1ccc([N+](=O)[O-])cc1)n1c(=O)oc2ccccc21] | $C_{18}H_{17}N_3O_5$ | 355.3 | N-[4-(4-nitrophenyl)butyl]-2-oxo-1,3-benzoxazole-3-carboxamide |
| 49 | 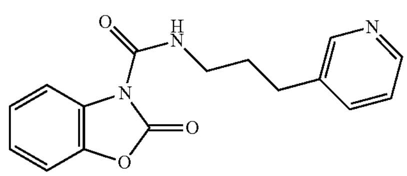 [SMILES: O=C(NCCCc1cccnc1)n1c(=O)oc2ccccc21] | $C_{16}H_{15}N_3O_3$ | 297.3 | 2-oxo-N-[3-(3-pyridyl)propyl]-1,3-benzoxazole-3-carboxamide |
| 50 | 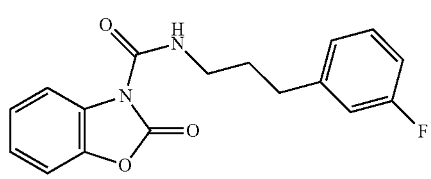 [SMILES: O=C(NCCCc1cccc(F)c1)n1c(=O)oc2ccccc21] | $C_{17}H_{15}FN_2O_3$ | 314.3 | N-[3-(3-fluorophenyl)propyl]-2-oxo-1,3-benzoxazole-3-carboxamide |
| 51 | 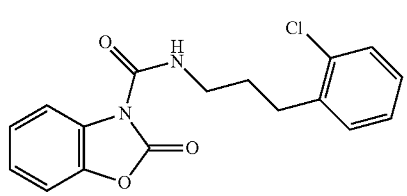 [SMILES: O=C(NCCCc1ccccc1Cl)n1c(=O)oc2ccccc21] | $C_{17}H_{15}ClN_2O_3$ | 330.8 | N-[3-(2-chlorophenyl)propyl]-2-oxo-1,3-benzoxazole-3-carboxamide |

TABLE 1-continued

Exemplified compounds of the invention

| Example | Structure | Formula | MW | Name |
|---|---|---|---|---|
| 52 | 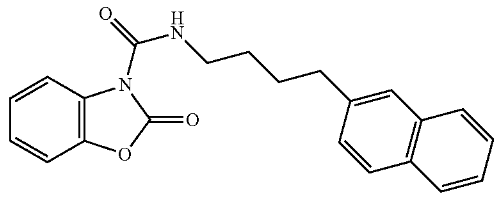 [SMILES: O=C(NCCCCc1ccc2ccccc2c1)n1c(=O)oc2ccccc21] | $C_{22}H_{20}N_2O_3$ | 360.4 | N-[4-(2-naphthyl)butyl]-2-oxo-1,3-benzoxazole-3-carboxamide |
| 53 | 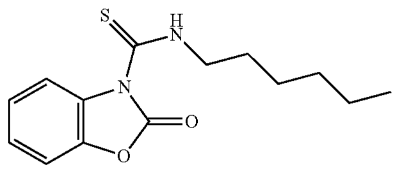 [SMILES: CCCCCCNC(=S)n1c(=O)oc2ccccc21] | $C_{14}H_{18}N_2O_2S$ | 278.4 | N-hexyl-2-oxo-1,3-benzoxazole-3-carbothioamide |
| 54 | 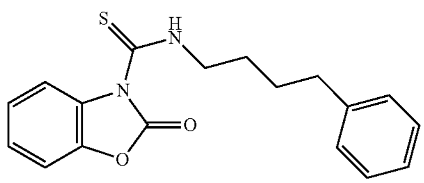 [SMILES: O=c1oc2ccccc2n1C(=S)NCCCCc1ccccc1] | $C_{18}H_{18}N_2O_2S$ | 326.4 | 2-oxo-N-(4-phenylbutyl)-1,3-benzoxazole-3-carbothioamide |
| 55 | 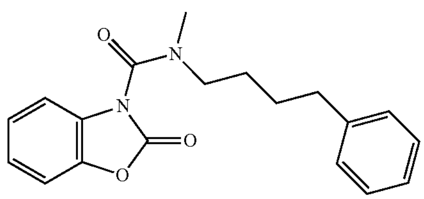 [SMILES: CN(CCCCc1ccccc1)C(=O)n1c(=O)oc2ccccc21] | $C_{19}H_{20}N_2O_3$ | 324.4 | N-methyl-2-oxo-N-(4-phenylbutyl)-1,3-benzoxazole-3-carboxamide |
| 56 | 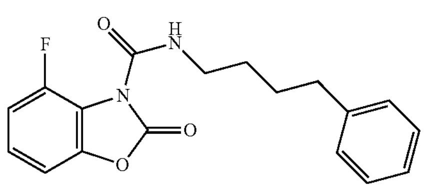 [SMILES: O=C(NCCCCc1ccccc1)n1c(=O)oc2cccc(F)c21] | $C_{18}H_{17}FN_2O_3$ | 328.3 | 4-fluoro-2-oxo-N-(4-phenylbutyl)-1,3-benzoxazole-3-carboxamide |
| 57 | 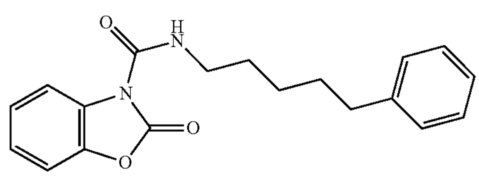 [SMILES: O=C(NCCCCCc1ccccc1)n1c(=O)oc2ccccc21] | $C_{19}H_{20}N_2O_3$ | 324.4 | 2-oxo-N-(5-phenylpentyl)-1,3-benzoxazole-3-carboxamide |
| 58 | 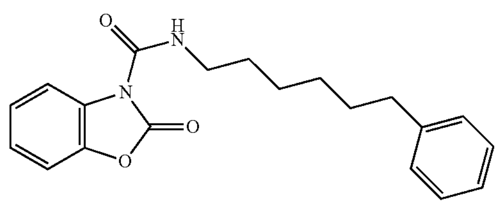 [SMILES: O=C(NCCCCCCc1ccccc1)n1c(=O)oc2ccccc21] | $C_{20}H_{22}N_2O_3$ | 338.4 | 2-oxo-N-(6-phenylhexyl)-1,3-benzoxazole-3-carboxamide |
| 59 | 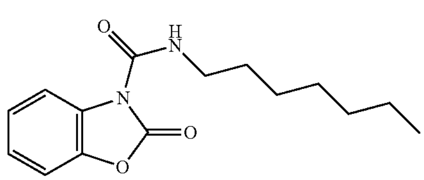 [SMILES: CCCCCCCNC(=O)n1c(=O)oc2ccccc21] | $C_{15}H_{20}N_2O_3$ | 276.3 | N-heptyl-2-oxo-1,3-benzoxazole-3-carboxamide |

TABLE 2

IC$_{50}$ values of selected compounds of the invention on human (hAC) acid ceramidase, via fluorescent-based in vitro assay

| Example | IC$_{50}$ (nM) ± SD | n |
|---|---|---|
| 1 | 64 ± 7 | 3 |
| 2 | 56 ± 12 | 2 |
| 3 | 10 ± 7 | 2 |
| 4 | 9 ± 7 | 2 |
| 5 | 33 ± 4 | 3 |
| 6 | 22 ± 11 | 3 |
| 7 | 33 ± 9 | 3 |
| 8 | 117 ± 26 | 3 |
| 9 | 66 ± 9 | 3 |
| 10 | 52 ± 9 | 3 |
| 11 | 3 ± 2 | 3 |
| 12 | 3 ± 1 | 3 |
| 13 | 11 ± 5 | 2 |
| 14 | 20 ± 9 | 3 |
| 15 | 11 | 1 |
| 16 | 18 ± 8 | 3 |
| 18 | 23 ± 5 | 2 |
| 19 | 18 ± 11 | 3 |
| 20 | 22 | 1 |
| 21 | 68 | 1 |
| 22 | 56 ± 14 | 2 |
| 23 | 84 ± 35 | 3 |
| 24 | 67 ± 5 | 2 |
| 25 | 79 ± 31 | 3 |
| 26 | 0.8 ± 0.1 | 2 |
| 27 | 91 ± 10 | 2 |
| 35 | 152 ± 87 | 3 |
| 36 | 16 ± 14 | 2 |
| 37 | 29 ± 1 | 2 |
| 38 | 14 ± 4 | 2 |
| 39 | 62 ± 44 | 2 |
| 40 | 135 ± 56 | 3 |
| 41 | 19 ± 2 | 2 |
| 42 | 34 ± 14 | 3 |
| 43 | 55 ± 6 | 2 |
| 44 | 99 ± 58 | 3 |
| 45 | 63 ± 22 | 2 |
| 46 | 75 ± 0 | 2 |
| 47 | 28 | 1 |
| 50 | 49 | 1 |
| 52 | 57 | 1 |
| 56 | 1 ± 1 | 2 |
| 57 | 54 ± 12 | 3 |
| 58 | 99 ± 58 | 3 |
| 59 | 50 ± 7 | 2 |

Biological Activity of the Compounds of the Invention

Selected compounds of the invention were evaluated for their capacity of inhibiting acid ceramidase in vitro and ex vivo. Acid ceramidase activity, different ceramides and dihydroceramides species were measured in human colon adenocarcinoma and melanoma cell lines. Synergism with 5-fluorouracil (5-FU) was evaluated in human colon adenocarcinoma cells.

Example A

Figure 2:
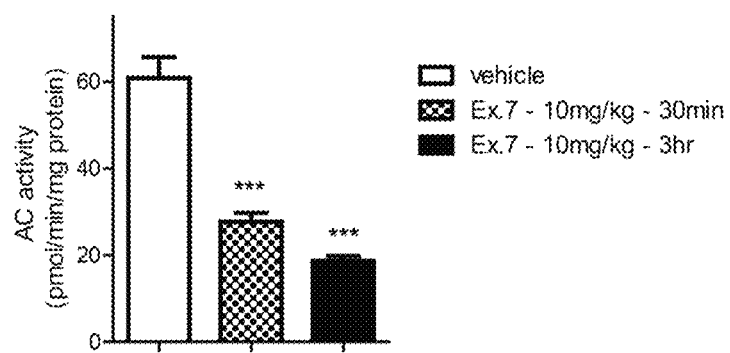
FIG. 2 shows a bar graph illustrating the effect of compound of Example 7 on AC activity ex vivo. Specifically, it is evidences the effects of compound of Example 7 or vehicle (15% polyethylene glycol, 15% Tween80, 70% saline) on AC activity in mouse lungs. AC activity measured ex vivo 30 minutes or 3 hours after intraperitoneal injection of compound of Example 7 (10 mg·$kg^{-1}$). Results are expressed as mean±s.e.m. (n=6). ***p<0.001 vs vehicle, one-way ANOVA followed by Dunnet.

Treating cultures of human melanoma A375 and MeWo cells with compound of Example 7 (25 µM) caused a reduction in AC activity already evident at 30 minutes and that lasted up to 3 hours (FIG. 1A-B). This effect was accompanied by intracellular accumulation of various ceramide species, including cer(d18:1/14:0), cer(d18:1/16:0), cer(d18:1/18:0) and cer(d18:1/24:1) (LC/MS), which were identified and quantified by liquid chromatography/mass spectrometry (FIG. 1 D-E). Moreover, compound of Example 7 induced a significant increase in all di-hydro ceramide species analyzed (FIG. 1 G-H), proving that AC inhibition is responsible for the effect. These effects lasted up to 24 hours in A375 cells (low AC expression), while MeWo cells (high AC expression) recovered the initial phenotype after 24 hours. Furthermore, systemic administration of compound of Example 7 (10 mg·kg$^{-1}$, intraperitoneal, i.p.) to mice produced a time-dependent inhibition of AC activity in lungs (FIG. 2) after 30 minutes or 3 hours.

Example B

Figure 3:
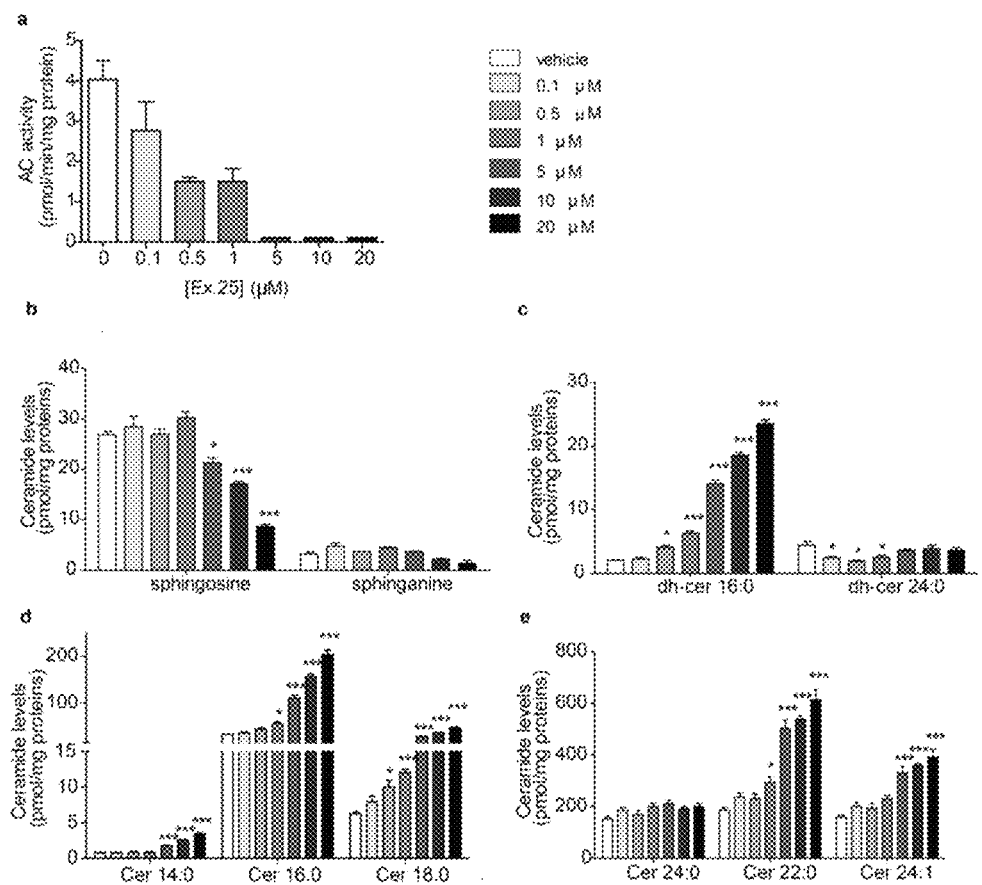
FIG. 3 shows five bar graphs illustrating the concentration response of compound of Example 25 on AC activity and ceramide levels in a mouse leukaemic monocyte macrophage cell line. Specifically it is reported the concentration response of compound of Example 25 or vehicle (0.1% DMSO in DMEM) on AC activity and ceramide levels in RAW264.7 murine cell line. (A) Intact cells were treated with compound of Example 25 (0.1-20 μM) or vehicle and AC activity was measured 3 hours later in cell lysates. (B-E) Intact cells were exposed to compound of Example 25 (0.1-20 μM) for 3 hours and sphingosine/sphinganine (B), dihydroceramides (C), medium chain ceramides (D), long chain ceramides (E) were quantified. Results are expressed as mean±s.e.m. (n=3). *p<0.05, p<0.01, *p<0.001 vs vehicle, two-way ANOVA followed by Dunnet.

Compound of Example 25 was first tested on a mouse leukaemic monocyte macrophage cell line (Raw264.7) as a model for inflammation: as shown in FIG. 3, treating Raw264.7 cells with compound of Example 25 caused a concentration dependent reduction in AC activity (FIG. 3A), associated with a parallel decrease in sphingosine levels (FIG. 3B), the product of AC reaction. At the same time, we observed an intracellular accumulation of various di-hydro ceramides and ceramide species (FIG. 3 C-D-E), which were identified and quantified by liquid chromatography/mass spectrometry.

Figure 4:
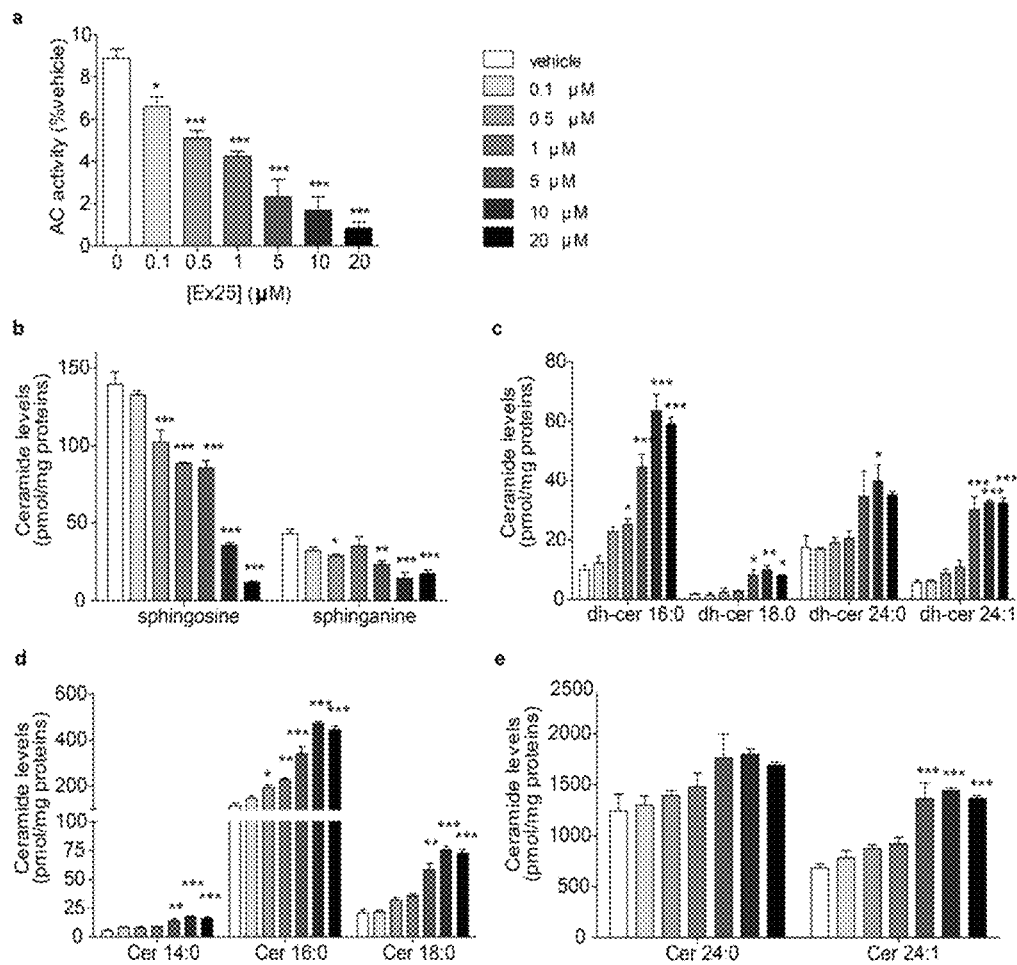
FIG. 4 shows two bar graphs illustrating the concentration response of compound of Example 25 on AC activity and ceramide levels in a human colon adenocarcinoma cell line: Specifically, the Concentration response of compound of Example 25 or vehicle (0.1% DMSO in DMEM) on AC activity and ceramide levels in SW403 human colon adenocarcinoma cell line, is reported. (A) Intact cells were treated with compound of Example 25 (0.1-20 μM) or vehicle and AC activity was measured 3 hours later in cell lysates. (B-E) Intact cells were exposed to compound of Example 25 (0.1-20 μM) for 3 hours and sphingosine/sphinganine (B), dihydroceramides (C), medium chain ceramides (D), long chain ceramides (E) were quantified. Results are expressed as mean±s.e.m. (n=3). *p<0.05, p<0.01, *p<0.001 vs vehicle, two-way ANOVA followed by Dunnet.
Figure 5:
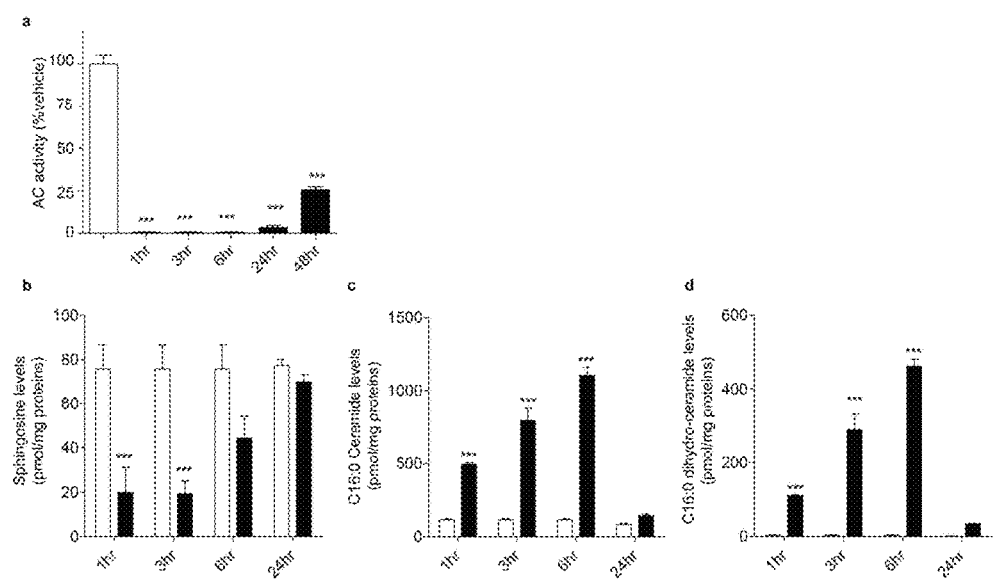
FIG. 5 shows four bar graphs reporting the timecourse of compound of Example 25 on AC activity and ceramide levels in a human colon adenocarcinoma cell line, Specifically FIG. 5 reports the timecourse of compound of Example 25 or vehicle (0.1% DMSO in DMEM) on AC activity and ceramide levels in SW403 human colon adenocarcinoma cell line. (A) Intact cells were treated with compound of Example 25 (20 μM) and AC activity was measured 1 to 48 hours later in cell lysates. (B-E) Intact cells were exposed to compound of Example 25 (20 μM) and sphingosine (B), C16:0 dihydroceramide (C), C16:0 ceramide (D) were quantified. Results are expressed as mean±s.e.m. (n=3). *p<0.05, p<0.01, *p<0.001 vs vehicle, two-way ANOVA followed by Dunnet.

Similar results were obtained with compound of Example 25 in human colon adenocarcinoma cells (SW403) as a model for cancer. Treating SW403 cells with compound of Example 25 caused a concentration dependent reduction in AC activity (FIG. 4A), associated with a parallel decrease in sphingosine levels (FIG. 4B), the product of AC reaction. At the same time, we observed an intracellular accumulation of various di-hydro ceramides and ceramide species (FIG. 4 C-D-E), which were identified and quantified by liquid chromatography/mass spectrometry. A timecourse experiment demonstrated that these effects are significant as early as 1 hour and lasted at least for 6 hours (FIG. 5).

Figure 6:
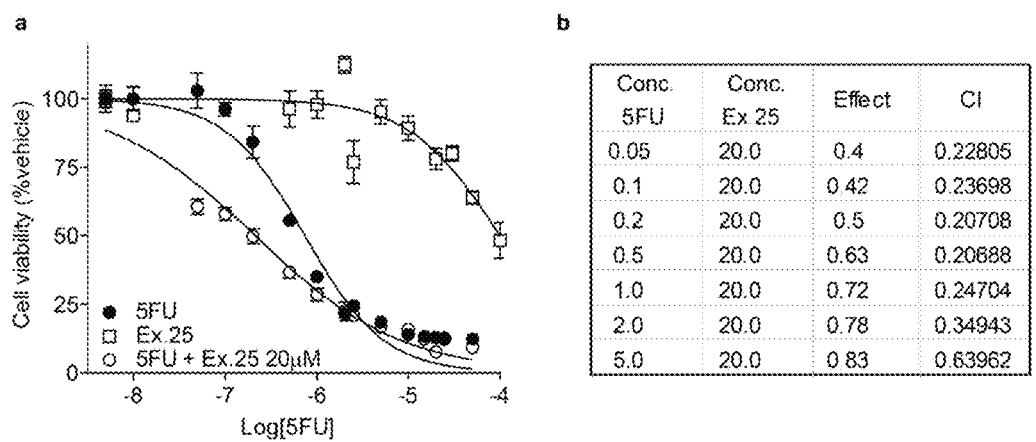
FIG. 6 illustrates a graph and a Table showing the synergism of compound of Example 25 in combination with 5-FU on cell viability in a human colon adenocarcinoma cell line. Specifically the effects of compound of Example 25 (□) and 5-FU (●) or a combination of the two (○) on SW403 cell viability measured with CellTiterGlo assay (A) are evidenced. Combinatory index calculation of cell viability data analyzed with CompuSyn Software. The resulting combination index (CI) offers quantitative definition for additive effect (CI=1), synergism (CI<1), and antagonism (CI>1) in drug combinations. Results are expressed as mean±s.e.m. (n=8-16) of three independent experiments.

To test whether AC inhibition potentiates the effects of the classic chemotherapeutic drug 5-FU in a synergistic manner, we incubated SW403 cells with a sub-effective concentration of compound of Example 25 (20 µM) along with varying concentrations of 5-FU. The compounds were added to the cultures once every 24 hours over a period of 72 hours and the effects of the combined treatments were evaluated using CompuSyn Software. The analyses showed that compound of Example 25 acted synergistically with 5-FU to reduce SW403 cell viability (FIG. 6A). Indeed, experimental EC$_{50}$ values were 0.736 µM for 5-FU and 0.21 µM for the combination compound of Example 25 plus 5-FU. These results indicated a synergistic effect, as demonstrated by the combinatory index analysis (FIG. 6B).

Figure 7:
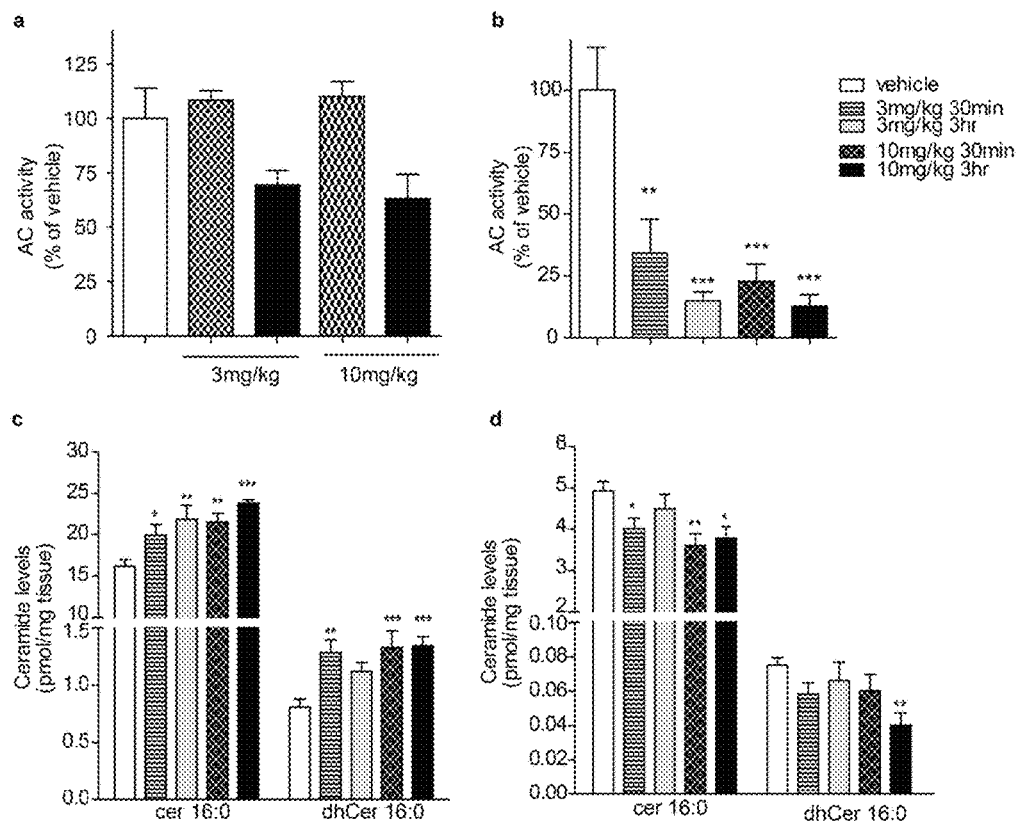
FIG. 7 shows four bar graphs illustrating the effect of compound of Example 25 on AC activity and ceramides ex vivo. Specifically.

Furthermore, systemic administration of compound of Example 25 (3 or 10 mg·kg$^{-1}$, intraperitoneal, i.p. or oral) to mice produced a time and dose-dependent inhibition of AC activity in various tissues, including lungs (FIG. 7A) and brain cortex (FIG. 7B).

Comparative Example

Experimental evidence of lack of inhibitory activity of the compounds of the invention towards the molecular/biological targets (MAG-hydrolyzing enzymes including MGL, HSL and EL) of the benzooxazol-2-one derivatives disclosed in U.S. Pat. No. 7,709,513 B2 (WO2006/131233A1) as effective lipase and phospholipase inhibitors.

Premise

| Enzyme tested | Classification | Mean (value 1; value 2) |
|---|---|---|

The compounds of Formula (I) and Formula (Ia) of the invention inhibit AC in vitro and in vivo, resulting in an increase in the levels of ceramides and a decrease in the levels of sphingosine and its bioactive metabolite sphingosine-1-phosphate.

Comparative Test A (Lack of Off-Target Activity)

Compound of Example 25 falling in both Formula (I) and (Ia) was selected to be tested for off-target effects on a set of enzymes that include proteases (aspartic, cysteine, and serine), cyclooxygenases as well as lipoxygenases and group IV phospholipase (sPLA2) (Table 3).

The tests carried out prove that compound of Example 25 has not any significant activity towards the above mentioned biological targets.

TABLE 3

Inhibitory activity (% Inh. at 10 μM) of compound of Example 25 against a set of enzymes.[a]

| | | |
|---|---|---|
| sPLA2 (h) (type V) | Phospholipase | 1.1 (1.7; 0.5) |
| PLC | Phospholipase | −19.7 (−19.9; −19.4) |
| COX1 (h) | Cyclooxygenase | −6.1 (−10.4; −1.8) |
| COX2 (h) | Cyclooxygenase | 6.7 (−3.2; 16.6) |
| 5-lipoxygenase (h) | Lipoxygenase | 15.2 (17.6; 12.9) |
| 12-lipoxygenase (h) | Lipoxygenase | 16.2 (11.6; 20.7) |
| 15-lipoxygenase-2 (h) (recombinant) | Lipoxygenase | −33.3 (−23.2; −43.3) |
| BACE-1 (h) (β-secretase) | Aspartic protease | −13.3 (−13.8; −12.9) |
| cathepsin D (h) | Aspartic protease | 67.0 (67.1; 66.9) |
| caspase-3 (h) | Cysteine protease | 1.9 (2.6; 1.3) |
| caspase-8 (h) | Cysteine protease | −0.9 (−0.3; −1.5) |
| cathepsin B (h) | Cysteine protease | 9.9 (1.7; 18) |
| cathepsin G (h) | Serine protease | 16.6 (6.3; 27) |
| MMP-2 (h) | Metalloprotease | 7.2 (7.3; 7.1) |

[a]The screening was performed by Cerep at 10 μM concentration of Ex. 25. Compound enzyme inhibition effect was calculated as % inhibition of control enzyme activity. Values are expressed as means of two determinations.

Comparative Test B

Compound of Example 25 was also tested for its ability to inhibit the hydrolytic degradation of diacylglycerols (DAG) and monoacylglycerols (MAG) in live mice. DAG and MAG hydrolysis is catalyzed by multiple serine lipases, including diacylglycerol lipase (DGL), monoacylglycerol lipase (MGL), hormone-sensitive lipase (HSL), and endothelial lipase. Thus, by monitoring the effects of compound of Example 25 on MAG-hydrolysing activity as well as DAG and MAG levels ex vivo, we can gain important insights as to the ability of the compound to interfere with those lipases in a physiologically relevant setting.

Figure 8:
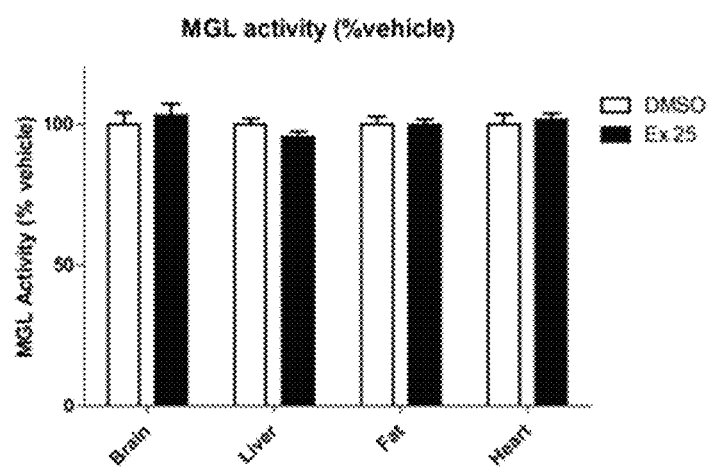
FIG. 8 illustrates the effect of compound of Example 25 on mouse MAG-hydrolysing activity ex vivo.

As illustrated in FIG. 8, the systemic administration of compound of Example 25 (10 mg-kg$^{-1}$, intraperitoneal, i.p.) to mice did not cause inhibition of MAG-hydrolysing activity in fat and other body organs, including brain, liver and heart. Specifically FIG. 8 evidences the effect of Example 25 or vehicle (DMSO) on MGL activity in brain, liver, fat and heart. MAG-hydrolysing activity was measured 3 h after intraperitoneal injection of compound of Example 25 (10 mg-kg-1). Results are expressed as mean±s.e.m. (n=5).

Figure 9:
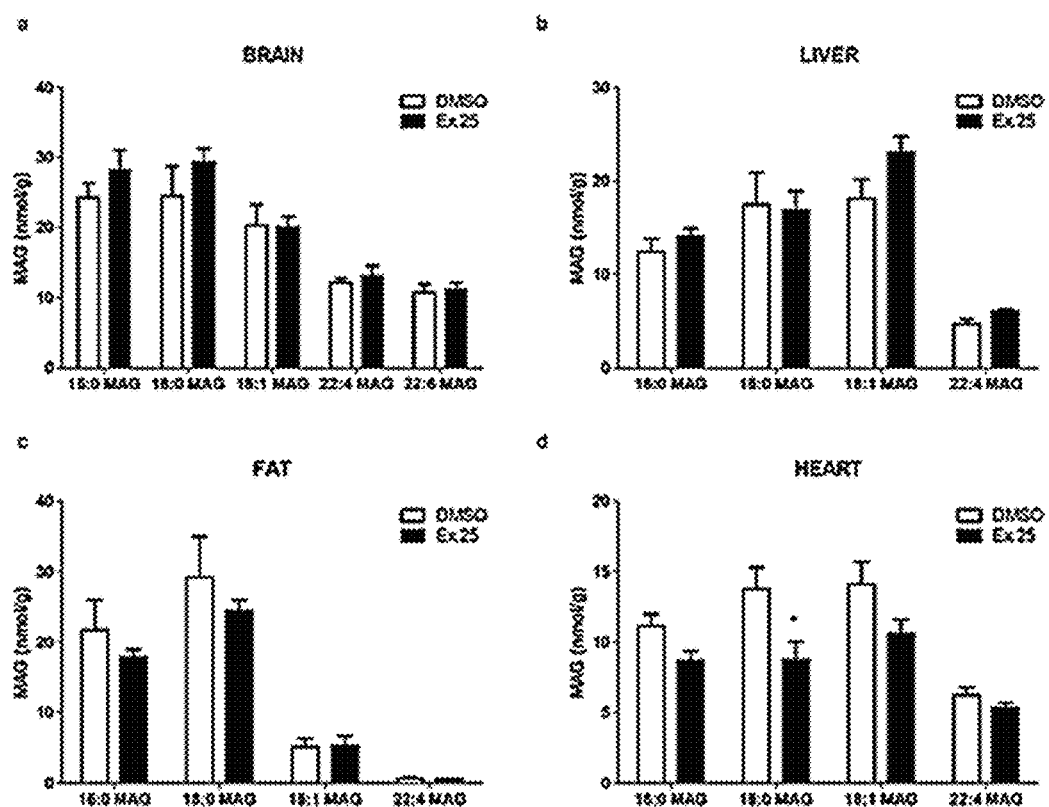
FIG. 9 shows the effect of compound of Example 25 on various MAG levels in brain, liver, fat and heart.

Furthermore, as illustrated in FIG. 9, the levels of the most representative MAGs in these tissues remained unchanged. Specifically, the levels of MAGs were quantified after 3 hours after intraperitoneal injection of compound of Example 25 (10 mg-kg-1). Specifically, levels of 16:0 MAG, 18:0 MAG, 18:1 MAG, 22:4 MAG, 22:6 MAG were measured in the brain (a); levels of 16:0 MAG, 18:0 MAG, 18:1 MAG, 22:4 MAG were measured in the liver (b), in fat (c) and in the heart (d). Results are expressed as mean±s.e.m. (n=5).

These results demonstrate that compound of Example 25 has no inhibitory activity toward any MGL-hydrolysing enzymes in mice, including monoacylglycerol lipase (MGL), hormone-sensitive lipase (HSL), and endothelial lipase disclosed in U.S. Pat. No. 7,709,513 B2 (WO2006/131233A1).

Methods

Procedure for Lipid Extraction

We homogenized tissue samples (20-30 mg) in methanol (1 mL) containing deuterium-labeled 2-AG (500 pmol) as internal standard (Cayman, Ann Arbor, Mich.). We extracted lipids with chloroform (2 mL) and water (1 mL). The organic phases were dried in a stream of N$_2$, reconstituted in chloroform (2 mL) and fractionated by open-bed silica gel column chromatography as described. The eluded fraction containing 2-AG and anandamide were dried under N$_2$, and residues were suspended in chloroform/methanol (1:3, vol:vol; 100 μL). Analyses were conducted using a liquid chromatography mass spectrometry (LC-MS) apparatus consisting of an Agilent 1100 system and 1946D mass spectrometer detector equipped with ESI interface (Agilent Technologies, Santa Clara, Calif., USA).

Procedure for LC-MS Based Assay

Tissue was homogenized in ice-cold Tris-HCl (50 mM, pH7.5, 10 vol) containing sucrose (0.32 M). Homogenates were centrifuged at 1,000×g for 10 min, and the supernatants (5 μg of protein) were incubated at 37° C. for 30 min in Tris.HCl (50 mM, pH 7.5, 0.5 mL) containing 10 μM oleoylglycerol (Sigma-Aldrich, St. Louis, Mo.). Reactions were stopped by adding 1.5 mL of chloroform/methanol (2:1, v:v) containing 17:0 fatty acid (m/z=269) as an internal standard. After centrifugation at 1,000×g at 4° C. for 10 min, the organic layers were collected and dried under N$_2$. The residues were suspended in 100 μL of chloroform/methanol (1:3, v:v) and analyzed by LC-MS.

The invention claimed is:

1. A compound of Formula (Ia) or a pharmaceutically acceptable salt thereof

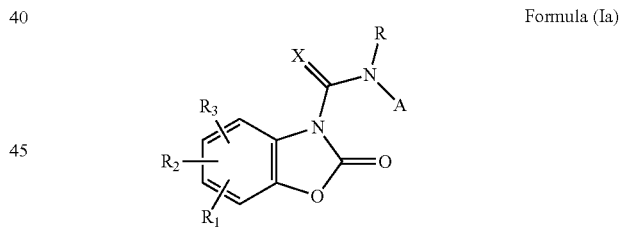

Formula (Ia)

wherein:

X is O or S;

R is hydrogen or linear or branched $C_{1-6}$ alkyl;

A is a linear or branched $C_{5-12}$ alkyl group or a group:

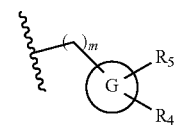

wherein:

m is an integer from 1 to 6;

G is a 3-10 membered saturated or unsaturated, aromatic or heteroaromatic, single or fused ring comprising up to three heteroatoms selected from N, O, S; and $R_4$ and $R_5$ are as defined below;

$R_1$, $R_2$, $R_3$, $R_4$ and $R_5$, are independently selected from the group consisting of hydrogen, halogen, linear or branched $C_{1-6}$ alkyl, optionally substituted cycloalkyl $C_{1-6}$ alkyl, optionally substituted cycloalkyl $C_{2-6}$ alkenyl, optionally substituted aryl $C_{1-6}$ alkyl, optionally substituted aryl $C_{2-6}$ alkyenyl, optionally substituted cycloalkyl $C_{1-6}$ alkoxy, optionally substituted aryl $C_{1-6}$ lkoxy, hydroxy $C_{1-6}$ alkyl, OH, fluoro $C_{1-6}$ alkyl, fluoro $C_{1-6}$ alkoxy, substituted aryl, optionally substituted arylCO, and optionally substituted aryl $C_{1-6}$ alkylCO, wherein $R_1$, $R_2$, $R_3$, $R_4$ and $R_5$ can be attached to any position of the ring to which they are connected, with the proviso that at least one amongst $R_1$, $R_2$ and $R_3$ is different from hydrogen, halogen and alkyl and when m is 1 and $R_4$ and $R_5$ are both hydrogen, or one is hydrogen and the other is Me, then G is not a benzene ring.

2. A compound of Formula (Ia) according to claim 1, wherein:

X is O or S;

R is hydrogen;

A is a linear or branched $C_{5-9}$ alkyl group or a group

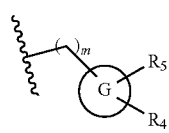

wherein:

m is an integer from 3 to 6

G is phenyl, thienyl, pyridyl, naphthyl or $C_{3-7}$ cycloalkyl; and $R_1$, $R_2$, $R_3$, $R_4$ and $R_5$ are independently selected from the group consisting of hydrogen, optionally substituted cyclohexylethyl, optionally substituted cyclohexylethenyl, optionally substituted phenyl ethyl, optionally substituted phenylethenyl, optionally substituted cyclohexylethoxy, optionally substituted phenylethoxy, $HOCH_2$, $CF_2H$, $CFH_2$, $CF_3CF_2$, $CF_3O$, $CF_3CF_2O$, substituted phenyl, optionally substituted phenylCO, and optionally substituted phenyl$_{1-6}$ alkylCO, wherein $R_1$, $R_2$, $R_3$, $R_4$ and $R_5$ can be attached to any position of the ring to which they are connected, with the proviso that at least one amongst $R_1$, $R_2$ and $R_3$ is different from hydrogen.

3. A pharmaceutical composition comprising an effective amount of a compound of claim 1 or a pharmaceutically acceptable salt thereof and a pharmaceutically acceptable carrier.

4. A pharmaceutical composition according to claim 3 further comprising a pharmaceutically active ingredient.

5. A pharmaceutical composition according to claim 4 wherein the pharmaceutically active ingredient is an anticancer agent, an antiinflammatory agent, an analgesic compound, an agent effective on pulmonary diseases or mixtures thereof.

6. A compound having the formula:

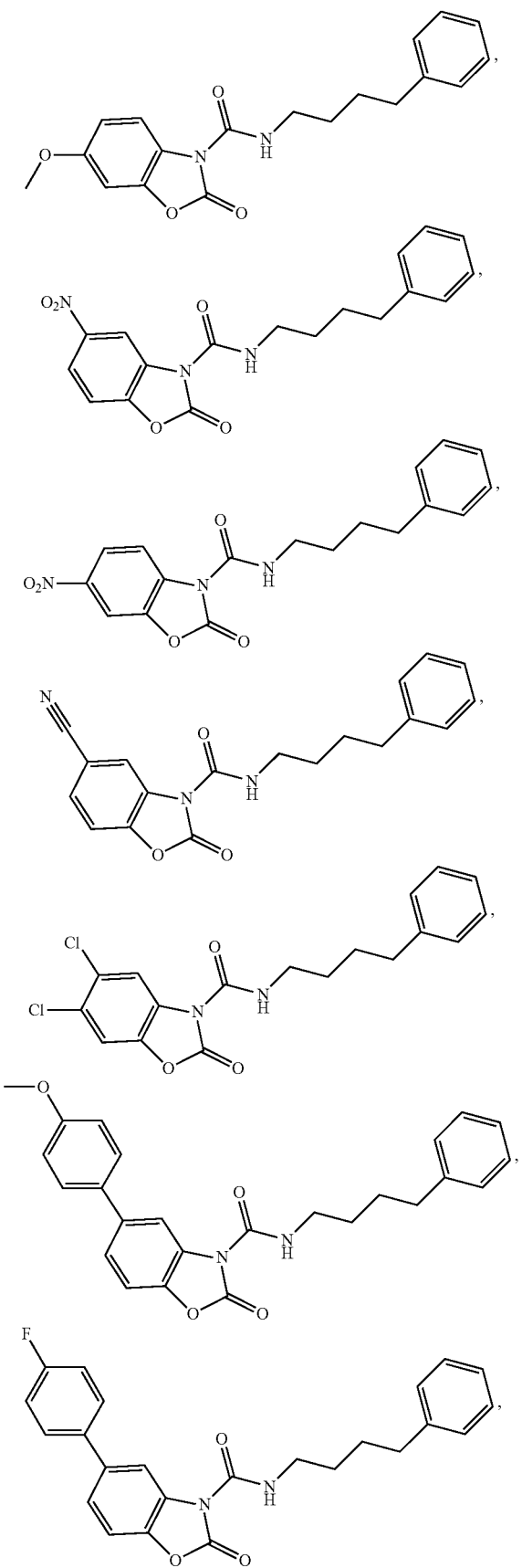

97
-continued
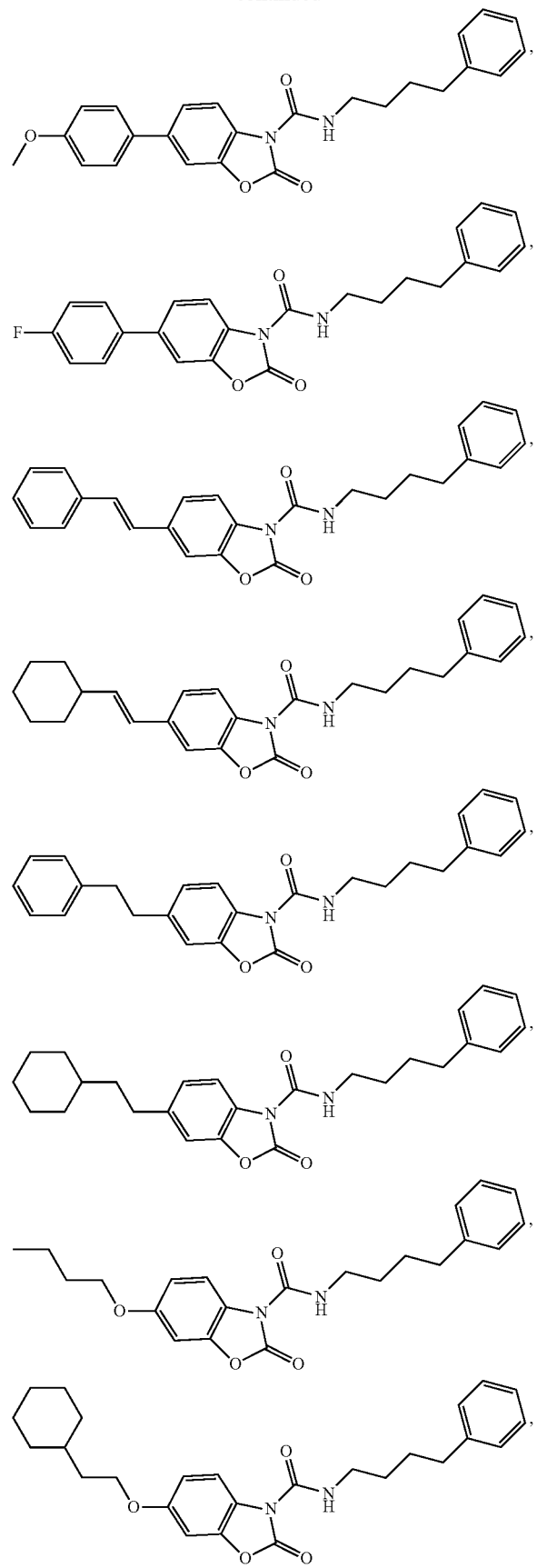
98
-continued
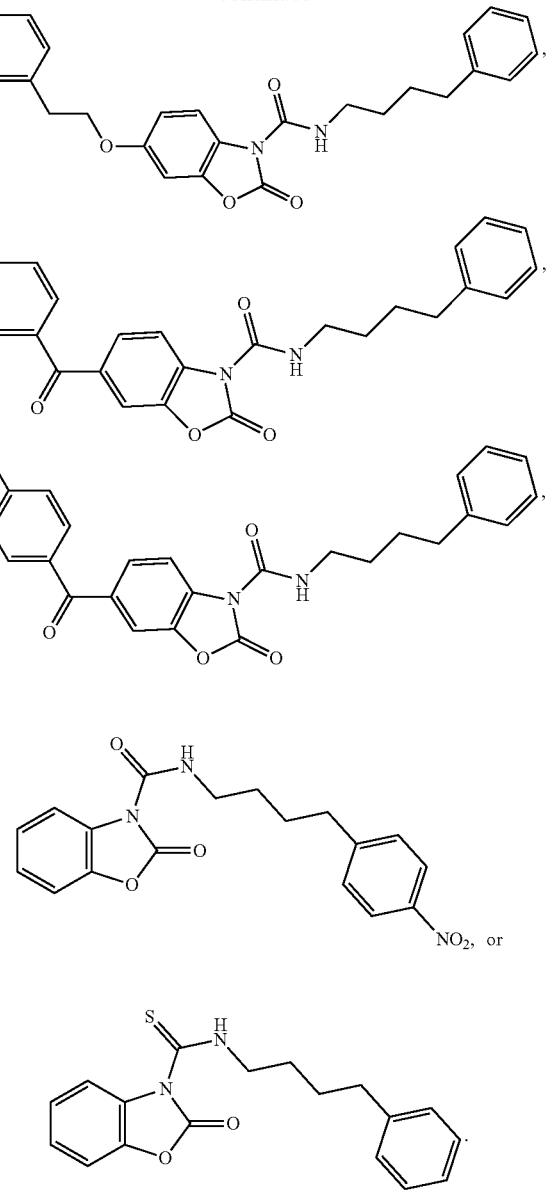
or a pharmaceutically acceptable salt thereof.
7. A method of treating cancer, inflammation, pain, inflammatory pain, or a pulmonary disease in a subject in need thereof, the method comprising administering to the subject an effective amount of a compound of Formula (I) or a pharmaceutically acceptable salt thereof:
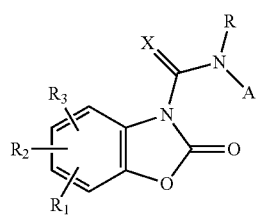
Formula (I)

wherein:

X is O or S;

R is hydrogen, linear or branched $C_{1-6}$ alkyl;

A is a linear or branched $C_{5-12}$ alkyl group or a group:

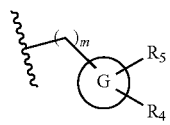

wherein:

m is an integer from 1 to 6;

G is a 3-10 membered saturated or unsaturated, aromatic or heteroaromatic, single or fused ring comprising up to three heteroatoms selected from N, O, S; and $R_4$ and $R_5$ are as defined below;

$R_1$ $R_2$, $R_3$, $R_4$ and $R_5$, are independently selected from the group consisting of hydrogen, halogen, linear or branched $C_{1-6}$ alkyl, optionally substituted cycloalkyl $C_{1-6}$ alkyl, optionally substituted cycloalkyl $C_{2-6}$ alkenyl, optionally substituted aryl $C_{1-6}$ alkyl, optionally substituted aryl $C_{2-6}$ alkyenyl, $C_{1-6}$ alkoxy, optionally substituted cycloalkyl $C_{1-6}$ alkoxy, optionally substituted aryl $C_{1-6}$ alkoxy, hydroxy $C_{1-6}$ alkyl, OH, CN, $NO_2$, fluoro $C_{1-6}$ alkyl, fluoro $C_{1-6}$ alkoxy, optionally substituted aryl, $C_{1-6}$ alkylCO, optionally substituted arylCO, optionally substituted aryl $C_{1-6}$ alkylCO, $COOR_7$, $CONR_8R_9$, and $SO_2R_{10}$; wherein $R_7$, $R_8$, $R_9$ and $R_{10}$ are independently selected from the group consisting of hydrogen and linear or branched $C_{1-6}$ alkyl; wherein $R_1$, $R_2$, $R_3$, $R_4$ and $R_5$ can be attached to any position of the ring to which they are connected.

8. The method of claim 7 wherein the compound has the formula:

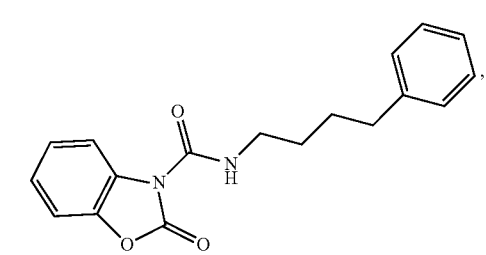

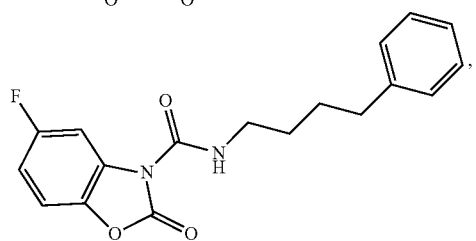

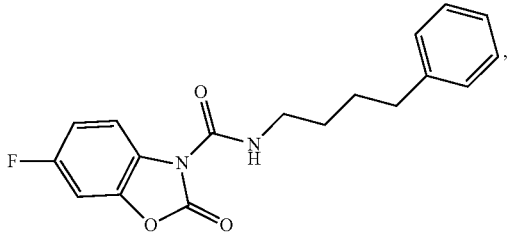

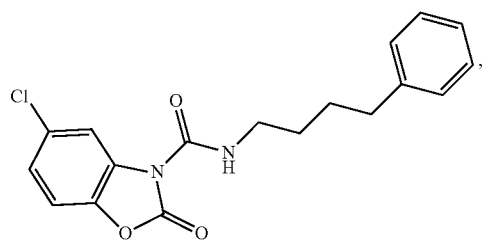

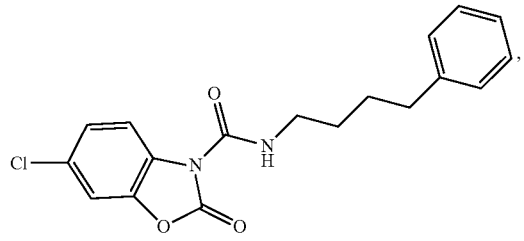

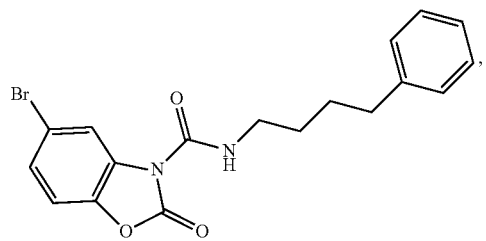

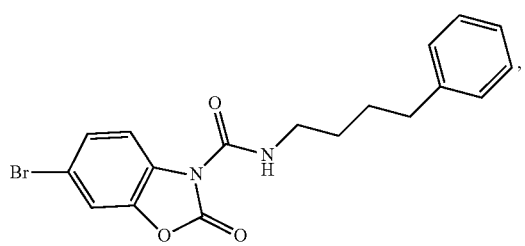

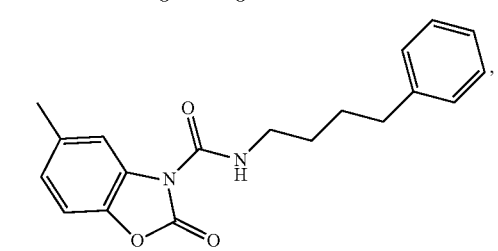

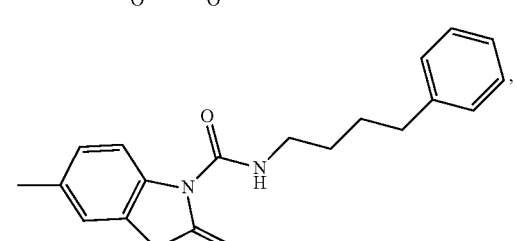

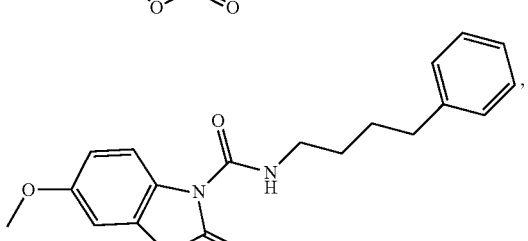

101
-continued
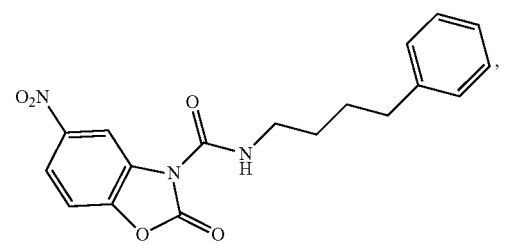
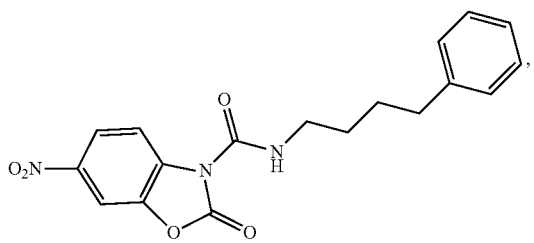
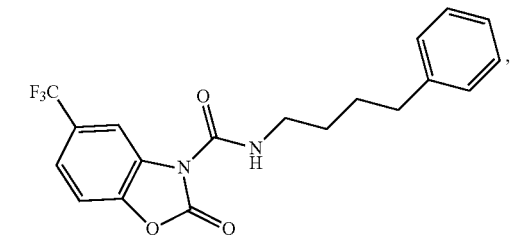
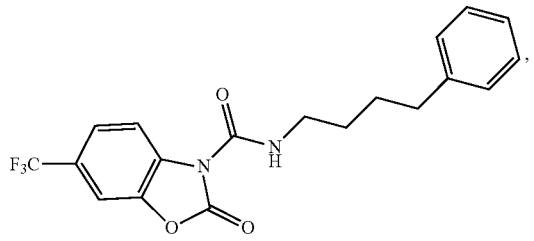
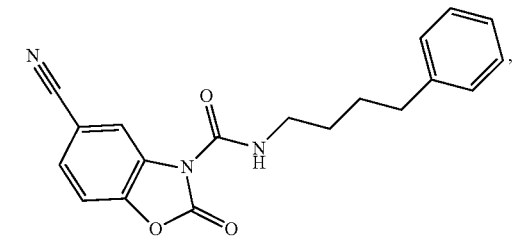
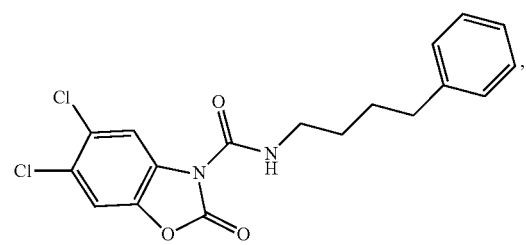
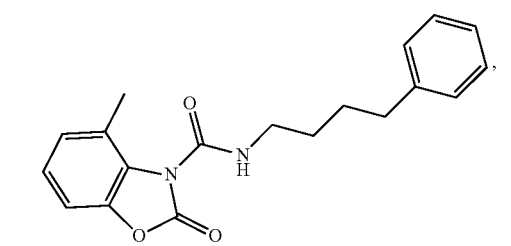
102
-continued
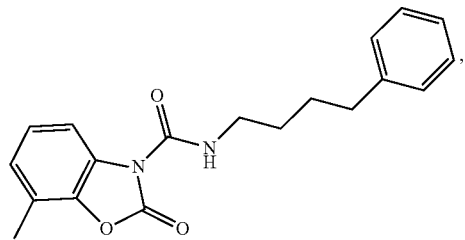
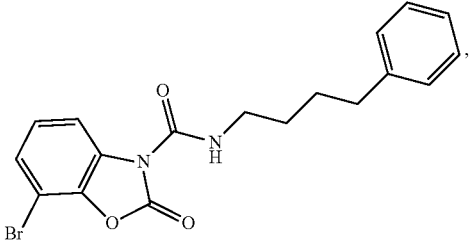
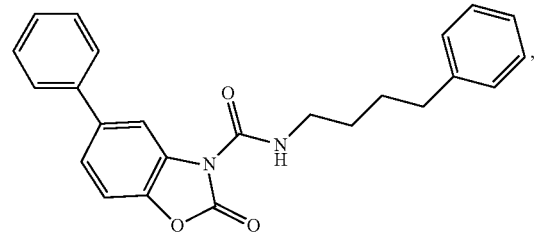
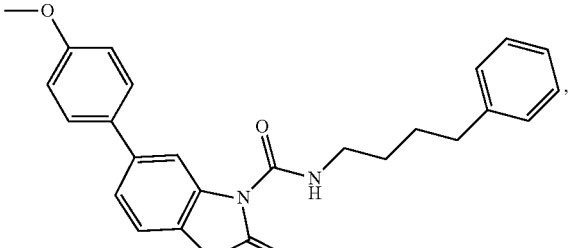
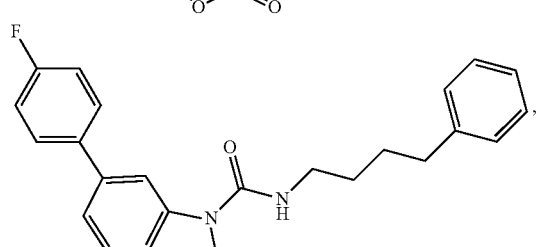
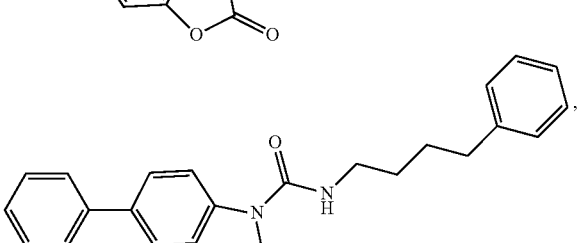
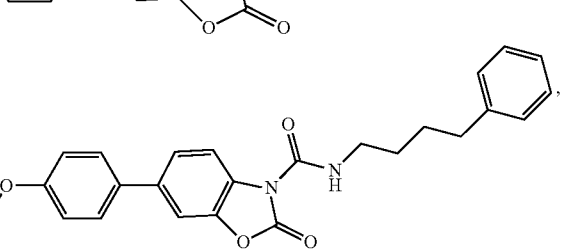

103
-continued
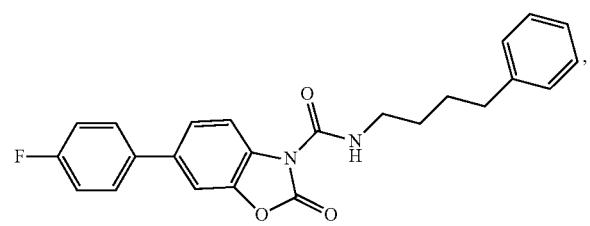
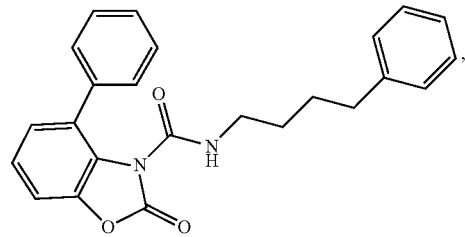
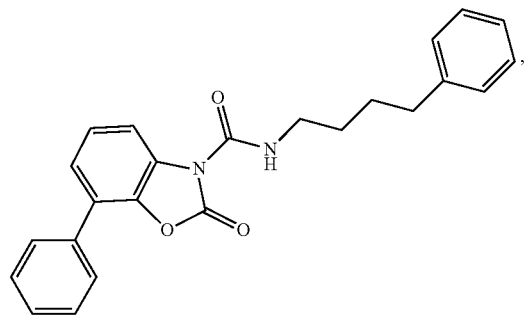
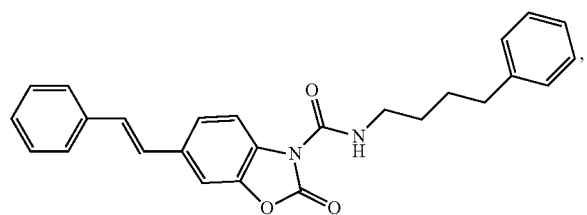
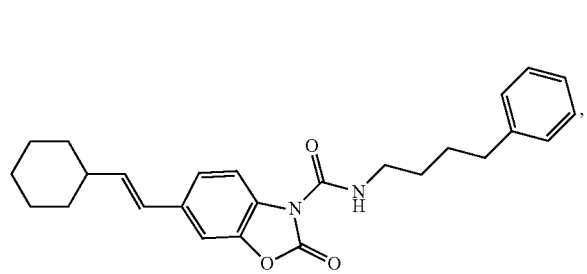
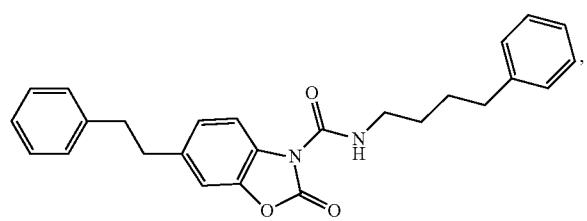
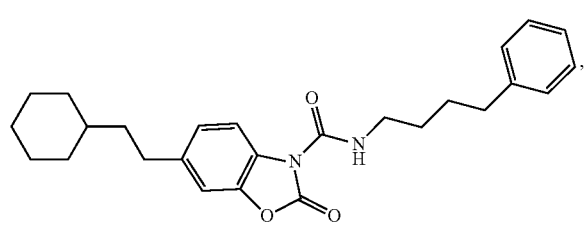
104
-continued
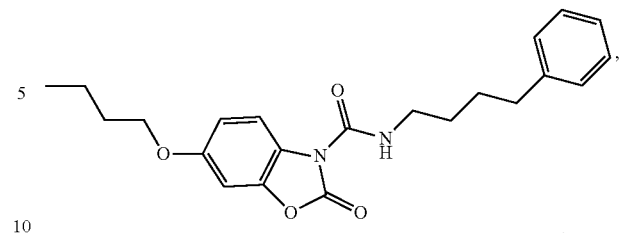
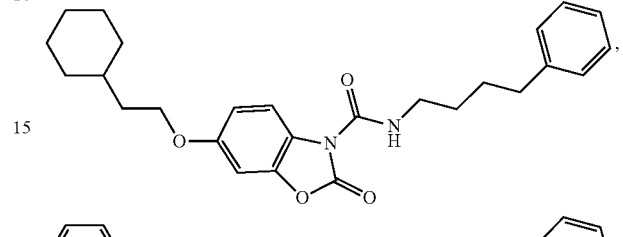
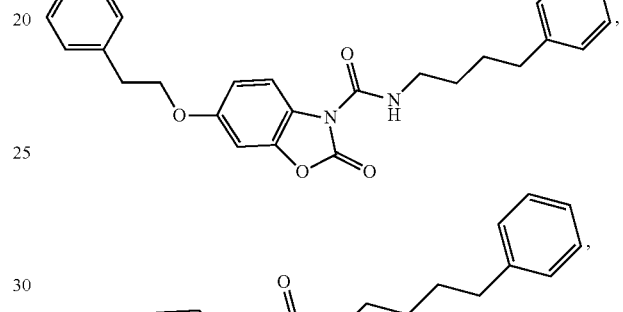
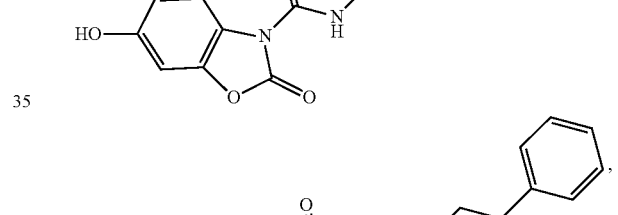
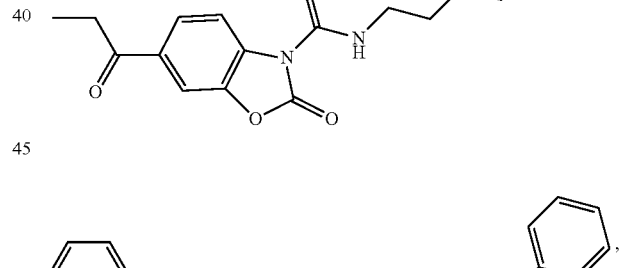
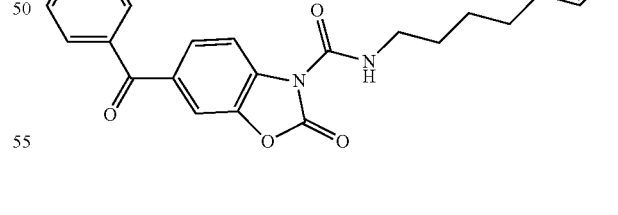
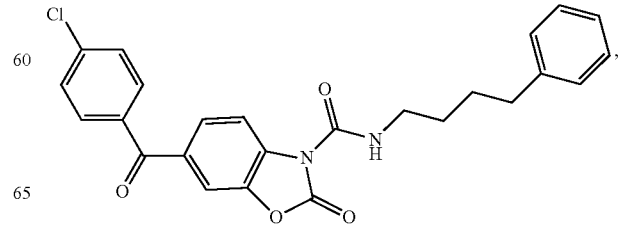

105
-continued
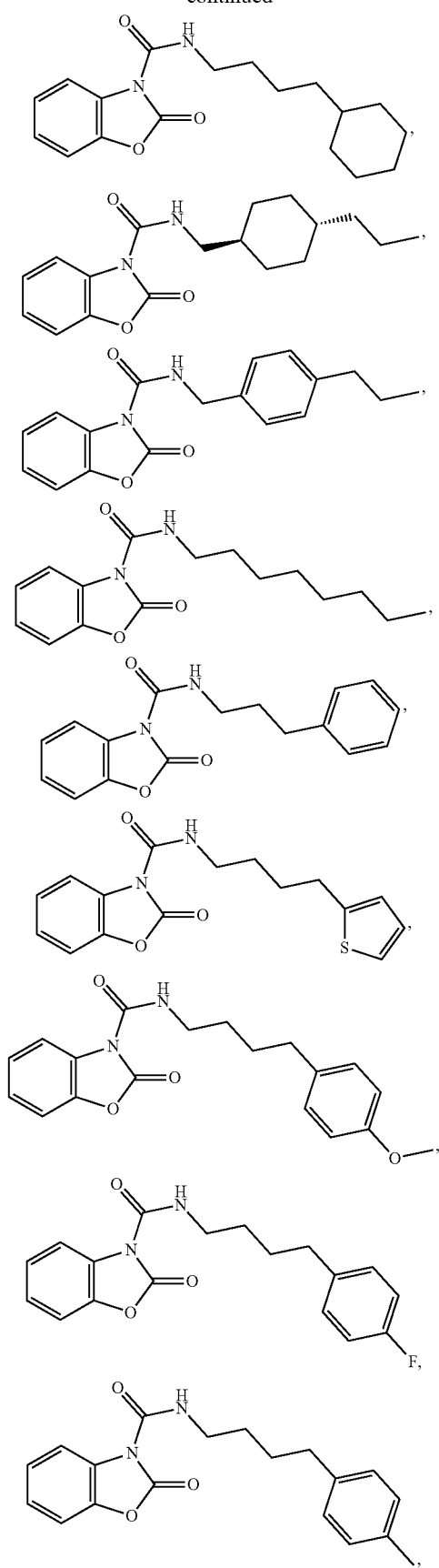
106
-continued
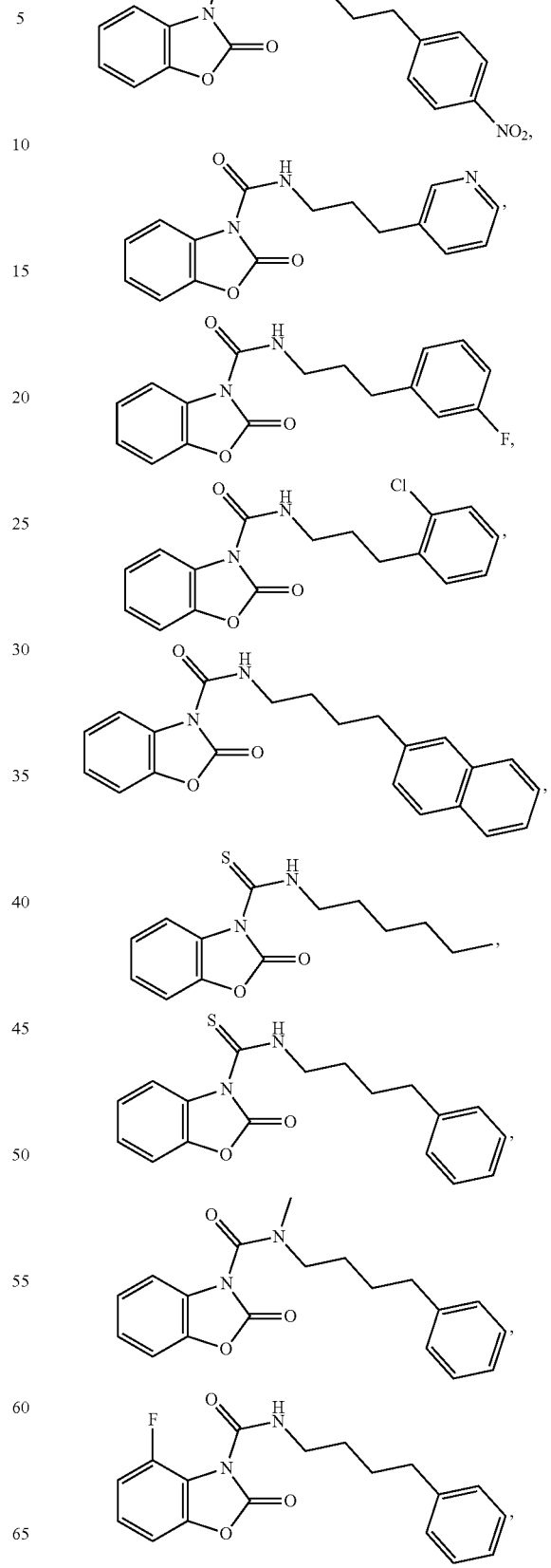

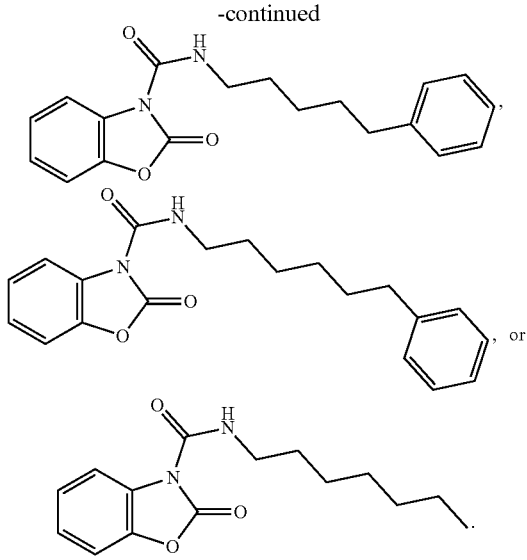

or a pharmaceutically acceptable salt thereof.

9. The method of claim 7 wherein:

X is O or S;

R is hydrogen or a linear or branched $C_{1-6}$ alkyl,

A is a linear or branched $C_{5-12}$ alkyl group or a group

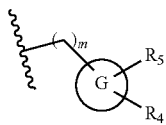

wherein:

m is an integer from 1 to 6;

G is an optionally $R_4$, $R_5$ substituted $C_3$-$C_{10}$ cycloalkyl which is cyclopropane, cyclobutane, cyclopentane, cyclopentene, cyclohexane, cyclohexene, cyclohexadiene, or cycloheptane;

an optionally $R_4$, $R_5$ substituted aryl which is phenyl, alpha- or beta-naphthyl, 9,10-dihydroanthracenyl, indanyl, fluorenyl or biphenyl;

an optionally $R_4$, $R_5$ substituted heteroaryl which is pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, thienyl, pyridyl, pyrazinyl, pyrimidinyl, pyridazinyl, quinolinyl, isoquinolinyl, quinazolinyl or quinoxalinyl; or an optionally $R_4$, $R_5$ substituted heterocyclic ring which is oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, thiazoline, isothiazoline, dioxane, piperazine, morpholine, thiomorpholine, hexamethyleneimine or homopiperazine; and $R_1$, $R_2$, $R_3$, $R_4$ and $R_5$ are independently selected from the group consisting of hydrogen, halogen, linear or branched $C_{1-6}$ alkyl, optionally substituted cycloalkyl $C_{1-6}$ alkyl, optionally substituted cycloalkyl $C_{2-6}$ alkenyl, optionally substituted aryl $C_{1-6}$ alkyl, optionally substituted aryl $C_{1-6}$ alkyenyl, $C_{1-6}$ alkoxy, optionally substituted cycloalkyl $C_{1-6}$ alkoxy, optionally substituted aryl $C_{1-6}$ alkoxy, hydroxy $C_{1-6}$ alkyl, OH, CN, $NO_2$, fluoro $C_{1-6}$ alkyl, fluoro $C_{1-6}$ alkoxy; optionally substituted aryl, $C_{1-6}$ alkylCO, optionally substituted arylCO, optionally substituted aryl $C_{1-6}$ alkylCO, $COOR_7$, $CONR_8R_9$, and $SO_2R_{10}$; wherein $R_7$, $R_8$, $R_9$ and $R_{10}$ are independently selected from the group consisting of hydrogen and linear or branched $C_{1-6}$ alkyl; wherein $R_1$, $R_2$, $R_3$, $R_4$ and $R_5$ can be attached to any position of the ring to which they are connected.

10. The method of claim 7 wherein:

X is O or S;

R is hydrogen or a linear or branched $C_{1-6}$ alkyl,

A is a linear or branched $C_{5-9}$ alkyl group or a group

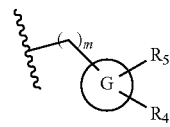

wherein:

m is an integer from 1 to 6;

G is an aryl selected from naphthyl or phenyl ($C_3$-$C_{10}$)cycloalkyl, or a heteroaryl which is pyridyl, tiophenyl, pyrimidinyl, furyl, or indolyl;

wherein $R_4$ and $R_5$, if present, independently are halogen, $NO_2$, ($C_1$-$C_3$)alkoxy-, ($C_3$-$C_{10}$) cycloalkyl, or linear or branched $C_1$-$C_6$ alkyl; $R_4$ and $R_5$ can be attached to any position of the ring to which they are connected, wherein $R_1$, and $R_2$, $R_3$, are independently hydrogen, halogen, linear or branched $C_{1-6}$ alkyl, OH, CN, $NO_2$, and/or fluoro $C_{1-6}$ alkyl, or hydroxy $C_{1-6}$ alkyl, phenyl optionally substituted with $C_1$-$C_6$ alkyl, $C_1$-$C_3$ alkoxy, $C_2$-$C_6$ alkenyl, halogen, $NO_2$, and/or $CF_3$phenyl $C_{1-6}$ alkyl optionally substituted with $C_1$-$C_6$ alkyl, $C_1$-$C_3$ alkoxy, $C_2$-$C_6$ alkenyl, halogen, $NO_2$, and/or $CF_3$, phenyl $C_{2-6}$ alkenyl optionally substituted with $C_1$-$C_6$ alkyl, $C_1$-$C_3$ alkoxy, $C_2$-$C_6$ alkenyl, halogen, $NO_2$, and/or $CF_3$;

phenyl CO optionally substituted with $C_1$-$C_6$ alkyl, $C_1$-$C_3$ alkoxy, $C_2$-$C_6$ alkenyl, halogen, $NO_2$, and/or $CF_3C_1$-$C_6$ alkyl CO optionally substituted with phenyl, optionally substituted with $C_1$-$C_6$ alkyl, $C_1$-$C_3$ alkoxy, $C_2$-$C_6$ alkenyl, halogen, $NO_2$, and/or $CF_3$;

($C_3$-$C_{10}$)cycloalkyl $C_{1-6}$ alkyl optionally substituted with $C_1$-$C_6$ alkyl, $C_{2-6}$ alkenyl, and/or halogen, ($C_3$-$C_{10}$)cycloalkyl $C_{2-6}$ alkenyl optionally substituted with $C_1$-$C_6$ alkyl, $C_2$-$C_6$ alkenyl, and/or halogen, or $C_{1-6}$ alkoxy optionally substituted with halogen, ($C_3$-$C_{10}$) cycloalkyl, and/or phenyl;

wherein $R_1$, $R_2$, $R_3$, can be attached to any position of the ring to which they are connected.

11. The method of claim 10 wherein
X is O;
R is hydrogen;
A is a linear or branched $C_{5-9}$ alkyl group or a group

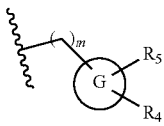

wherein:
m is an integer from 1 to 4;
G is phenyl, thiophenyl, pyridyl, naphthyl or $C_{3-7}$ cycloalkyl; and
$R_1$, $R_2$, $R_3$, $R_4$ and $R_5$, are, independently, H, F, Cl, Br, Me, Et, Pr, MeO, BuO, OH, CN, $NO_2$, $CF_3$, Ph, MeCO, or EtCO;
wherein $R_1$, $R_2$, $R_3$, $R_4$ and $R_5$ can be attached to any position of the ring to which they are connected.

12. The method of claim 7 wherein the method treats cancer wherein the cancer is prostate cancer, colon cancer, skin cancer, or a skin precancerous condition.

13. The method of claim 7 wherein the method treats an inflammatory disease, a pulmonary disease, pain syndrome or neuropathic pain.

14. A method of treating cancer, inflammation, pain, inflammatory pain, or a pulmonary disease in a subject in need thereof, the method comprising administering to the subject a pharmaceutical composition comprising a compound of Formula (I), or a pharmaceutically acceptable salt thereof and a pharmaceutically acceptable carrier:

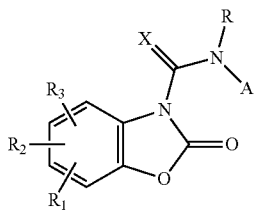

Formula (I)
wherein:
X is O or S;
R is hydrogen or linear or branched $C_{1-6}$ alkyl;
A is a linear or branched $C_{5-12}$ alkyl group or a group:

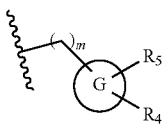

wherein:
m is an integer from 1 to 6;
G is a 3-10 membered saturated or unsaturated, aromatic or heteroaromatic, single or fused ring comprising up to three heteroatoms selected from N, O, and S; and $R_4$ and $R_5$ are as defined below;
$R_1$, $R_2$, $R_3$, $R_4$ and $R_5$, are independently selected from the group consisting of hydrogen, halogen, linear or branched $C_{1-6}$ alkyl, optionally substituted cycloalkyl $C_{1-6}$ alkyl, optionally substituted cycloalkyl $C_{2-6}$ alkenyl, optionally substituted aryl $C_{1-6}$ alkyl, optionally substituted aryl $C_{2-6}$ alkyenyl, $C_{1-6}$ alkoxy, optionally substituted cycloalkyl $C_{1-6}$ alkoxy, optionally substituted aryl $C_{1-6}$ alkoxy, hydroxy $C_{1-6}$ alkyl, OH, CN, $NO_2$, fluoro $C_{1-6}$ alkyl, fluoro $C_{1-6}$ alkoxy, optionally substituted aryl, $C_{1-6}$ alkylCO, optionally substituted arylCO, optionally substituted aryl $C_{1-6}$ alkylCO, $COOR_7$, $CONR_8R_9$, and $SO_2R_{10}$ wherein $R_7$, $R_8$, $R_9$ and $R_{10}$ are independently selected from the group consisting of hydrogen, linear or branched $C_{1-6}$ alkyl; wherein $R_1$, $R_2$, $R_3$, $R_4$ and $R_5$ can be attached to any position of the ring to which they are connected.

15. The method of claim 14 wherein the pharmaceutical composition comprises an additional pharmaceutically active ingredient.

16. The method of claim 15 wherein the additional pharmaceutically active ingredient is an anticancer agent, an antinflammatory agent, an analgesic compound, an agent effective on pulmonary diseases, or mixtures thereof.

17. A method of treating a disorder or disease associated with non-physiological levels of acid ceramidase protein or function in a subject in need thereof, the method comprising administering to the subject an effective amount of the compound of claim 1.

18. A method of treating a disease selected from cancer or a precancerous condition, an inflammatory disease, a pulmonary disease, a pain syndrome or neuropathic pain in a subject in need thereof, the method comprising administering to the subject an effective amount of the compound of claim 1.

19. A method of treating prostate cancer, colon cancer, a skin cancer or a skin precancerous condition in a subject in need thereof, the method comprising administering to the subject an effective amount of the compound of claim 1.

20. The method of claim 17 further comprising administering to the subject an effective amount of an additional pharmacologically active ingredient selected from an anticancer agent, an antinflammatory agent, an analgesic compound, an agent effective on pulmonary diseases and mixtures thereof.

21. The method of clam 12, wherein the skin cancer is melanoma.

* * * * *